United States Patent [19]

Nonami et al.

[11] Patent Number: 4,935,810
[45] Date of Patent: Jun. 19, 1990

[54] THREE-DIMENSIONAL MEASURING APPARATUS

[75] Inventors: Tetsuo Nonami; Kazuo Sonobe, both of Tokyo, Japan

[73] Assignee: Olympus Optical Co., Ltd., Tokyo, Japan

[21] Appl. No.: 376,460

[22] Filed: Jul. 7, 1989

[30] Foreign Application Priority Data

| Oct. 26, 1988 [JP] | Japan | 63-271493 |
|---|---|---|
| Feb. 17, 1989 [JP] | Japan | 1-38811 |
| Feb. 17, 1989 [JP] | Japan | 1-38812 |
| Feb. 17, 1989 [JP] | Japan | 1-38813 |

[51] Int. Cl.$^5$ .......................... A61B 1/04; A61B 1/06; H04N 13/00; H04N 7/18
[52] U.S. Cl. .......................................... 358/98; 128/6; 358/88; 358/107
[58] Field of Search ................. 358/98, 88, 107; 128/6

[56] References Cited

U.S. PATENT DOCUMENTS

| 4,621,284 | 11/1986 | Nishioka | 358/98 |
| 4,656,508 | 4/1987 | Yokota | 358/98 |
| 4,862,873 | 9/1989 | Yajima | 128/6 |

FOREIGN PATENT DOCUMENTS

| 58-36927 | 3/1983 | Japan . |
| 63-63432 | 3/1988 | Japan . |
| 1-24215 | 1/1989 | Japan . |

Primary Examiner—Howard W. Britton
Attorney, Agent, or Firm—Armstrong, Nikaido, Marmelstein, Kubovcik & Murray

[57] ABSTRACT

This three-dimensional measuring apparatus comprises an imaging apparatus imaging a plurality of images having parallaxes, a displaying apparatus displaying on a plurality of pictures the plurality of images obtained by the imaging apparatus, a first object point designating apparatus designating a first object point corresponding to the measuring object point in the space on the first image of the plurality of images displayed by the displaying apparatus, a second object point designating apparatus designating a second object point corresponding to the measuring object point in the space on the second image of the plurality of images displayed by the displaying apparatus, an object point designating auxiliary apparatus making an auxiliary process relating to the second object point designation by the second object point designating apparatus after the first object point designation by the first object point designating apparatus and an operating apparatus making a measuring operation relating to the three-dimensional position of the measuring object point specified by the first object point designated by the first object point designating apparatus and the second object point designated by the second object point designating apparatus.

36 Claims, 43 Drawing Sheets

LEFT PICTURE

RIGHT PICTURE

LEFT IMAGING DEVICE

RIGHT IMAGING DEVICE

IMAGING DEVICE

LEFT IMAGE PART

GUIDE LINE FOR IMAGE
CONTAINING NO DISTORTION
OF DISTORTION ABERRATION

LEFT IMAGE PART

GUIDE LINE FOR IMAGE
CONTAINING DISTORTION
OF DISTORTION ABERRATION

RIGHT IMAGE PART

INDEX CIRCLE FOR IMAGE
CONTAINING NO DISTORTION
OF DISTORTION ABERRATION

RIGHT IMAGE PART

INDEX CIRCLE FOR IMAGE
CONTAINING DISTORTION
OF DISTORTION ABERRATION

IN CASE POSITION DESIGNATION OF OBJECT POINT IS CORRECT

IN CASE POSITION DESIGNATION OF OBJECT POINT IS NOT CORRECT

THREE-DIMENSIONAL MEASURING APPARATUS

BACKGROUND OF THE INVENTION

1. Field of the Invention

This invention relates to a three-dimensional measuring apparatus for measuring an inspected object in relation to its three-dimensional positioin.

2. Related Art Statement

Recently, an endoscope has come to be extensively used in the medical and industrial fields.

For example, in an observed image by an ordinary endoscope, generally the inspected part is plane and the unevenness is hard to recognize. Therefore, for example, in the publication of a Japanese patent application laid open No. 24215/1989 is disclosed an apparatus wherein two systems of objective lenses are provided in the tip part of an endoscope so that two picture images obtained by these two systems of objective lenses may be led to an eyepiece part through an image guide to obtain a cubic visual field by binoculars. Also, in the publication of a Japanese patent application laid open No. 46927/1983 is disclosed a stereo-visible endoscope provided in the tip part with two imaging optical systems and two solid state imaging devices.

However, with such endoscope, though a cubic visual field can be obtained, there has been a disadvantage that the distance to the image within the visual field can not be obtained.

A technique for dissolving this disadvantage is disclosed in the publication of a Japanese patent application laid open No. 63432/1988. In this technique, as shown in FIG. 51(a), in order to designate measuring object points in the space, the positions of measuring object points in the respective images are given by a pointing device or the like on a plurality of images having parallaxes and thereby straight lines in the space passing through the imaging means imaging the images and the measuring object points are determined. When the positions of the measuring object points are given on the respective images by a plurality of imaging means arranged in the positions having parallaxes, a plurality of straight lines will be thereby determined in the space. Generally, the straight lines in the space can not be said to always have intersections but should all pass through the measuring object points. Therefore, if the positions are well accurately designated, the positions of the measuring object points for the imaging means in the space will be able to be calculated as the intersections of these straight lines.

However, there has been a problem that, in an endoscope image, the object wanted to be measured is not always accompanied with a clear feature point and, in case there is no clear feature point, the position designation on the respective pictures of the measuring object points will be likely to be inaccurate. Therefore, as shown in FIG. 51(b), the straight lines in the space to pass through the measuring object points will have no intersection and the distance has not been able to be measured.

Now, as a means of designating the points on the pictures of the respective monitors, for example, it is considered to designate the points by displaying cursors on the pictures of the respective monitors and moving these cursors to desired positions.

However, there has been a problem that, if such means of moving the above mentioned cursors as, for example, mice are separately provided for the cursors of the respective pictures, the operation will be complicated.

Further, there is a problem that, if cursors are displayed on the pictures of both monitors, the cursor on which picture is the moved cursor and on which picture the points can be designated are hard to know.

Though the size of the object can be numerically known as described above, on the other hand, it is desired to directly know the size of the object by sight.

Objects and Summary of the Invention

An object of the present invention is to provide a three-dimensional measuring apparatus whereby the designation of respective object points on a plurality of images having parallaxes to specify measuring object points in the space is made easy.

Another object of the present invention is to provide a three-dimensional measuring apparatus whereby respective object points on a plurality of images having parallaxes can be accurately designated to specify measuring object points in the space.

Further another object of the present invention is to provide a three-dimensional measuring apparatus whereby respective object points on a plurality of images having parallaxes can be easily designated by one designating means to specify measuring object points in the space.

Further another object of the present invention is to provide a three-dimensional measuring apparatus whereby the size of the object can be known by sight.

The three-dimensional measuring apparatus of the present invention comprises an imaging means imaging a plurality of images having parallaxes, a displaying means displaying on a plurality of pictures the plurality of images obtained by the above mentioned imaging means, a first object point designating means designating a first object point corresponding to the measuring object point in the space on the first image among a plurality of images displayed by the above mentioned displaying means, a second object point designating means designating a second object point corresponding to the above mentioned measuring object point in the space on the second image among the plurality of images displayed by the above mentiioned displaying means, an object point designating auxiliary means making an auxiliary process relating to the second object point designation by the above mentioned second object point designating means after the first object point designation by the above mentioned first object point designating means and an operating means making a measuring operation relating to the three-dimensional position of the above mentioned measuring object point specified by the first object point designated by the above mentioned first object point designating means and the second object point designated by the above mentioned second object point designating means.

The other features and advantages of the present invention will become apparent enough with the following explanation.

BRIEF DESCRIPTION OF THE DRAWINGS

FIG. 1 is a block diagram showing the formation of a measuring endoscope apparatus of the present invention.

FIG. 2 is a view showing a tip part of a cubic endoscope image take-in apparatus.

FIG. 3 is a view showing an operating panel of a cursor information designating means.

FIG. 4 is a view showing an example of an operating picture.

FIG. 5 is an explanatory view of a method of calculating the position of a guide line and the position of an object point.

FIG. 6 is a block diagram showing the schematic formation of this embodiment.

FIG. 7 is an explanatory view of the tip part of an insertable part of an endoscope.

FIG. 8 is a block diagram showing the formation of a measuring endoscope apparatus.

FIG. 9 is a block diagram showing the formation of a host computer.

FIG. 10 is a principle explaining view showing a method of determining a guide line.

FIG. 11 is a principle explaining view showing a method of determining a three-dimensional coordinate.

FIG. 12 is a principle explaining view showing a method of determining an index circle.

FIG. 13 is an explanatory view for explaining the exchange of the position on a picture and the position on an imaging device.

FIG. 14 is an explanatory view showing a guide line displayed in the left picture.

FIG. 15 is an explanatory view showing an index circle displayed in the right picture.

FIGS. 16 to 25 are flow charts for explaining the operation of this embodiment.

FIG. 30 is a principle explaining view of a distortion aberration correction.

FIG. 31 is an explanatory view showing a guide line displayed in the left picture.

FIG. 32 is an explanatory view showing an index circle displayed in the right picture.

FIGS. 33 to 37 are flow charts for explaining the operation of this embodiment.

FIG. 42 is a block diagram showing the schematic formation of this embodiment.

FIG. 43 is a block diagram showing the formation of a measuring endoscope apparatus.

FIG. 44 is a block diagram showing the formation of a host computer.

FIGS. 45 to 49 are flow charts for explaining the operation of this embodiment.

DETAILED DESCRIPTION OF THE PREFERRED EMBODIMENTS

The first embodiment of the present invention is shown in FIGS. 1 to 5.

Figure 1:
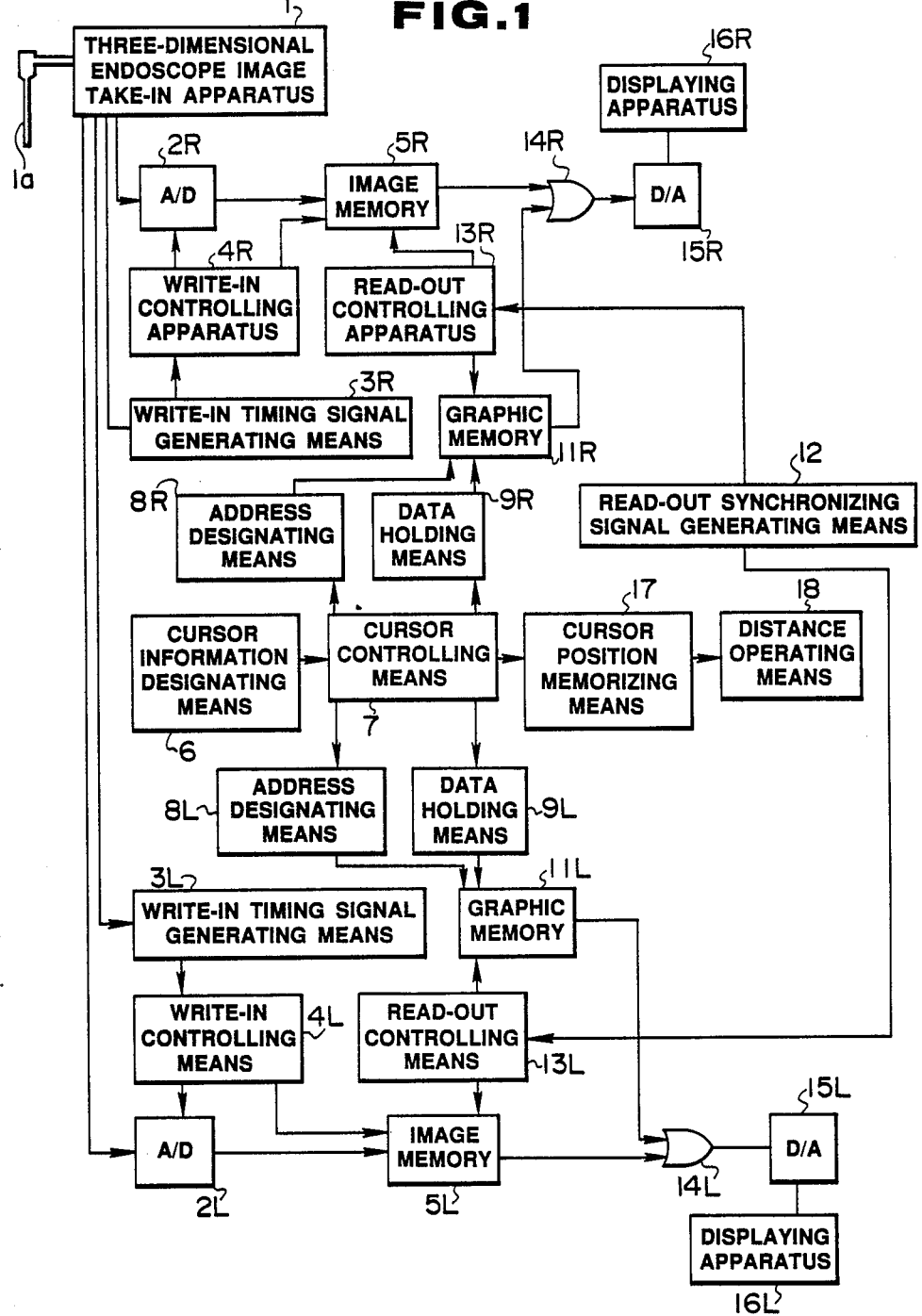
FIGS. 1 to 5 relate to the first embodiment of the present invention.
Figure 2:
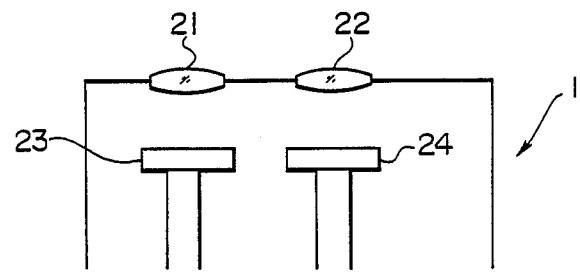

As shown in FIG. 1, the measuring endoscope apparatus of this embodiment is provided with a cubic endoscope image take-in apparatus 1 which has an elongate insertable part 1a. As shown in FIG. 2, image forming optical systems 21 and 22 are provided in the tip part of this insertable part 1a. Such solid state imaging devices 23 and 24 as CCD's as imaging means are provided respectively in the image forming positions of these image forming optical systems 21 and 22. The light reflected from an object of the illuminating light emitted from an illuminating means not illustrated is made to form images by the above mentioned image forming optical systems 21 and 22 and the images are photoelectrically converted by the above mentioned solid state imaging devices 23 and 24 and are output respectively as left (L) and right (R) electric image signals which are digital-converted respectively by A/D converters 2L and 2R and are then memorized respectively in image memories 5L and 5R.

Also, from the above mentioned cubic endoscope image take-in apparatus 1, synchronizing signals are fed to write-in timing controlling means 3L and 3R which feed write-in timing controlling signals to write-in controlling means 4L and 4R on the basis of these synchronizing signals. By the control signals from these write-in controlling means 4L and 4R, the writing of the image signals into the above mentioned memories 5L and 5R from the above mentioned A/D converters 2L and 2R are controlled.

The measuring endoscope apparatus of this embodiment is provided also with a cursor information indicating means 6 as a measuring object point designating means for indicating the information relating to the position of the cursor in the image. The cursor position information is fed from this cursor information indicating means 6 to a cursor controlling means 7 as an operating means and guide line displaying means. This cursor controlling means 7 is formed of a CPU having a calculating function, the displaying position of the cursor on the picture is calculated from the above mentioned cursor position information, the positions to display the points on the picture forming the cursor are housed in address designating means 8L and 8R, the colors to be written in are housed in data holding means 9L and 9R and further whether the cursor is on the guide line or not is judged. Also, the outputs of the above mentioned address designating means 8 and data holding means 9L and 9R are memorized in graphic memeories 11L and 11R which are memories holding cursor images respectively on the left and right pictures and have a memorizing capacity of 3 bits per pixel if the kinds of the colors of the cursors are three kinds. The images of the cursors held by these graphic memories 11L and 11R will be renewed when the data of the colors read out of the above mentioned data holding means 9L and 9R are written into the coordinate positions on the picture read out of the above mentioned address designating means 8L and 8R during the vertical flyback line period or horizontal flyback line period of the synchronizing signals from read-out controlling means 13L and 13R.

Read-out synchronizing signals from a read-out synchronizing signal generating means 12 are applied to the above mentioned read-out controlling means 13L and 13R. Synchronizing signals for synchronizing and reading out data corresponding to the same picture positions from the respective memories for the above mentioned image memories 5L and 5R and graphic memories 11L and 11R on the basis of these synchronizing signals are fed to these read-out controlling means 13. The respective data read out of the above mentioned image memories 5L and 5R and graphic memories 11L and 11R are input into logical sum operators 14L and 14R.

In these logical sum operators 14L and 14R, a logical sum of the data output from the above mentioned image memories 5L and 5R and the data output from the above mentioned graphic memories 11L and 11R is calculated and the results are output to D/A converters 15L and 15R. Digital type image signals are converted to analogue type video signals by these D/A converters 15L and 15R and images are displayed in image displaying apparatus 16L and 16R as displaying means.

The measuring endoscope apparatus of this embodiment is further provided with a cursor position memorizing means 17 memorizing a plurality of cursor positions in a cubic image when a memory is indicated by the above mentioned cursor information designating means 6 and a distance operating means 18 as a distance calculating means reading out the cursor positions memorized by this cursor position memorizing means 17 by the indication of the distance operation from the above mentioned cursor information designating means 6, operating the distances between the respective cursor positions and outputting the results to a displaying apparatus not illustrated.

The actual operation of the measuring endoscope apparatus of this embodiment formed as mentioned above shall be explained in the following.

The left and right image signals from the cubic endoscope image take-in apparatus 1 are digital-converted respectively by the A/D converters 2L and 2R and are then memorized in the image memories 5L and 5R. The image signals memorized in these image memories 5L and 5R are read out usually at a real time, have logical sums operated by the logical sum operators 14L and 14R and are converted to analogue type signals by the D/A converters 15L and 15R and then images are displayed in the displaying apparatus.

Figure 3:
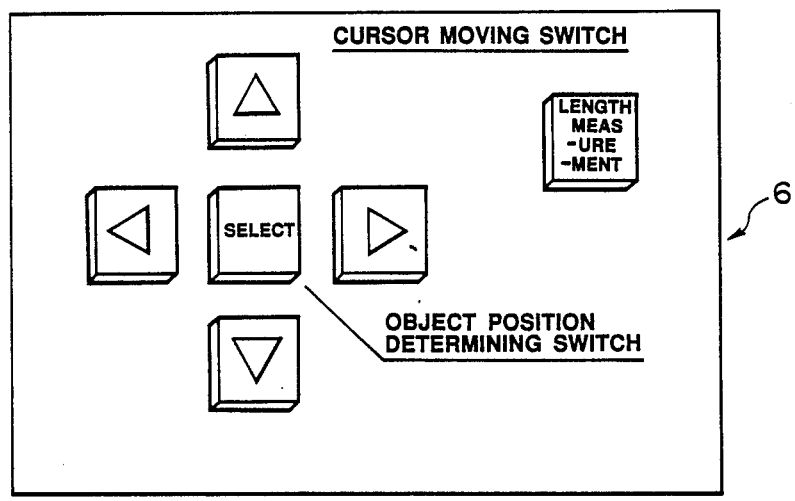
Figure 4A:
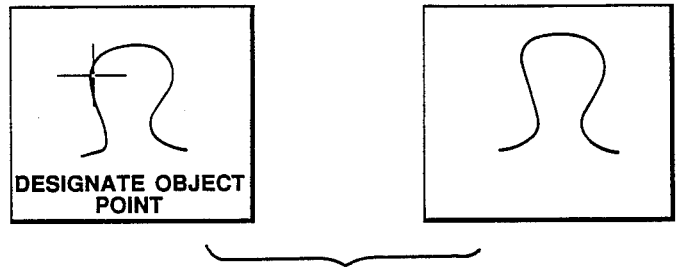
Figure 4B:
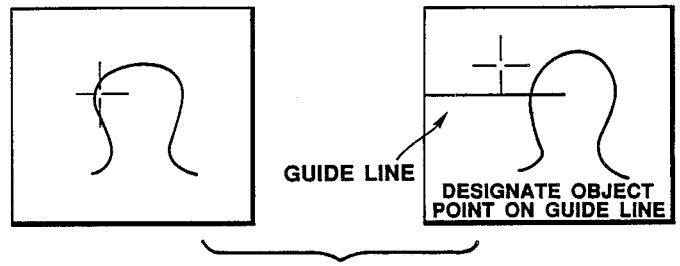
Figure 4C:
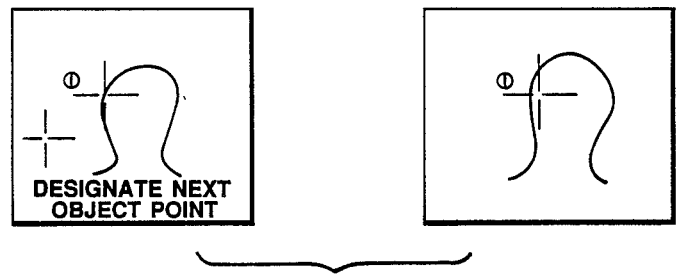

In case the object intended to be measured by the operator is contained within the visual field, in order to prevent the lag of the position designation by the motion within the living body, first the images to be memorized by the above mentioned image memories 5L and 5R are stilled. Then the cursor within the left image is moved to the position of the object point to be measured in the length by the cursor information designating means 6 having an operating panel formed as shown in FIG. 3. The state of the picture of the displaying apparatus 15 at this time will be such as is shown in FIG. 4(A). The position of the cursor can be moved by operating a cursor moving switch provided in the above mentioned cursor information designating means 6. Next, the position of the object point is memorized by pushing a selecting switch provided within the above mentioned cursor information designating means 6. The thus selected object point has the selected position displayed on the picture as shown in FIG. 4(B) to make the position definite. Then the cursor controlling means 7 designates the position of the guide line by the later described method from the position of the designated object and displays it in the right image. The state of the picture in the image in the displaying apparatus 16 at this time is shown in FIG. 4(C). Then the operator selects the position of the object point in the right image by the same operation. At this time, only the point on the guide line can be designated.

The above mentioned cursor controlling means 7 checks whether the position of the selected point is already in the calculated positiion of the guide line. If the position of the selected point is not in the position of the guide line, a warning sound will be issued by a warning apparatus not illustrated and the selection will be made ineffective. When the point on the guide line is selected, the position of the object point in the space will be defined and therefore this position will be calculated by the later described method and will be memorized. The state on the picture of the displaying apparatus 16 at this time is shown in FIG. 4(C). The position of the point measured in the length by repeating such operation is memorized and then the distances between the respective designated points are displayed in a displaying apparatus not illustrated by pushing a length measuring switch. When the coordinates of the two points at this time are represented by $(x_1, y_1, z_1)$ and $(x_2, y_2, z_2)$, the distance d between the two points will be given by the following formula:

$$d=[(x_1-x_2)^2+(y_1-y_2)^2+(z_1-z_2)^2]^{\frac{1}{2}}$$

Also, the distance from the tip of the insertable part to a certain point can be determined in the same manner.

Figure 5:
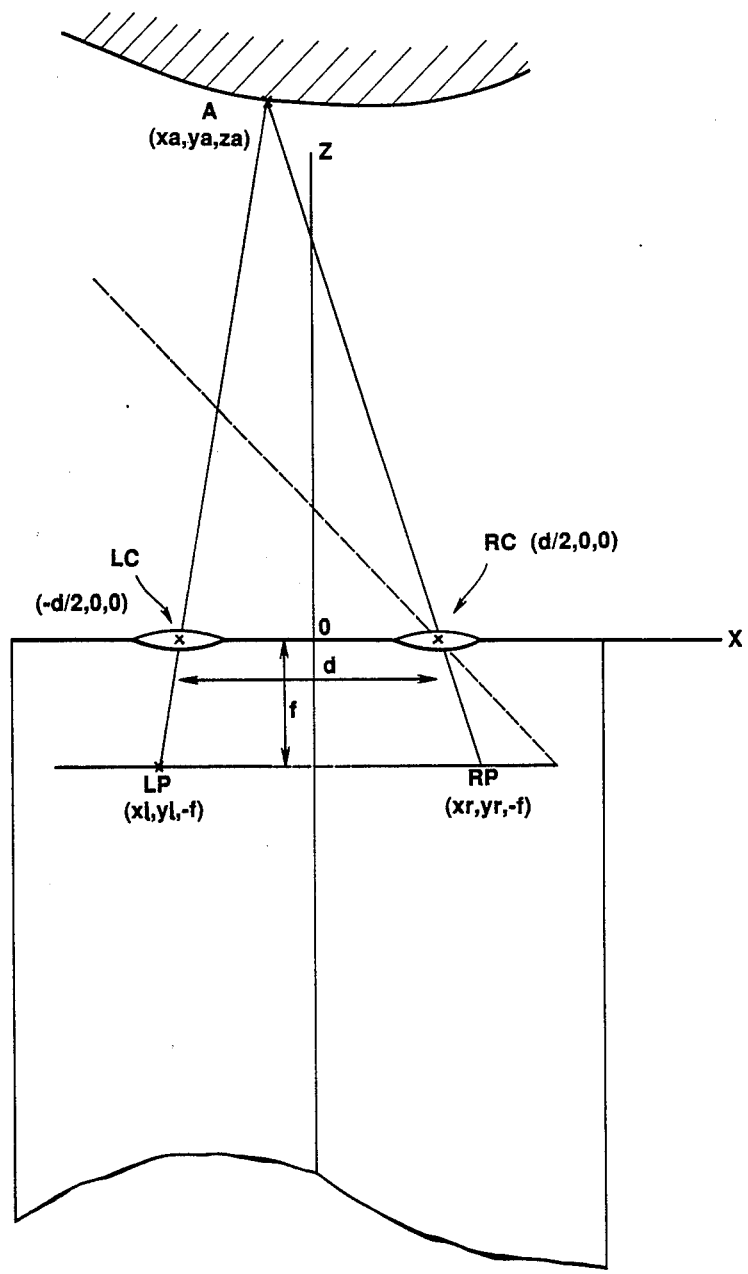

Now, the method of calculating the position of the guide line and the position of the object point shall be explained with reference to FIG. 5.

The operation of designating one point in the image is the same as the operation of designating the image forming plane of the objective optical system. Here, for the sake of the explanation, the center of the coordinates in the space shall be the intermediate point of both right and left imaging means, the direction of the X axis shall be the direction passing through the centers of both right and left imaging means, the direction of the Z axis shall be the vertical direction from the tip surface of the endoscope apparatus and the direction of the Y axis shall be the direction intersecting at right angles with either of the X axis and Z axis. The parallax shall be d. The center of the left imaging means shall be represented by LC $(-d/2, 0, 0)$, the center of the right imaging means shall be represented by RC$(d/2, 0, 0)$, the position of the object point shall be represented by A$(x_a, y_a, z_a)$, the focal distance shall be represented by f and the position of the object in the designated left image shall be represented by LP$(x_1, y_1, f)$. Then the straight line passing through A and LP will be represented as follows wherein t represents a parameter:

$$(x, y, z) = (-d/2 - x_1, -y_1, f) t + (-d/2, 0, 0) \quad (t > 0)$$

Then the intersection of the straight line passing through the point on this straight line and RC with the right imaging surface is determined. If the coordinate of this intersection RP is represented by $(x_r, y_r, -f)$, the following relative formula will be established:

$$(x_r, y_r, -f) = (x_l + d + d/t, y_l, -f) \quad (t > 0)$$

Thereby, the guide line will be from the left end of the picture to the point corresponding to $(x_1+d, y_1, -f)$.

When one point of the guide line is designated, the position of the object point will be the intersection of the straight lines represented by the following two formulae wherein t and s are parameters:

$$(xa, ya, za) = (-d/2 - x_l, -y_l, f) t + (-d/2, 0, 0). \quad (t > 0)$$

$$(xa, ya, za) = (d/2 - x_r, -y_r, f) s + (d/2, 0, 0). \quad (s > 0)$$

Therefore, by solving the above formulae, $$(xa, ya, za) = (-d/2 - x_l, -y_l, r) t + (-d/2, 0, 0).$$

$$[t = d/(x_r - x_l - d)]$$

will be given.

By making such operation as is mentioned above, the position of the guide line and the position of the object point can be calculated.

As described above, according to this embodiment, when a measuring object point is designated on one picture, how a straight line in the space passing through the imaging means having imaged the picture and this measuring object point should appear to the other imaging means will be operated and the straight line will be displayed as a guide line on the other picture. Further, as the other points than the point on this guide line can not be designated as object points, the position of the object point can be accurately designated and thereby the distance and length can be accurately measured.

By the way, in this embodiment, respective displaying apparatus are provided on the right and left images but one displaying apparatus may be provided to display both right and left images in one displaying apparatus.

The second embodiment of the present invention is shown in FIGS. 6 to 25.

Figure 8:
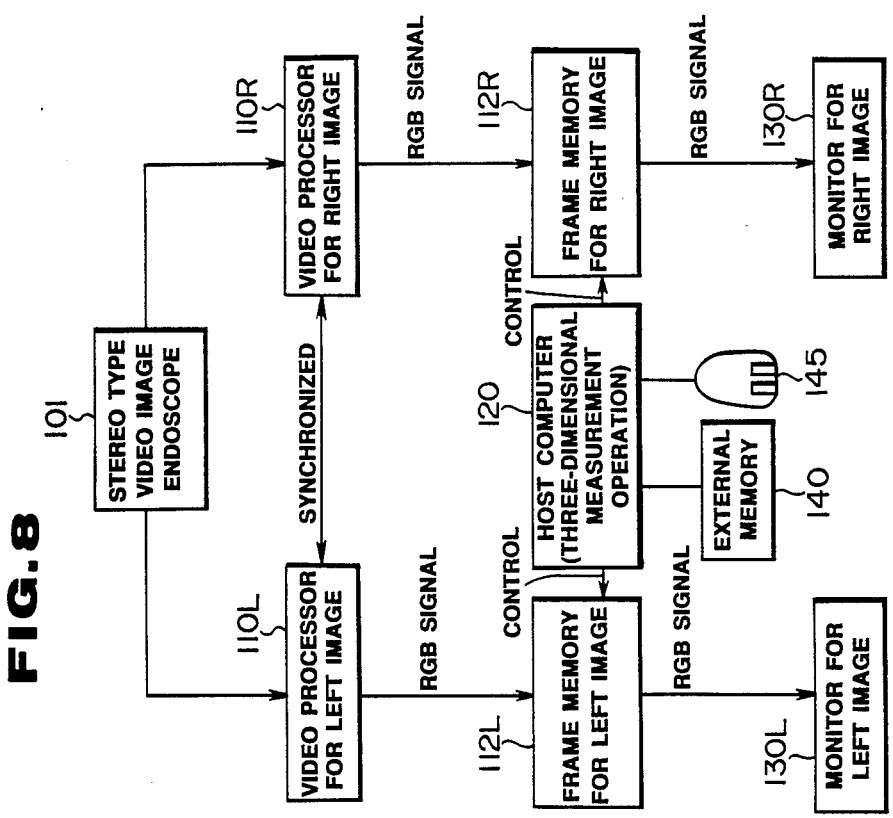

As shown in FIG. 8, the measuring endoscope apparatus of this embodiment comprises a stereo type video image endoscope (which shall be mentioned as an endoscope hereinafter) 101, a right image video processor 110R and left image video processor 110L respectively processing the image signals of a right image and left image imaged by this endoscope 101, a right image frame memory 112R and left image frame memory 112L respectively memorizing image signals, for example, by RGB signals output from the above mentioned respective video processors 110R and 110L, a right image monitor 130R and left image monitor 130L inputting image signals, for example, by RGB signals output from the above mentioned respective frame memories 112R and 112L and displaying respectively a right image and left image, a host computer 120 operating cubic measurement by using the images memorized in the above mentioned respective frame memories 112R and 112L, an external memorizing apparatus (which shall be mentioned as an external memory hereinafter) 140 connected to the above mentioned host computer and a mouse 145 connected to the above mentioned host computer 120, operating the cursors displayed in the above mentioned monitors 130R and 130L and designating the measuring object point.

The above mentioned video processors 110R and 110L process signals synchronized with each other. Also, in this embodiment, the above mentioned respective frame memories 112R and 112L are provided respectively with a plurality of sets of respective memories of R, G and B, images are memorized in one set, cursors are written into the other set and the images and cursors can be displayed on the picture of a monitor by adding together the signals written into the respective sets. The above mentioned external memory 140 can memorize the images in the frame memories 112R and 112L and can memorize a large amount of images as an image file.

Figure 9:
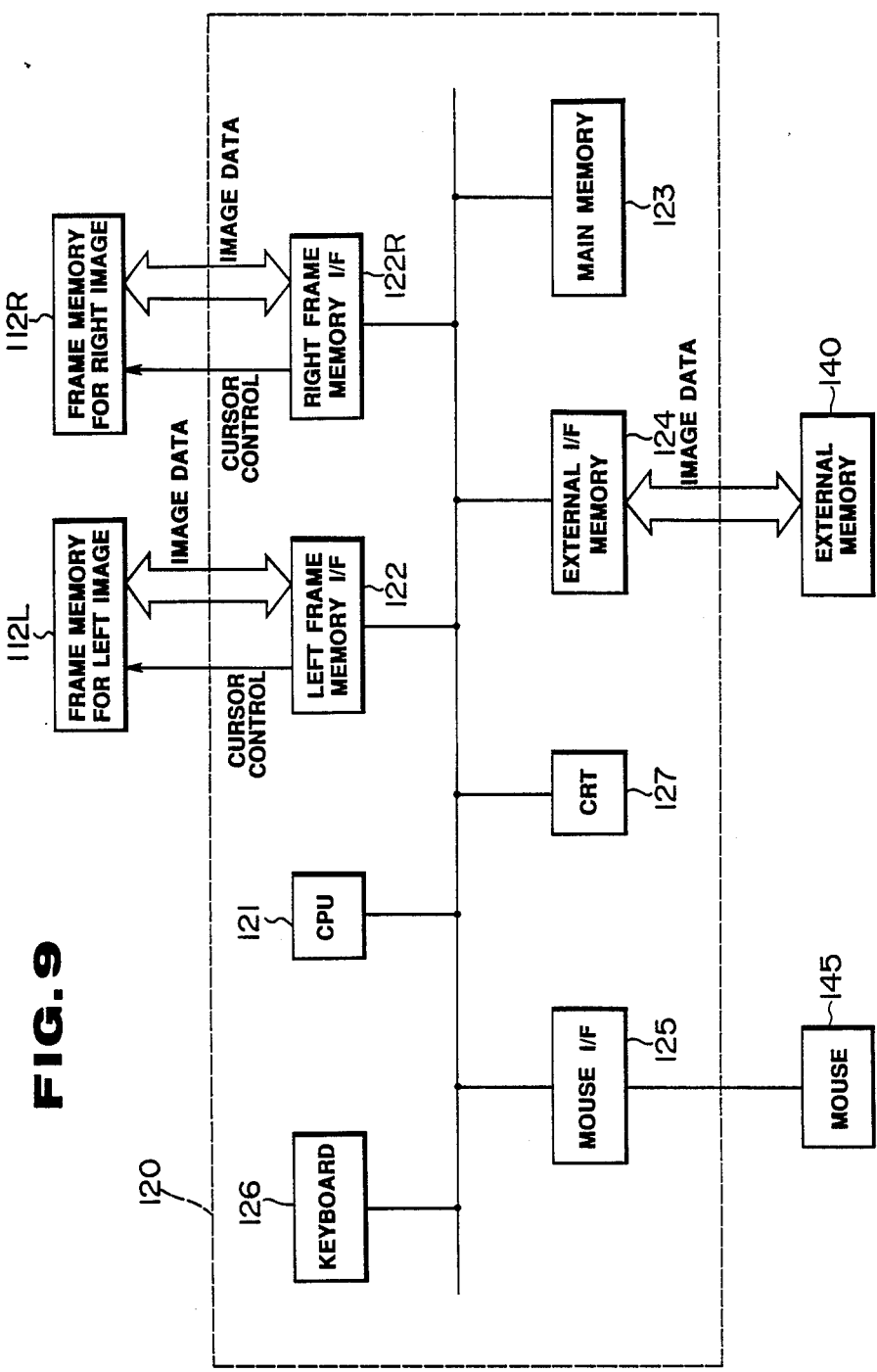

The above mentioned host computer 120 is formed as shown in FIG. 9.

That is to say, the host computer 120 comprises a CPU 121, right frame memory interface 122R, left frame memory interface 122L, main memory 123, external memory interface 124, mouse interface 125, keyboard 126 and CRT 127. The above mentioned right frame memory interface 122R and left frame memory interface 122L are connected respectively to the above mentioned right image frame memory 112R and left image frame memory L12 so that image data may be transmitted and received between them and the cursors for the above mentioned frame memories 112R and 112L may be controlled through the respective interfaces 122R and 122L. The above mentioned external memory interface 124 is connected to the external memory 140 to transmit and receive image data. The above mentioned mouse interface 125 is connected to the mouse 145.

The schematic formation of this embodiment shall be explained in the following with reference to FIGS. 6 and 7.

Figure 7:
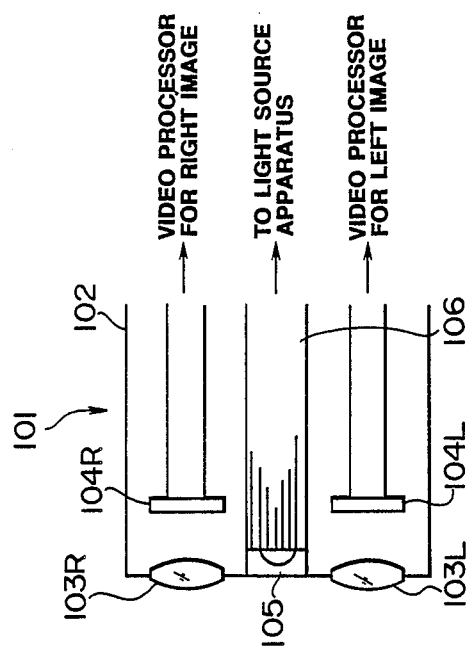

As shown in FIG. 7, the endoscope 101 is provided with an elongate insertable part 102 and a plurality of, for example, two observing windows and illuminating windows are provided in the tip part of this insertable part 102. A right eye objective lens system 103R and left eye objective lens system 103L are provided in the positions having parallaxes with each other inside the above mentioned respective observing windows. Imaging means 104R and 104L using solid state imaging devices are arranged respectively in the image forming positions of the respective objective lens systems 103R and 103L. A light distributing lens 105 is provided inside the above mentioned illuminating window. A light guide 106 consisting of a fiber bundle is provided as connected to the rear end of this light distributing lens 105. This light guide 106 is inserted through the above mentioned insertable part 102 and is connected at the entrance end to a light source apparatus not illustrated. The illuminating light output from this light source apparatus is radiated to an object through the above mentioned light guide 106 and light distributing lens 105. The light from this object is made to form a right image and left image respectively on the imaging means 104R and 104L by the above mentioned objective lens systems 103R and 103L.

The respective image signals imaged by the above mentioned imaging means 104R and 104L are input respectively into video processors 110R and 110L and are processed to be video signals. The respective image signals output from the above mentioned respective video processors 110R and 110L are converted to digital signals respectively by A/D converters 111R and 111L and are then memorized in image memories, that is, in the image memories of respective frame memories 112R and 112L.

The image signals read out of the above mentioned image memories 112R and 112L are respectively converted to analogue signals by D/A converters 158R and 158L through OR gates 157R and 157L and are input respectively into monitors 130R and 130L in which the right image and left image are respectively displayed.

A cursor displaying means 151R displaying a cursor in the right picture and a cursor displaying means 151L displaying a cursor in the left picture are provided. A mouse 145 is connected to one of the above mentioned cursor displaying means 151R and 151L through a switching means 150 so that such operation as moving the cursors for the respective pictures may be made. The cursor displaying signals output from the above mentioned cursor displaying means 151R and 151L are input respectively into the above mentioned OR gates 157R and 157L so that the cursors may be superimposed on the pictures of the monitors 130R and 130L. A guide line displaying means 153 is connected to the right picture cursor displaying means 151R so that, in case the object point is designated in the right picture, the position condition on the left picture for the object point may be operated and a guide line displaying signal may be output on the basis of the position condition. This guide line displaying signal is input into an OR gate 157L so that the guide line may be displayed as superimposed on the picture of the left image monitor 130.

An object point position calculating means 154 is connected to the above mentioned both cursor displaying means 151R and 151L so that, in case the object points are designated in both pictures, the three-dimensional coordinate of the measuring object point in the space may be determined from the coordinates in the respective pictures of the object points. Further, the above mentioned object point position calculating means 154 and right image cursor displaying means 151 are connected to an index circle displaying means 155 which outputs a signal for displaying an index circle to be a criterion of the size of the object by the three-dimensional coordinate of the above mentioned measuring object point and the position information of the object point in the right picture. This index circle displaying signal is input into an OR gate 157R so that the index circle may be displayed as superimposed on the picture of the image monitor 130R.

By the way, in this embodiment, the above mentioned switching means 150, cursor displaying means 151R and 151L, guide line displaying means 153, object point position calculating means 154 and index circle displaying means 155 are attained by operating the above mentioned host computer 120 by the later described procedure.

Before explaining the detailed operation and action of the cubic measuring system in this embodiment, first of all, the operation in the case of calculating the three-dimensional coordinate of the designated measuring object point and the operation in the case of displaying the index circle shall be schematically explained.

In the case of calculating the three-dimensional coordinate of the designated measuring object point:

(1) An image from the endoscope or an image from the image file is selected.

(2) In case the image from the endoscope is selected, the image (moving picture) is frozen (stilled) at a proper timing while being seen to fix the images on the frame memories 112R and 112L.

(3) Then, the designation of the first object point (mentioned as the point 1 hereinafter) is selected. The operations of the designation of this point 1 are as follows:

1. In case the object point is already designated, the cursors in the right and left pictures are erased.

2. A freely moving cursor (mentioned as a moving cursor hereinafter) for designating the point will appear in the right picture.

3. The mouse 145 is operated to move the moving cursor onto a point desired to be designated.

4. When the point is designated by using the mouse 145, a designating cursor will appear in the right picture. By the way, this designation can be repeated.

5. The designated point is confirmed by using the mouse 145.

6. The moving cursor in the right picture disappears and the designated cursor remains.

7. A guide line is displayed in the left picture.

8. A moving cursor appears in the left picture.

9. The mouse 145 is operated to move the moving cursor onto a point desired to be designated.

10. When the designation is made by using the mouse 145, a designated cursor will appear in the left picture. By the way, this designation can be repeated.

11. The designated point is confirmed by using the mouse 145.

12. The moving cursor in the left picture disappears and the designated cursor remains.

13. The guide line disappears.

14. The three-dimensional coordinate of the designated measuring object point is operated and output.

15. The distance from the endoscope tip to the measuring object point is operated and output. By the way, this distance is displayed, if necessary.

16. If there is any other designated measuring object point, the distance from that point will be output. By the way, this distance is displayed, if necessary.

(4) The designation of the point 2 is the same as in the above mentioned (3). In the same manner, two or more measuring object points can be designated.

On the other hand, in the case of displaying an index circle:

(5) The radius of the index circle is input.

(6) Then, by the same operations as in (3) 1 to 16 in the case of calculating the three-dimensional coordinate of the above mentioned designated measuring object point, a circle fitted point is designated. By the way, the circle fitted point is a measuring object point designated to display the index circle. The point 1 in the above mentioned (3) 1 to 16 may be re-read a circle fitted point.

(7) An index circle to be a criterion of the size is displayed on the right image on the basis of the input radius and the three-dimensional coordinate of the circle fitted point.

The detailed operation and function of the cubic measuring system in this embodiment shall be explained in the following with reference to FIGS. 16 to 25.

Figure 16:
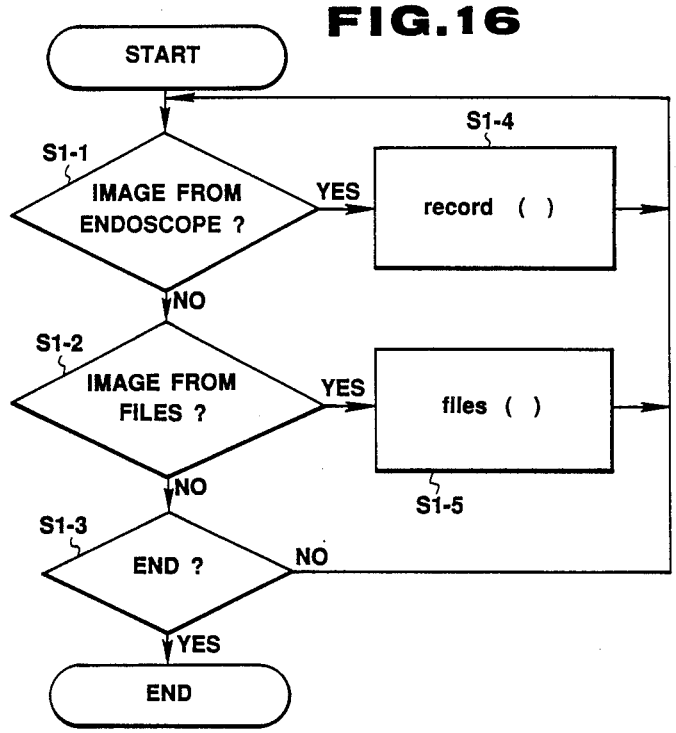
Figure 17:
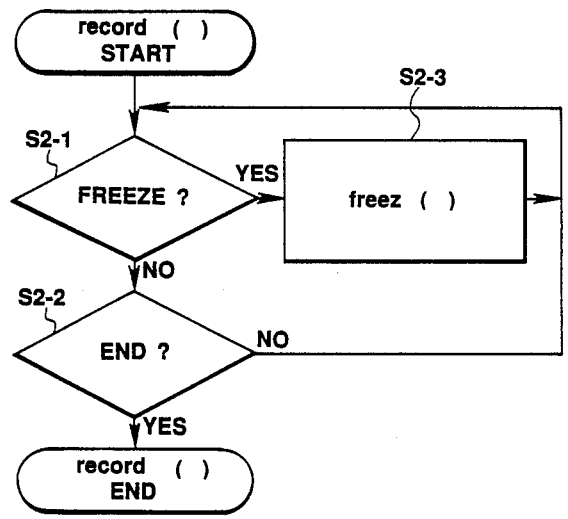
Figure 19:
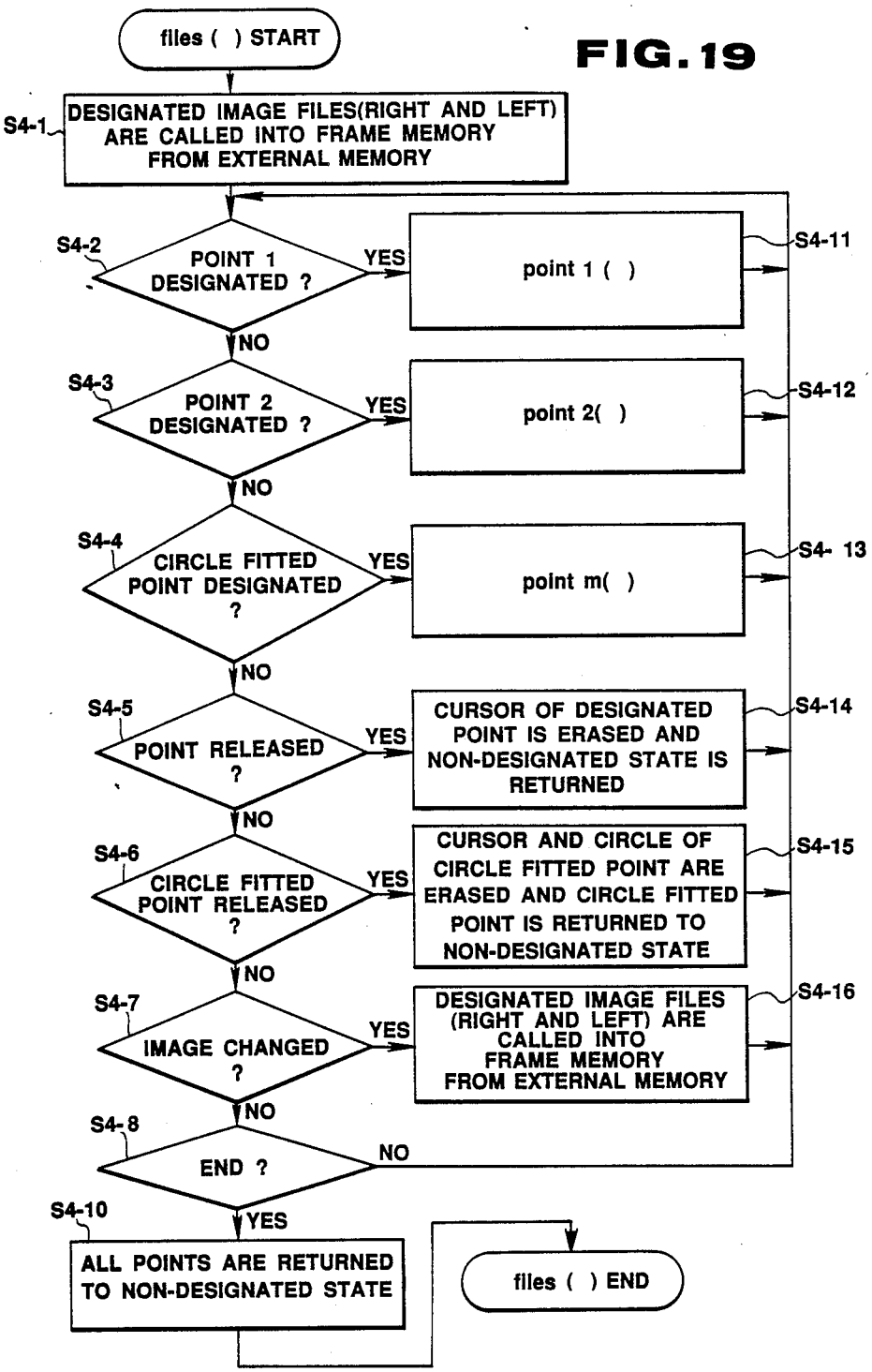

First, the main routine shall be explained by using FIG. 16. When the operation of the system is started, in a step S1-1 (hereinafter the "step" shall be omitted and merely like "S1-1" shall be mentioned), it is judged whether the image to be measured is an image from the endoscope or not. In the negative case (hereinafter the negative case shall be mentioned as "NO" and the affirmative case shall be mentioned as "YES"), in S1-2, it is judged whether the image to be measured is a image from the file or not. In the case of NO, in S1-3, it is judged whether the operation ends or not. In the case of YES, the process ends. In case it is judged in the above mentioned S1-1 to be an image from the endoscope (YES), in S1-4, a sub-routine called "record ( )" is made and the process returns to S1-1. The above mentioned record is a routine of freezing and processing the image from the endoscope. In case it is judged in the above mentioned S1-2 to be an image from the file (YES), in S1-5, a sub-routine called "file ( )" is made and the process returns to S1-1. The above mentioned file is a routine calling an image out of the external memory and making the later described various processes. Also, in the above mentioned S1-3, in the case of NO, the process returns to S1-1. By the way, the above mentioned record is shown in FIG. 17 and the above mentioned file is shown in FIG. 19. The last ( ) of the routine name represents that the routine is a sub-routine. An argument may enter ( ).

Thus, in the main routine, by such operating means not shown as a keyboard 126, the above mentioned S1-1 to S1-3 are repeated until the image from the endoscope or the image from the external memory is selected or the end of the process is indicated. By the way, the S1-1 and S1-2 may be in any order The above mentioned record shall be explained in the following by using FIG. 17.

Figure 18:
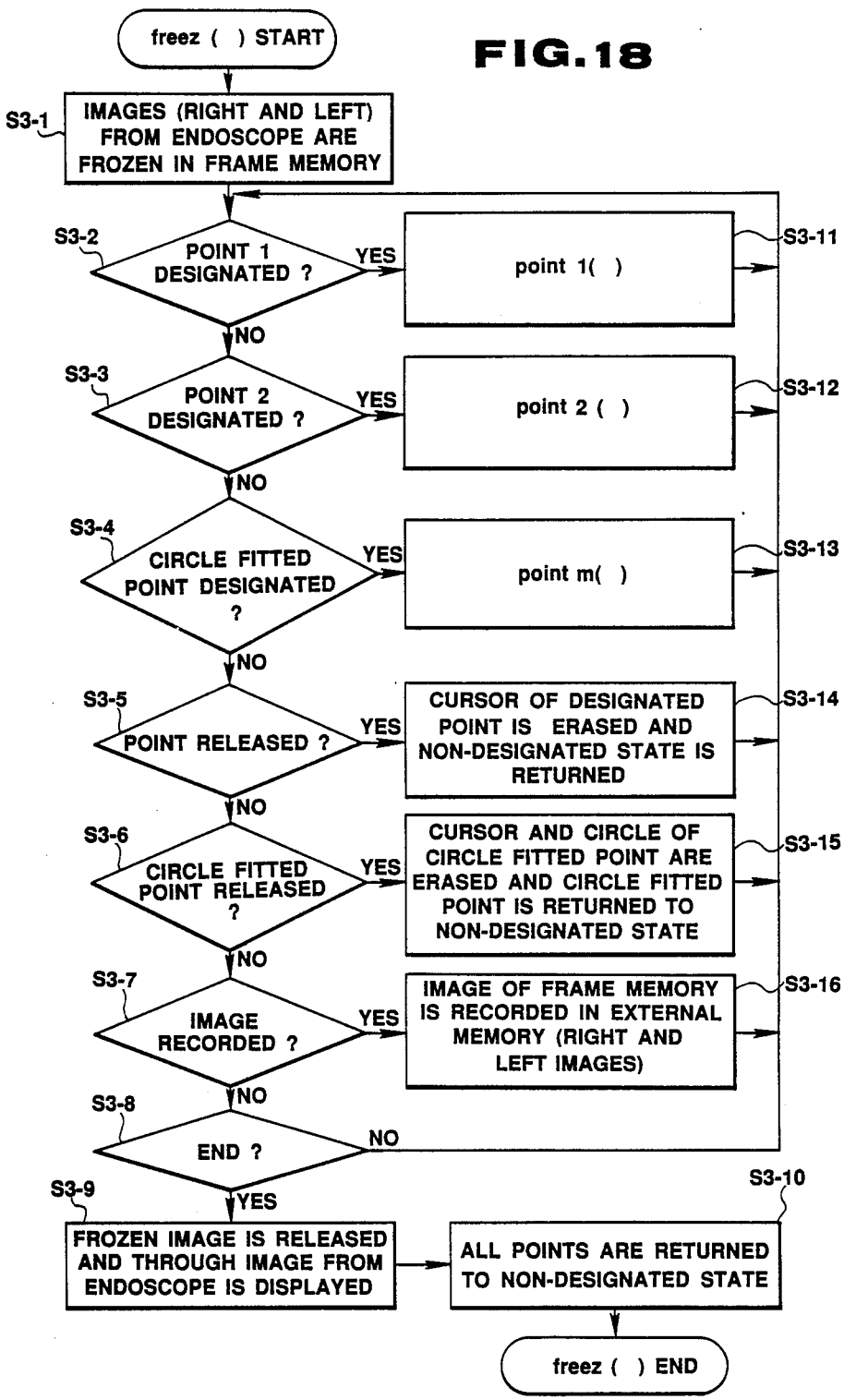

When this routine is started, first it is judged in S2-1 whether the image is to be frozen or not. That is to say, here the freezing timing is taken. In the case of NO, whether it ends or not is judged. In the case of YES, it ends. In case it is judged in the above mentioned S2-1 to be frozen (YES), in S2-3, a sub-routine called "freeze ( )" is made and the process returnes to S2-1. The above mentioned freeze is a routine of freezing the image from the endoscope and making the later described various processes. This freeze is shown in FIG. 18. Also, in the above mentioned S2-2, in the case of NO, the process returns to S2-1.

The above mentioned freeze ( ) shall be explained in the following by using FIG. 18.

When this routine is started, first, in S3-1, the respective right and left images from the endoscope are frozen in the frame memory. Then, in S3-2, it is judged whether the point 1 is designated or not. In the case of NO, in S3-3, it is judged whether the point 2 is designated or not. In the case of NO, in S3-4, it is judged whether a circle fitted point is designated or not. In the case of NO in the above mentioned S3-4, in S3-5, it is judged whether the point is released or not. In the case of NO, in S3-6, it is judged whether the circle fitted point is released or not. In the case of NO, in S3-7, it is judged whether the image is recorded or not. In the case of NO in the above mentioned S3-7, in S3-8, it is judged whether the process ends or not. In the case of YES, in S3-9, the frozen image is released and the through image from the endoscope is displayed. Then, in S3-10, all the points are returned to a non-designated state and the process ends.

In case it is judged in the above mentioned S3-2 that the point 1 is designated (YES), in S3-11, a sub-routine called "point 1 ( )" is made and the process returns to S3-2. This point 1 is a routine designating the point 1 in the right and left pictures to obtain its three-dimensional coordinate.

In case it is judged in the above mentioned S3-3 that the point 2 is designated (YES), in S3-12, a sub-routine called "point 2 ( )" is made and the process returns to S3-2. This point 2 is a routine designating the point 2 in the right and left picture to obtain its three-dimensional coordinate.

In case it is judged in the above mentioned S3-4 that the circle fitted point is designated (YES), in S3-13, a sub-routine called "point m ( )" is made and the process returns to S3-2. This point m is a routine in which the circle fitted point is designated to the right and left pictures, the same measurement as in the point 1 is made, the three-dimensional coordinate of the circle fitted point is obtained and an index (circle) varying in the size with the distance on the basis of the three-dimensional coordinate is displayed in the right and left pictures.

In case it is judged in the above mentioned S3-5 that the point is released (YES), in S3-14, the cursor of the designated point is erased, the non-designated state is returned and the process returns to S3-2.

In case it is judged in the above mentioned S3-6 that the circle fitted point is released (YES), in S3-15, the cursor of the circle fitted point and the circle are erased, the circle fitted point is returned to the non-designated state and the process returns to S3-2.

In case it is judged in the above mentioned S3-7 that the image is recorded (YES), in S-16, the right and left images of the frame memory are recorded in the external memory and then the process returns to S3-2.

Also, in the case of NO in the above mentioned S3-8, the process returns to S3-2.

Figure 20:
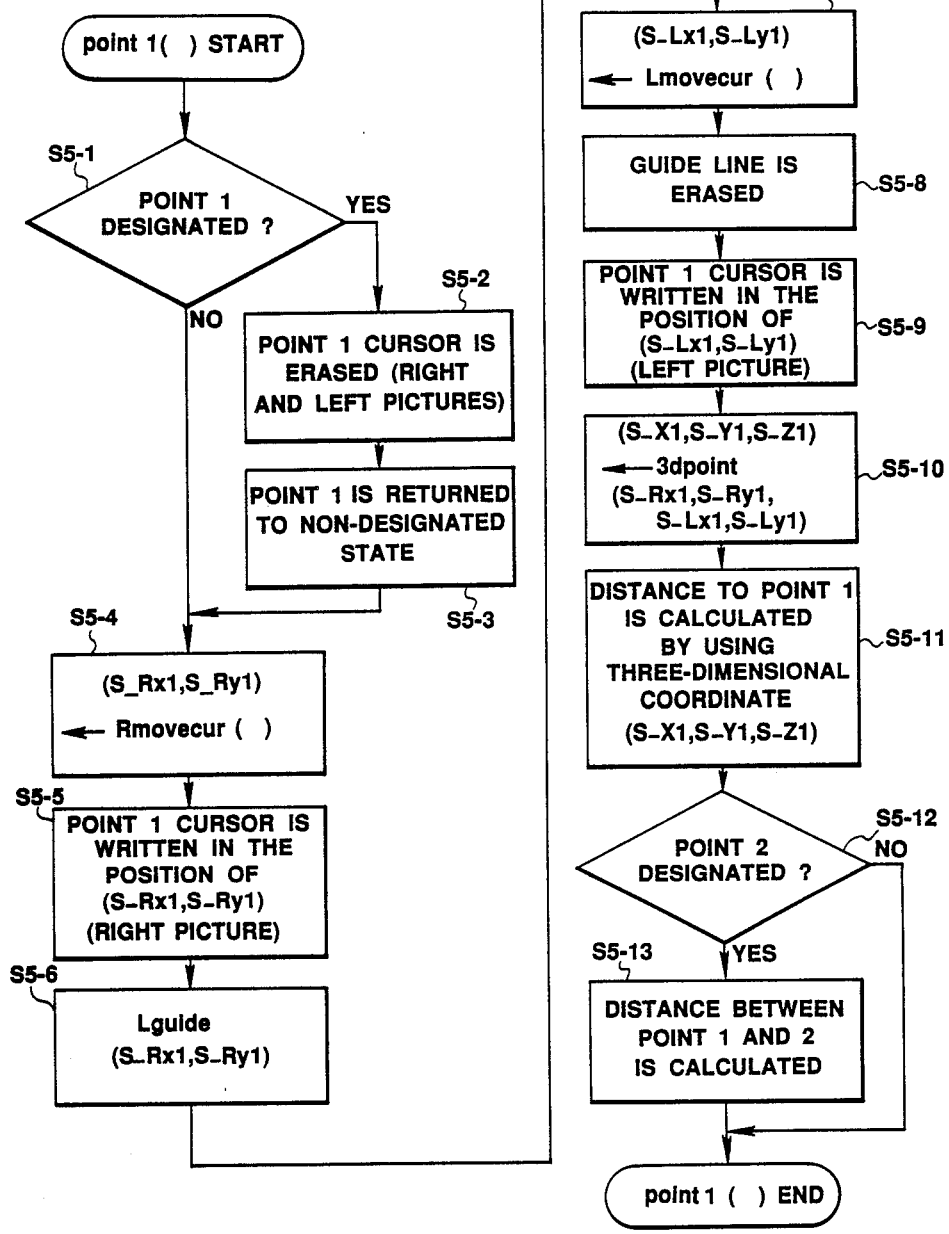
Figure 21:
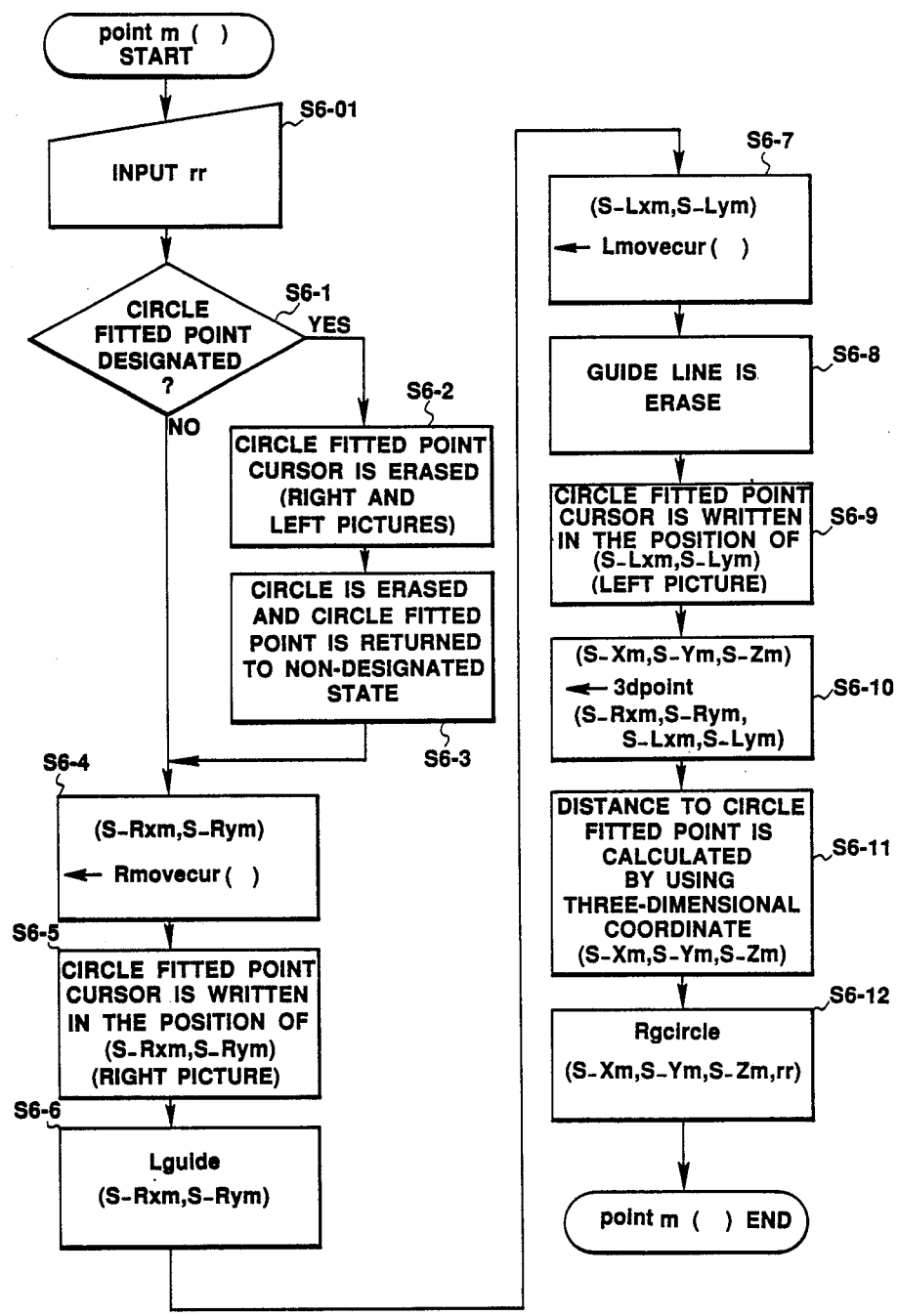

By the way, the above mentioned point1 is shown in FIG. 20 and the above mentioned pointm is shown in FIG. 21.

S3-2 to S3-7 may be in any order.

The above mentioned file ( ) shall be explained in the following by using FIG. 19.

When this routine starts, first, in S4-1, designated right and left image files are called into the frame memory from the external memory.

The next S4-2 to S4-6 are exactly the same as the S3-2 to S3-6 in the above mentioned freeze ( ). That is to say, it is judged whether the point 1 is designated or not, the point 2 is designated or not, the circle fitted point is designated or not, the point is released or not and the circle fitted point is released or not. In the case of YES in the respective steps S3-2 to S3-6, S4-11 to S4-15 which are the same as S3-11 to S3-15 in the above mentioned freeze ( ) are made and the process returns to the above mentioned S4-2.

In the case of NO in the above mentioned S4-6, in S4-7, it is judged whether the image is changed or not. In the case of NO in this S4-7, in S4-8, it is judged whether the process ends or not. In the case of YES, in S4-10, all the points are returned to the non-designated state and the process ends.

In case it is judged in the above mentioned S4-7 that the image is changed (YES), in S4-16, the designated right and left image files are called into the frame memory from the external memory and the process returns to S4-2.

Also, in the case of NO in the above mentioned S4-8, the process returns to S4-2.

By the way, S4-2 to S4-7 may be in any order.

The above mentioned point 1 ( ) shall be explained in the following by using FIG. 20.

When this routine starts, first, in S5-1, it is judged whether the point 1 is designated or not. In the case of NO, the process proceeds as it is to S5-4. In the case of YES, S5-2 and S5-3 are made and then the process proceeds to S5-4. In the above mentioned S5-2, the point 1 cursor is erased on the respective right and left pictures and then, in S5-3, the point 1 is returned to the non-designated state.

Figure 22:
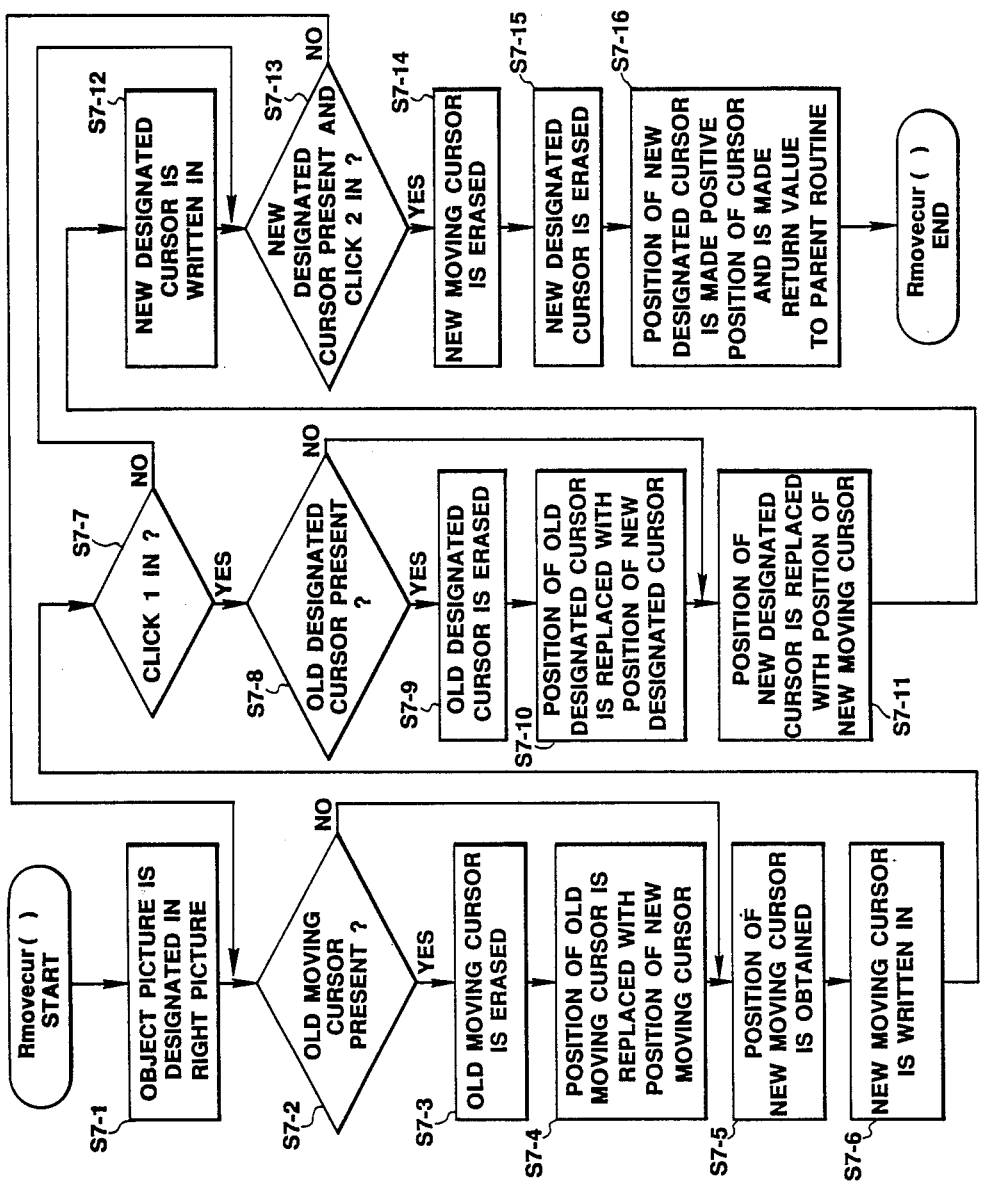

Then, in the above mentioned S5-4, a sub-routine called "Rmovecur ( )" is made. This Rmovecur is a routine designating the point in the right picture to obtain the x and y coordinates (S_Rx1, S_Ry1) of the designated point. This Rmovecur is shown in FIG. 22.

Then, in S5-5, the point 1 cursor is written in the position of (S_Rx1, S_Ry1) in the right picture.

Figure 23:
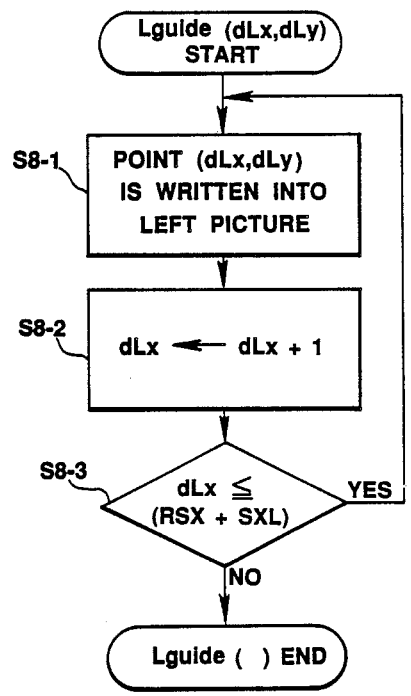

Next, in S5-6, a sub-routine called "Lguide ( )" is made. This Lguide is a routine of drawing a guide line on the left picture on the basis of the x and y coordinates (S_Rx1, S_Ry1) of the designated point in the right picture and is shown in FIG. 23.

Then, in S5-7, a sub-routine called "Lmovecur ( )" is made. This Lmovecur is a routine designating the point in the left picture to obtain the x and y coordinates (S_Lx1, S_LY1) of the designated point.

Next, in S5-8, the guide line is erased and then, in S5-9, the point 1 cursor is written in the position of (S_Lx1, S_Ly1) in the left picture.

Figure 24:
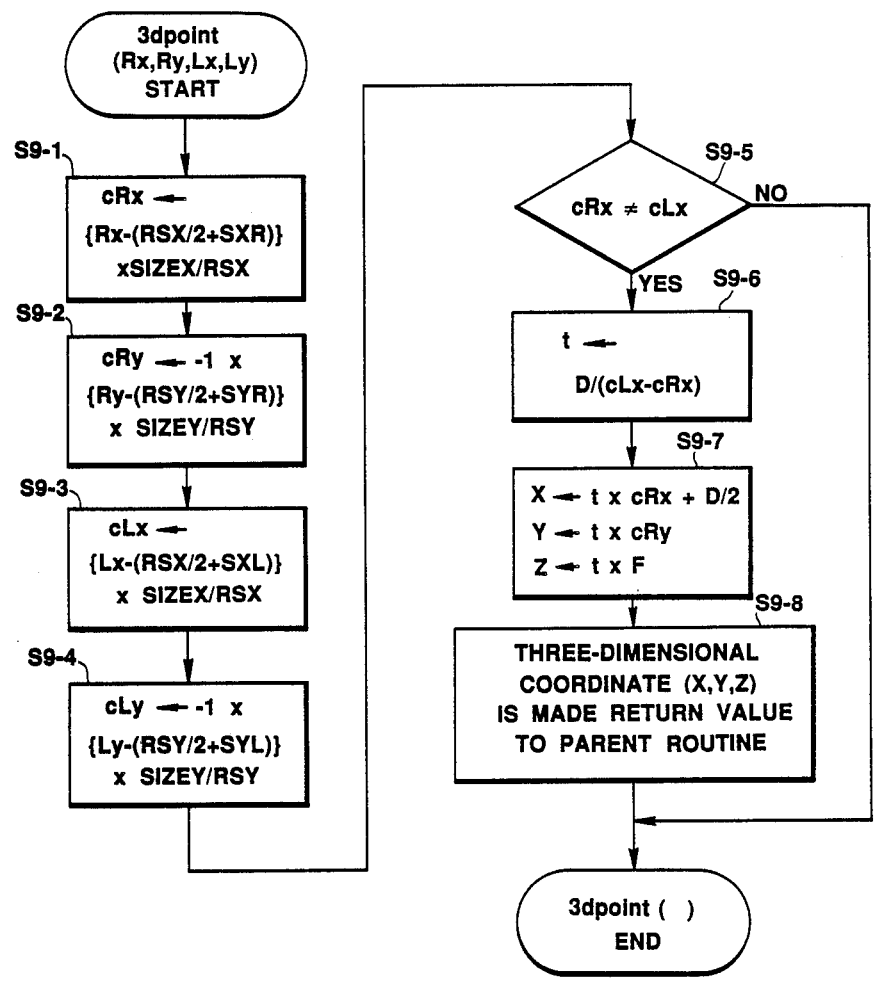

Then, in S5-10, a sub-routine called "3dpoint ( )" is made by making arguments the x and y coordinates (S_Rx1, S_Ry1, S_Lx1, S_Ly1) of the designated points in the respective right and left pictures. This 3dpoint is a routine calculating the three-dimensional coordinates of the measuring object points (points 1) corresponding to the two designated points on the basis of the designated points in the respective right and left pictures. The results are attributed to (S_x1, S_y1). This 3dpoint ( ) is shown in FIG. 24.

Next, in S5-11, the distance to the point 1 is calculated by using the above mentioned three-dimensional coordinate (S_x1, S_y1, S_z1).

Then, in S5-12, it is judged whether the point 2 is designated or not. In the case of NO, the process ends. In the case of YES, in S5-13, the distance between the points 1 and 2 is calculated and the process ends.

Thus, in the point1, first, the point 1 is designated in the right picture, thereby the guide line is displayed on the left picture and the point 1 in the left picture is designated on the guide line. By designating this point 1, the three-dimensional coordinate of the point 1 is calculated and, if the point 2 is designated, the distance between the points 1 and 2 is calculated. By the way, the three-dimensional coordinate of the above mentioned point 1 and the distance between the points 1 and 2 may be displayed as required.

By the way, the point 2 is not illustrated but is basically the same as the above mentioned point 1 ( ) and has the description (including the coordinates) relating to the points 1 and 2 replaced.

The above mentioned point m ( ) shall be exlained in the following by using FIG. 21.

When this routine starts, first, in S6-01, the radius rr of the circle is input. Then, in S6-1, it is judged whether the circle fitted point is designated or not.

Next, in S6-1, it is judged whether the circle fitted point is designated or not. In the case of NO, the process proceeds as it is to S6-4. In the case of YES, S6-2 and S6-3 are made and then the process proceeds to S6-4. In the above mentioned S6-2, the circle fitted point cursor is erased on the respective right and left pictures and then, in S6-3, the circle is erased and the circle fitted point is returned to the non-designated state.

Then, in the above mentioned S6-4, a sub-routine called "Rmovecur ( )" is made to obtain the x and y coordinates (S_Rxm, S_Rym) of the designated point in the right picture.

Next, in S6-5, the circle fitted point cursor is written in the position of (S_Rxm, S_Rym) in the right picture.

Then, in S6-6, a sub-routine called "Lguide ( )" is made and a guide line is drawn on the left picture on the basis of the x and y coordinates (S_Rxm, S_Rym) of the designated point on the right picture.

Next, in S6-7, a sub-routine called "Lmovecur ( )" is made to obtain the x and y coordinates (S_Lxm, S_Lym) in the left picture.

Then, in S6-8, the guide line is erased and then, in S6-8, the guide line is erased and then, in S6-9, the circle fitted point cursor is written in the position of (S_Lxm, S_Lym) in the left picture.

Next, in S6-10, a sub-routine called "3dpoint ( )" is made by making arguments the x and y coordinates (S_Rxm, S_Rym, S_Lxm, S_Lym) of the designated points in the respective right and left pictures, the three-dimensional coordinate of the circle fitted point is calculated and the results are attributed to (S_Xm, S_Ym, S_Zm).

Then, in S6-11, the distance to the circle fitted point is calculated by using the above mentioned three-dimensional coordinate (S_Xm, S_Ym, S_Zm)

Figure 25:
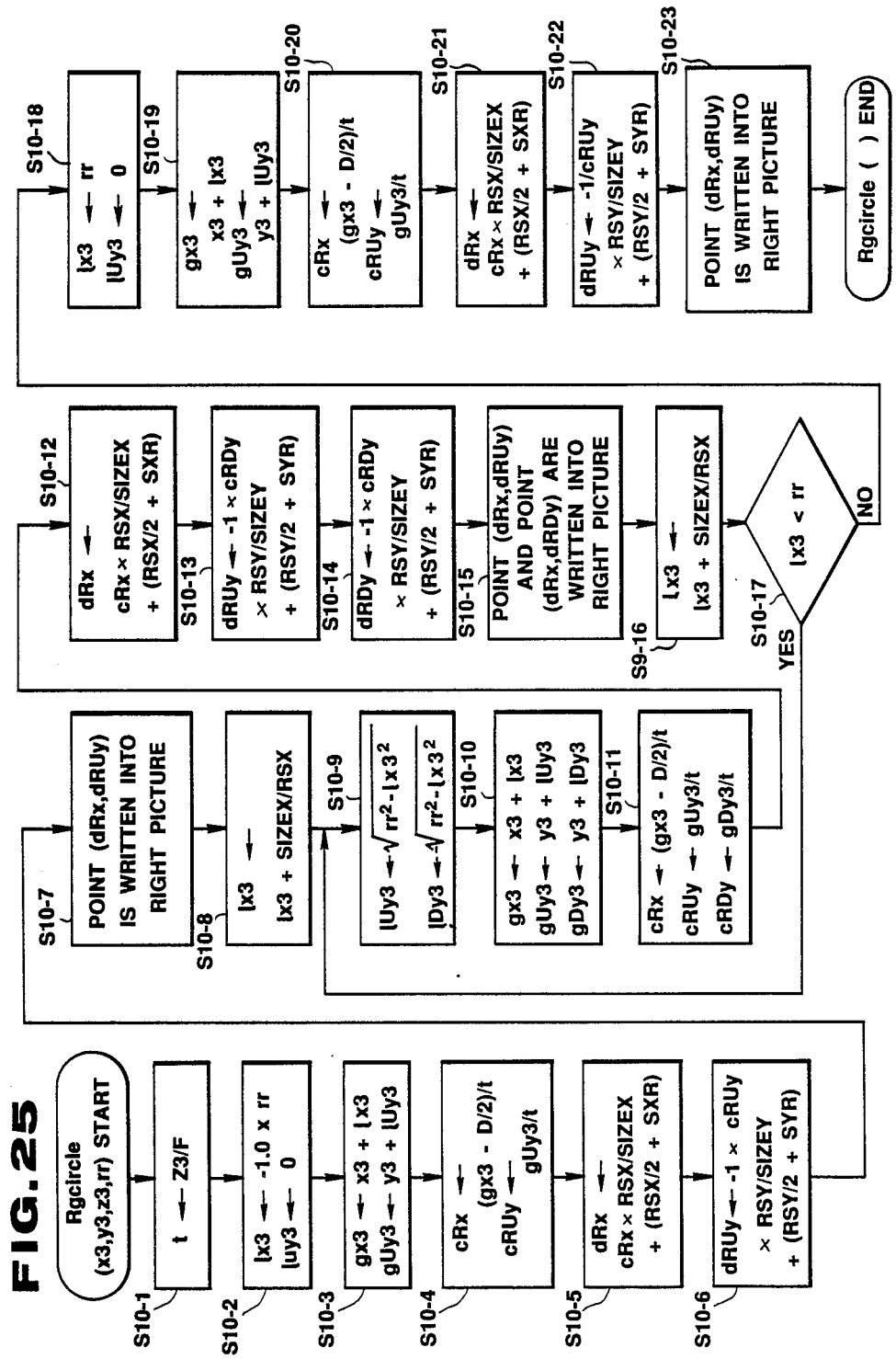

Then, in S6-12, a sub-routing called "Rgcircle )" is made and then the process ends. This Rgcircle is to write a circle to be an index around the measuring object point (circle fitted point) on the basis of the three-dimensional coordinate (S_Xm, S_Ym, S_Zm) of the circle fitted point and the radius rr and is shown in FIG. 25.

Thus, in the pointm, first, the circle fitted point is designated in the right picture, thereby a guide line is displayed in the left picture and the circle fitted point in the left picture is designated on this guide line. By the designation of this circle fitted point, the three-dimensional coordinate of the circle fitted point is calculated and an index circle to be a criterion of the size is displayed on the right image on the basis of these three-dimensional coordinate and input radius.

The above mentioned Rmovecur shall be explained in the following by using FIG. 22.

When this routine starts, first, in S7-1, the object picture is designated to be the right picture.

Then, in S7-2, it is judged whether there is an old moving cursor or not. In the case of NO, the process proceeds as it is to S7-5. In the case of YES, S7-3 and S7-4 are made and then the process proceeds to S7-2. In the case of YES in the above mentioned S7-2, in S7-3, the old moving cursor is erased and then, in S7-4, the position of a new moving cursor is substituted for the position of the old moving cursor. In the above mentioned S7-5, the position of the new moving cursor is obtained from the position information of the mouse 145 as a cursor operating means. Then, in S7-6, the new moving cursor is written in.

Thus, in S7-2 to S7-6, the erasing and writing in are made with respect to the moving cursor to move the moving cursor.

Then, in S7-7, it is judged whether the click 1 of the mouse 145 which is a designating switch is engaged or not. In the case of NO, the process proceeds as it is to S7-13. In the case of YES, the next S7-8 to S7-12 are made and then the process proceeds to S7-13. In the case of YES in the above mentioned S7-7, first, in S7-8, it is judged whether there is an old cursor or not. In the case of NO, the process proceeds as it is to S7-11. In the case of YES, S7-9 and S7-10 are made and then the process proceeds to S7-11. In the case of YES in the above mentioned S7-8, in S7-9, the old designated cursor is erased and then, in S7-10, the position of the new designated cursor is substituted for the position of the old designated cursor. In the above mentioned S7-11, the position of the new moving cursor is substituted for the position of the new designated cursor. Then, in S7-12, the new designated cursor is written in.

Thus, in S7-7 to S7-12, in case the click is engaged, the position of the moving cursor is made the designated cursor.

Next, in S7-13, it is judged whether there is the new designated cursor and the click 2 of the mouse 145 which is a confirming switch is engaged or not. In the case of NO, the process returns to the above mentioned S7-2. In the case of YES, the process proceeds to S7-14. In the case of NO in the above mentioned S7-13, the process returns to S7-2 so that the point designation may be repeated. In the above mentioned S7-14, the new moving cursor is erased and then, in S7-15, the new designated cursor is erased. Then, in S7-16, the position of the new designated cursor is made a cursor confirming position and a returning value to the parent routine and the process ends. That is to say, the obtained x and y coordinates are returned to the parent routine (such as the point1 or pointm).

Thus, in the Rmovecur, the point is designated in the right picture.

By the way, the Lmovercur ( ) is not illustrated but is basically the same as the above mentioned Rmovecur ( ) and processes the left picture instead of the right picture.

Figure 6:
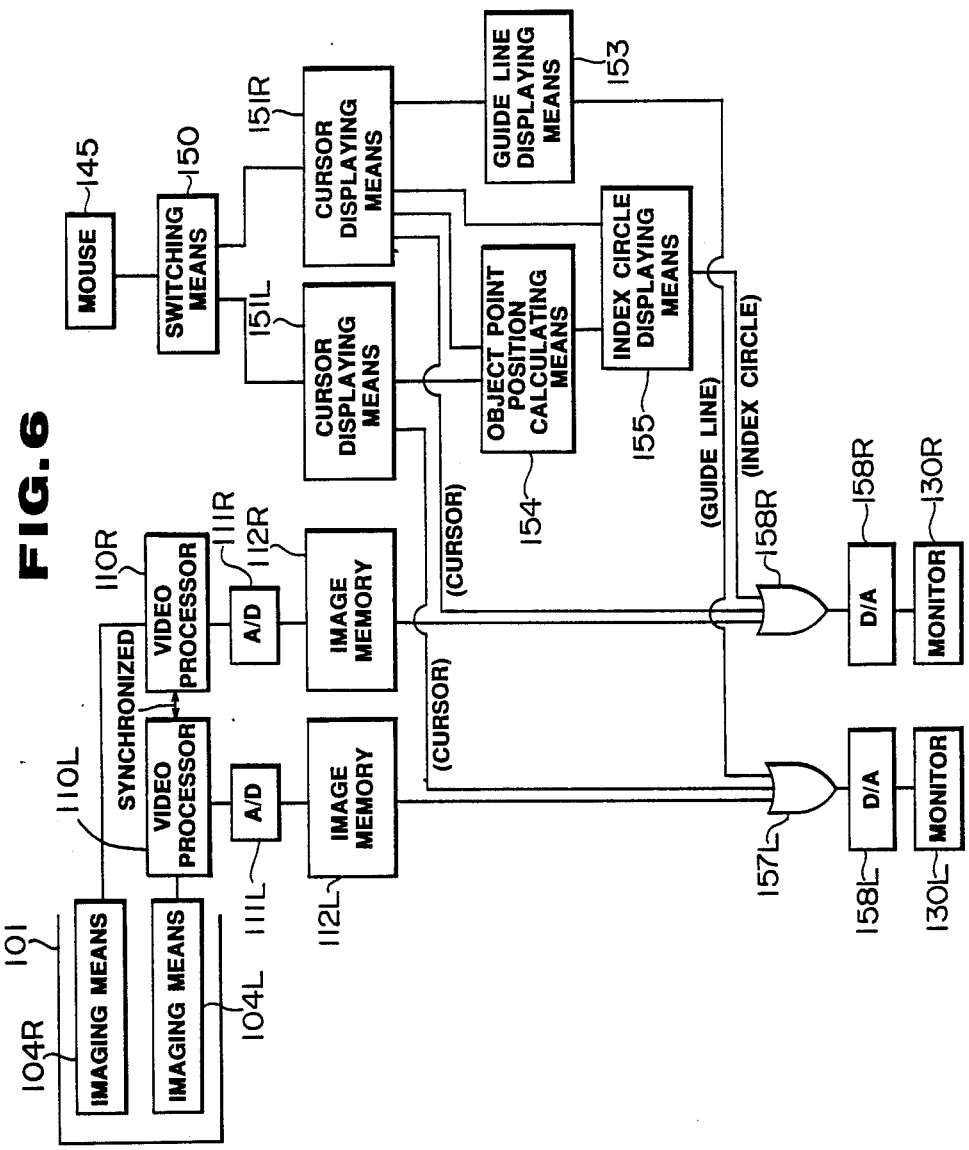
FIGS. 6 to 25 relate to the second embodidment of the present invention.

Here, the designation of the point in the right picture and the designation of the point in the left picture shall be explained as related with FIGS. 6 and 9. The mouse 145 which is a cursor operating means is operatively connected with a right picture cursor displaying means 151R (which is realized also by the Rmovecur) by the Rmovecur realizing a switching means 150. At this time, first, a cursor for designating the point is displayed in the right picture. When the point designation in the right picture is secured, the cursor for the point designation is erased from the right picture. Then, the above mentioned mouse 145 is released from the connection with the above mentioned cursor displaying means 151R and is operatively connected with a left picture cursor displaying means 151L (which is realized also by the Lmovecur) by the Lmovecur realizing the switching means 150. At this time, first, a cursor for designating the point is displayed in the left picture. When the point designationi in the left picture is secured, the cursor for the point designation is erased from the left picture.

"The object picture is designated to be the right picture" in the first step of the Rmovecur (the Lmovecur is also the same) corresponds to the switching means 150 in FIG. 6. This operation shall be explained in FIG. 9. The mouse position information from the mouse interface 125 is always taken into the CPU 121. By the above mentioned step "designating to the right picture", the CPU 121 transmits this mouse position information to the right image frame memory 112R through the right frame memory interface 122R to control the cursor. By the right image frame memory 112R, the cursor is superimposed with the image.

The Lmovecur has also the step of "designating the object picture to the left picture" in the first step. When this Lmovecur is entered, the position information of the mouse 145 is transmitted to the left frame memory interface 122L.

Thus, by the flow of the CPU 121, one mouse 145 moves the cursor on the right picture or left picture and is switched. That is to say, the CPU 121 is provided with a function of operatively connecting the mouse 145 selectively with the right image frame memory 112R and left image frame memory 112L. This switching is made under the following conditions.

First of all, in the first step of the Rmovecur, the mouse 145 is connected to the right image frame memory 112R and, in the judging step of "whether there is a new designated cursor and the click 2 is engaged or not", until the click 2 is confirmed, the mouse 145 moves round the loops of S7-2 to S7-13. When the click 2 is engaged, the Rmovecur ends, the point 1 cursor is written in the position of (S_Rx1, S_Ry1 ) (in the case of the point1), the Lguide is made and then (S_Lx1, S_Ly1) Lmovecur is made. In the first step of this Lmovecur, the mouse 145 is connected to the left image frame memory 112L.

Thus, the image with which the mouse 145 is operatively connected is switched by the engagement of the click 2.

Figure 10:
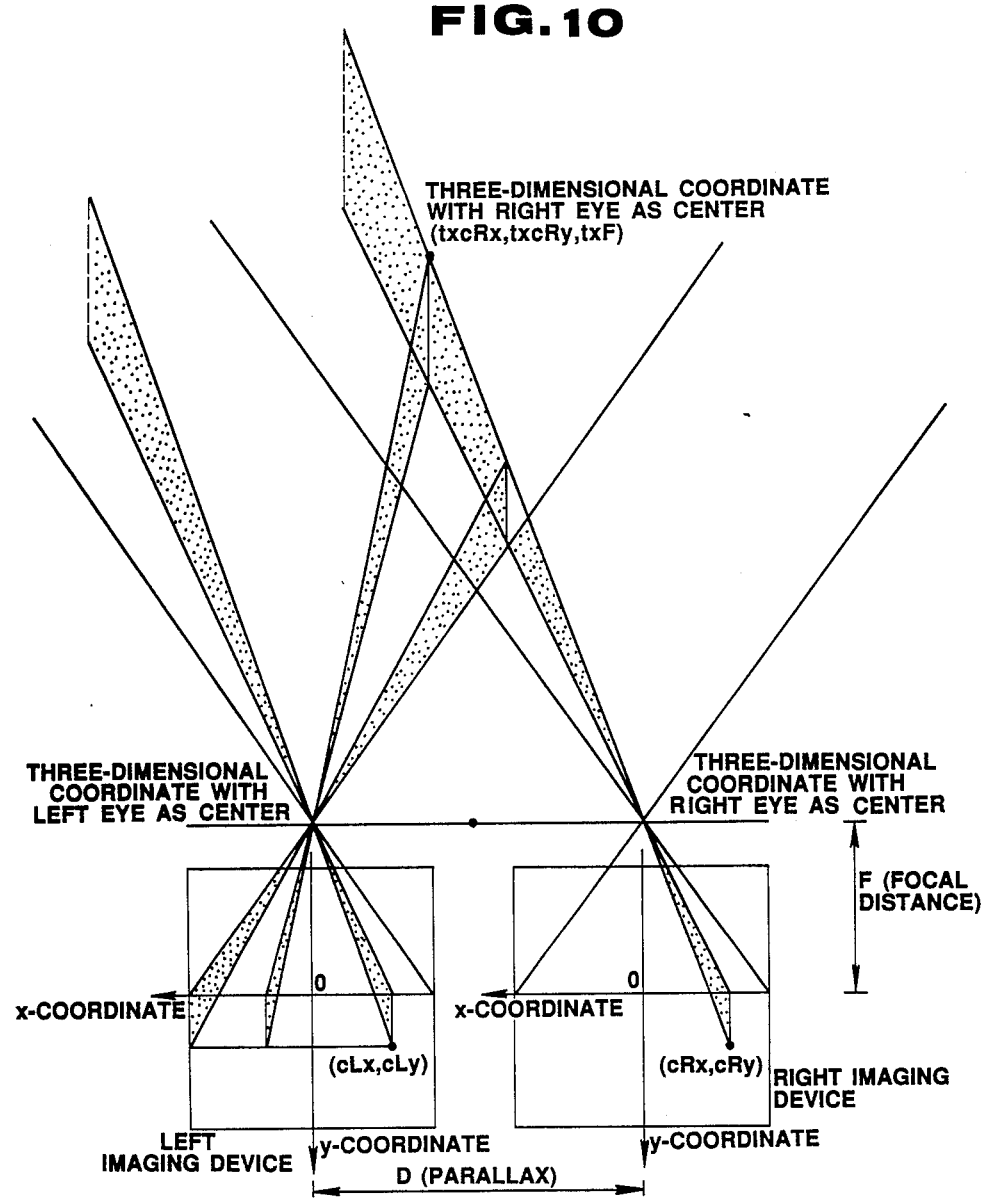

Before explaining the above mentioned L guide ( ), the principle of the method of determining the guide line shall be explained in the following with reference to FIG. 10. By the way, the guide line is a line representing the position in which, in case an object point is designated on one picture, the object point should be on the other picture.

When the x and Y coordinates of the designated point on the right imaging device are (cRx, cRy), from the spatial position relation (similarity), the three-dimensional coordinate of the measuring object point is represented by a right eye center three-dimensional coordinate:

$$(t \times cRx, t \times cRy, t \times F).$$

wherein t is a parameter and F is a focal distance of the objective lens system. The right eye center three-dimensional coordinate is a three-dimensional coordinate having the center of the right image forming means as the origin. The x direction of the three-dimensional coordinate is the direction passing through the centers of both right and left image forming means, the z direction is the direction vertical to the tip surface of the endoscope and the y direction is the direction intersecting at right angles with either of the x direction and z direction.

The three-dimensional coordinate of the above mentioned measuring object point is represented by a left eye center three-dimensional coordinate as $$(t \times cRx + D, t \times cRY, t \times F)$$

wherein D represents a parallax.

When this coordinate is divided by t so as to be represented by the x and y coordinates on the left imaging device, it will be (cRx+D/t, cRy). As the extreme left end of the guide line displayed in the left picture is the position when the measuring object point is infinitely far, if t→∞, the x and y coordinates (cLx, cLy) at the extreme left end of the guide line will become (cLx, cLy)=(cRx, cRy). Also, as the measuring object point is approached, the x coordinate on the left imaging device will become larger but the y coordinate will not vary. Therefore, the guide line will become a fixed straight line in the y coordinate from the above mentioned (cLx, cly)=(cRx, cRy) to the extreme right end of the left imaging device.

By the way, the above explanation is of the case that the distortion aberration of the objective lens system of the endoscope is neglected. Thus, in case the distortion aberration is not corrected, the extreme left end of the guide line can be calculated by using the x and y coordinates on the picture instead of the x and y coordinates on the imaging device. The x and y coordinates at the extreme left end of the guide line of the left picture are equal to the x and y coordinates of the designated point of the right picture. That is to say, if the x and y coordinates of the designated point on the right picture are (Rx, RY), the x and Y coordinates (dLx, dLy) at the extreme right end of the guide line on the left picture will be (dLx, dLZY)=(Rx, Ry).

The Lguide ( ) drawing the guide line by using the above principle shall be explained by using FIG. 23.

In this routine, the x and y coordinates (dLx, dLy) of the designated point of the right picture delivered from the parent routine (point1 or pointm) are made arguments.

When this routine starts, first, in S8-1, the point (dLx, dLy) is written into the left picture.

Then, in S8-2, dLx is increased by 1.

Figure 13A:
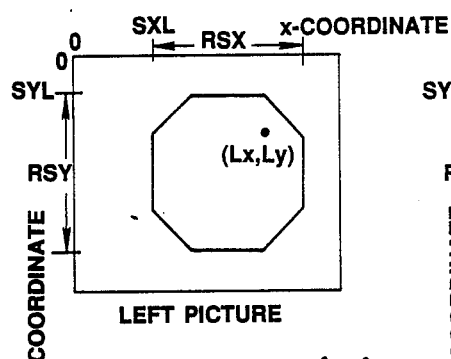
Figure 13B:
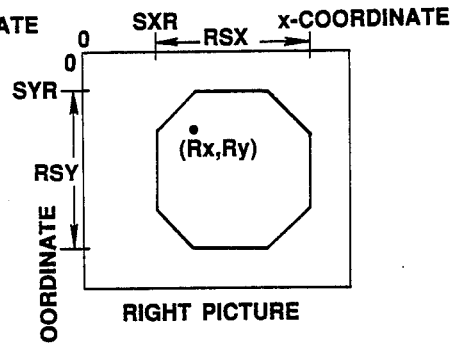

Next, in S8-3, dLx≦(RSX+SXL) is judged. By the way, as shown in FIG. 13(a), the above mentioned RSX is a number of pixels in the x direction of the part in which the endoscope is displayed on the left picture and SLX is an x coordinate of the pixel at the extreme left end of the part in which the endoscope is displayed on the left picture. That is to say, in S8-3, it is judged whether dLx has reached the extreme right end or not. In case it has not reached (YES), the process returns to the above mentioned S8-1. In case dLx has reached the extreme right end (NO), the process ends.

Figure 14:
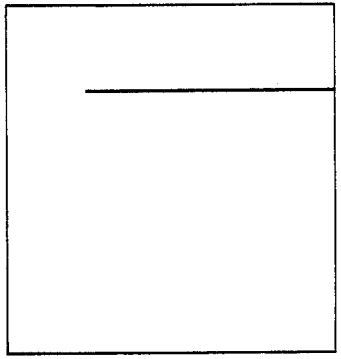

Thus, the guide line is drawn from the same coordinate point as the designated point in the right picture to the extreme right end of the picture. An example of the left picture in which the guide line is thus drawn is shown in FIG. 14.

By the way, this Lguide realizes a guide line displaying means 153 in FIG. 6.

Figure 11:
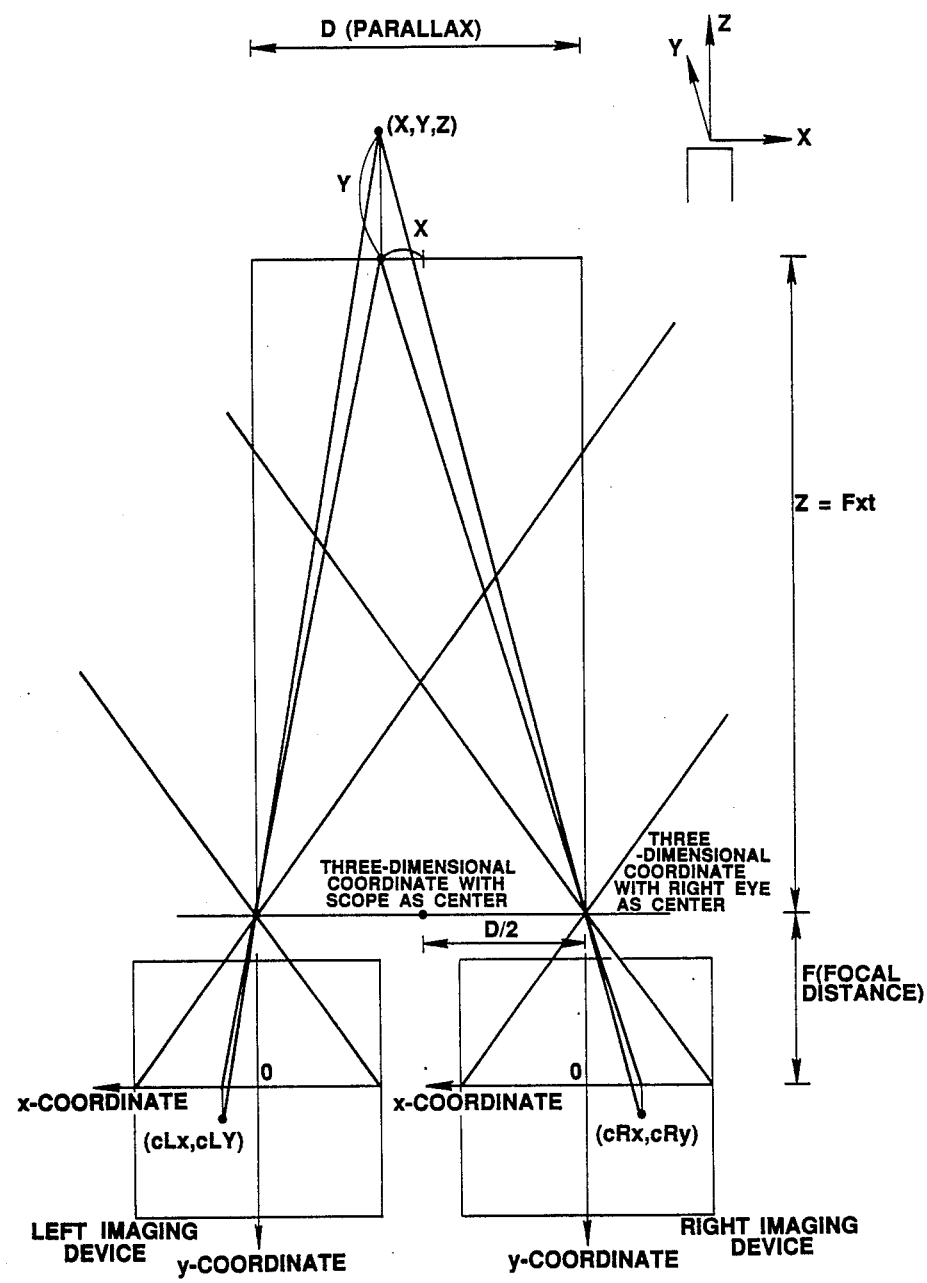

Now, before explaining the above mentioned 3dpoint ( ), the principle of the method of determining the three-dimensional coordinate of the measuring object point shall be explained in the following with reference to FIGS. 11 and 13.

The x and y coordinates of the designated point on the right imaging device shall be represented by (cRx, cRy), the x and y coordinates of the designated point on the left imaging device shall be represented by (cLx, cLY) and the three-dimensiional coordinate of the measuring object point shall be reprssented by (X, Y, Z).

From the spatial position relation (similarity), by using a parameter t, the right eye center three-dimensional coordinate of the measuring object point is represented by $$X' = t \times cRx,$$

$$Y' = t \times cRy,$$

$$Z' = t \times F.$$

By the way, from the spatial position relation (similarity), the parameter t is $$t = D/(cLx - cRx).$$

When the above mentioned right eye center three-dimensional coordinate is converted to a scope center three-dimensional coordinate, $$X = X' + D/2 = t \times cRx + D/2,$$

$$Y = Y' = t \times cRy,$$

$$Z = Z' = t \times F.$$

By the way, the above mentioned scope center three-dimensional coordinate is a three-dimensional coordinate having the intermediate point of the respective centers of the right and left image forming means as the original.

Also, in case two measuring object points are designated, the distance between the two points can be determined from the three-dimensional coordinates of these two points. That is to say, if the three-dimensional coordinates of the two points are $(X_1, Y_1, Z_1)$ and $(X_2, Y_2, Z_2)$, the distance d between the two points will be given by the following formula:

$$d = [(X_1 - X_2)^2 + (Y_1 - Y_2)^2 + (Z_1 - Z_2)^2]^{\frac{1}{2}}.$$

Now, as the designated points are designated in the positions on the respective right aned left pictures, in order to make the above mentioned operation, it is necessary to convert the positions on the pictures to positions on the imaging devices.

Therefore, the conversion of the positions on the pictures to the positions on the imaging devices shall be explained by using FIG. 13.

As shown in FIGS. 13(a) and (b), the origins of the x and y coordinates of the respective right and left pictures shall be in the left upper parts of the pictures, the number of pixels in the x direction of the part in which the endoscope image is displayed on each of the respective right and left pictures shall be RSX, the number of pixels in the y direction shall be RSY, the x coordinate of the pixel at the extreme left end of the part in which the endoscope image is displayed in the left picture shall be SXL, the y coordinate of the pixel at the uppermost end shall be SYL, the x coordinate of the pixel at the extreme left end of the part in which the endoscope image is displayed in the right picture shall be SXR and the y coordinate of the pixel at the uppermost end shall be SYR.

Figure 13C:
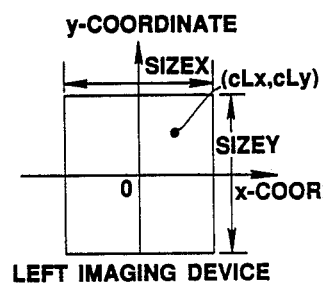
Figure 13D:
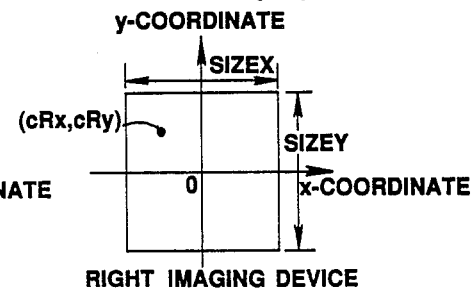

Also, as shown in FIGS. 13(c) and (d), the origins of the x and y coordinates of the respective right and left imaging devices shall be the centers of the imaging devices, the length in the x direction of each imaging device shall be SIZEX and the length in the Y direction shall be SIZEY.

Also, the x and y coordinates of the designated point in the left picture shall be (Lx, Ly), the x and y coordinates of the designated point in the left imaging device shall be (cLx, cLy) and the x and y coordinates of the designated point in the right imaging device shall be (cRx, cRy).

The relation between (Lx, Ly) and (cLx, cLy) is represented by the following formulae:

$$cLx = \{Lx-(RSX/2+SXL)\} \times SIZEX/RSX$$

$$cLy = -1 \times \{Ly-(RSY/2+SYL)\} \times SIZEY/RSY.$$

In the same manner, the relations between (Rx, Ry) and (cRx, cRy) are represented by the following formulae:

$$cRx = [Rx-(RSX/2+SXR)] \times SIZEX/RSX.$$

$$cRy = -1 \times \{Ry-(RSY/2+SYR)\} \times SIZEY/RSY.$$

The above mentioned 3dpoint ( ) using such coordinate conversion as in the above and the principle of the method of determining the three-dimensional coordinate shall be explained by using FIG. 24.

In this routine, the x and y coordinates (Rx, Ry) of the designated point of the right picture and the x and y coordinate (Lx, Ly) of the designated point of the left picture delivered from the parent routine (point1 or pointm) are made arguments.

When this routine starts, first, in S9-1, $\{Rx-(RSX/2+SXR)\} \times SIZEX/RSX$ is operated and this is made an x coordinate cRx on the imaging device of the right designated point.

Then, in S9-2, $-1 \times \{RY-(RSY/2+SYR)\} \times SIZEY/RSY$ is operated and this is made a y coordinate cRy on the imaging device of the right designated point.

Then, in S9-3, $\{Lx-(RSX/2+SXL)\} \times SIZEX/RSX$ is operated and this is made an x coordinate cLx on the imaging device of the designated point.

Next, in S9-4, $-1 \times \{Ly-(RSY/2+SYL)\} \times SIZEY/RSY$ is operated and is made a y coordinate cLy on the imaging device of the left designated point.

That is to say, in the above mentioned S9-1 to S9-4, the position on the picture is converted to the position on the imaging device on the basis of the above mentioned converting formula.

Then, in S9-5, cRx≠cL is judged. In the case of NO, that is to say, in the case of cRx=cL, the measuring object point is infinitely far. In this case, the process ends. On the other hand, in the case of YES, in S9-6, D/(cLx−cRx) is operated to make the parameter t.

Then, in S9-7, $t \times cRx+D/2$ is made X, $t \times cRY$ is made Y and $t \times F$ is made Z to determine the three-dimensional coordinate of the measured object point.

Next, in S9-8, the above mentioned three-dimensional coordinate (X, Y, Z) is made a retuning value to the parent routine and the process ends.

By the way, this 3dpoint realizes the object position calculating means 154 in FIG. 6.

Figure 12:
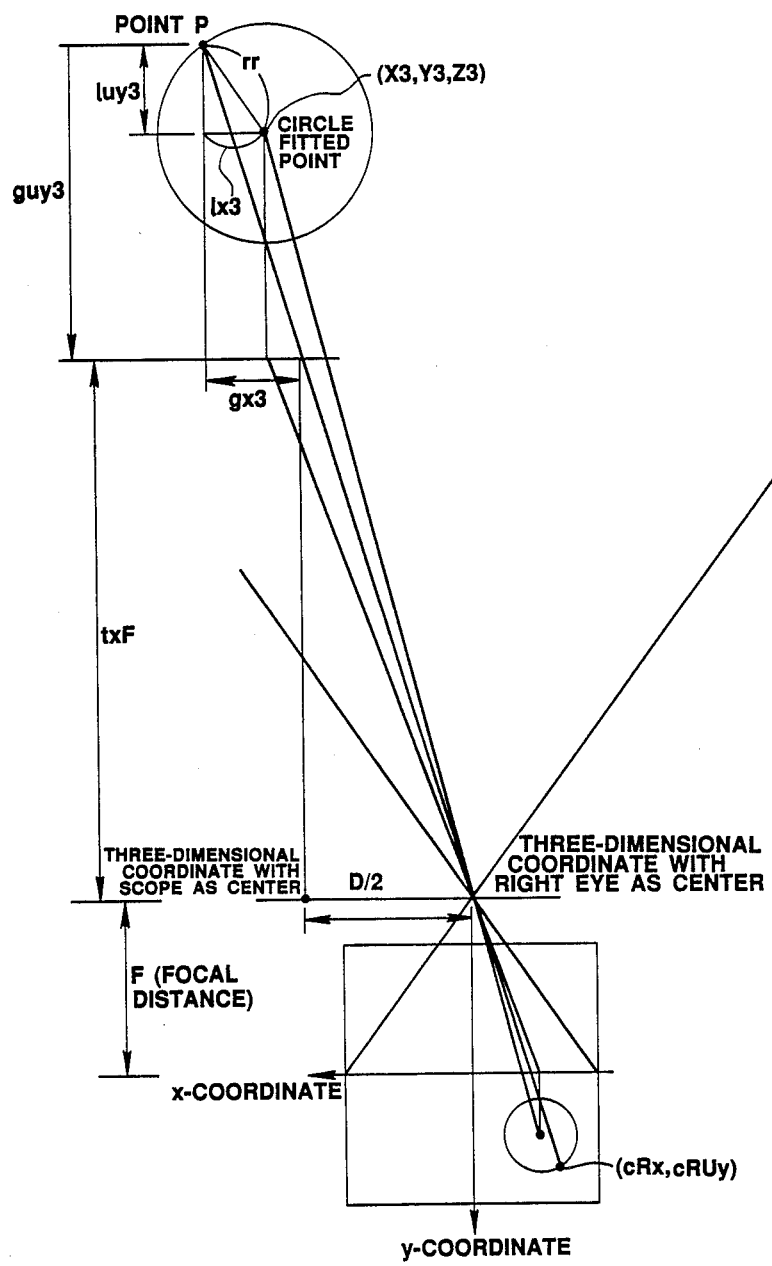

Now, before explaining the above mentioned Rgcircle ( ), the principle of the method of determining the index circle shall be explained in the following with reference to FIG. 12.

When the three-dimensional coordinate of the circle fitted point is made (X3, Y3, Z3) and the three-dimensional coordinate of the point in the coordinate system having the circle fitted point as a center is made (lx 3, lUy3, Z3), the scope center three-dimensional coordinate will be (gx3, gUy3, z3)

$$=(lx\ 3+X3, lUy3+Y3, Z3).$$

This scope center three-dimensional coordinate is converted to a right eye center three-dimensional coordinatae, is divided by the paramether t and is converted to x and y coordinates (cRx, cRUY) on the right imaging device to be $$(cRx, cRUy) = ((gx3-D/2)/t, gUy3/t).$$

The parameter t is represented as t=Z3/F by using Z of the three-dimensional coordinate of the circle fitted point.

If the above mentioned point P is moved under the condition as a point of a distance rr from the circle fitted point, an index circle will be described on the imaging device in response to it.

Also, an index circle is described on the picture by converting the x and y coordinates on the above mentioned imaging device to x and y coordinates on the picture.

The above mentioned Rgcicle ( ) using such principle as in the above shall be explained by using FIG. 25.

In this routine, the three-dimensional coordinate (x3, y3, z3) and the radius rr of the circle delivered from the parent routine (pointm) are made arguments.

When this routine starts, first, in S10-1, z3/F is made a parameter t.

Then, in S10-2, $-1.0 \times rr$ is made lx3 and 0 is made ly3 That is to say, the x and y coordinates having as a center the circle fitted point of the point at the left end of the index circle.

Then, in S10-3, x3+lx3 is made gx3 and y3+lUy3 is made gUy3. That is to say, the coordinate of the point at the above mentioned left end is converted to the scope center coordinate.

Next, in S10-4, (gx3−D/2)/t is made cRx and gUY3/t is made cRUY. That is to say, the point at the above mentioned left end is converted to the point on the right imaging device.

Then, in S10-5, $cRx \times RSX/SIZEX+(RSX/2+SXR)$ is operated and is made an x coordinate dRx on the right picture.

Next, in S10-6, $-1 \times cRUY \times RSY/SIZEY+(-RSY/2+SYR)$ is operated and is made a y coordinate dRUy on the right picture.

As explained with reference to FIG. 13, the above mentioned S10-5 and S10-6 are to convert the position on the imaging device to the position on the picture.

Then, in S10-7, the point (dRx, dRUy) is written into the right picture.

Thus, in S10-2 to S10-7, the point at the left end of the index circle is written in the right picture.

Next, in S10-8, lx3+SIZEX/RSX is made lx3. That is to say, the x coordinate of the point on the index circle is moved to the right.

Then, in S10-9, $(rr^2-lx3^2)^{\frac{1}{2}}$ is made the y coordinate lUy3 of the point on the upper side on the index circle corresponding to the above mentioned lx3 and $-(rr^2-lx3^2)^{\frac{1}{2}}$ is made the y coordinate lDy3 of the point on the lower side on the index circle corresponding to the above mentioned lx3.

Then, in S10-10, x3+lx3 is made gx3, y3+lUy3 is made gUy3 and y3+lDy3 is made gDy3. That is to say, the coordinates of the two points on the above mentioned index circle are converted to scope center coordinates.

Then, in S10-11, (gx3−D/2)/t is made cRx, gUy3/t is made cRUy and gDy3/t is made cRDy. That is to say, the two points on the above mentioned index circle are converted to points on the right imaging device.

Then, in S10-12, cRx×RSX/SIZEX+(RSX/2+SXR) is made dR.

Next, in S10-13, −1×cRUy×RSY/SIZEY+(-RSY/2+SYR) is made RUy.

Then in S10-14, −1×cRDy×RSY/SIZEY+(RSY/2+SYR) is made dRDy.

That is to say, in the above mentioned S10-12 to S10-14, the position on the imaging device is converted to the position on the picture.

Next, in S10-15, the point (dRx, dRUy) and point (dRx, dRDy) are written into the right picture.

Then, in S10-16, lx3+SIZEX/RSX is made lx3. That is to say, the x coordinate of the point on the index circle is moved to the right.

Then, in S10-17, lx3<rr is judged. In the case of YES, that is, in case the point on the index circle has not reached the right end, the process returns to the above mentioned S10-9. On the other hand, in the case of NO, that is, in case the point on the index circle has reached the right end, the process proceeds to the next S10-18. Thus, until the point on the index circle reaches the right end, the two points on the index circle are written into the picture in the order from the left side.

Next, in the above mentioned S10-18, rr is made lx3 and 0 is made lUy3. That is to say, the x and y coordinates having as a center the circle fitted point of the point at the right end of the index circle are determined.

Then, S10-19 to S10-23 are made and the process ends. The above mentioned S10-19 to S10-23 are the same as the above mentioned S10-3 to S10-7. That is to say, in S10-19, the coordinate of the point at the right end is converted to the scope center coordinate, in S10-20, the point at the right end is converted to the point on the right imaging device, in S10-21 and S10-22, the position on the imaging device is converted to the position on the picture and, in S10-23, the point (dRx, dRUy) is written into the right picture.

Thus, in S10-18 to S10-23, the point at the right end of the index circle is written in the right picture.

Figure 15:
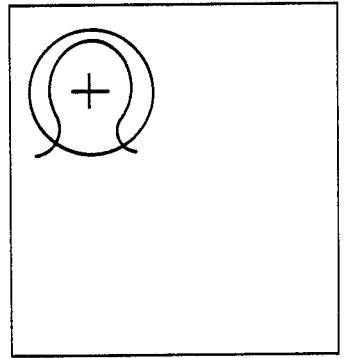

An example of the right picture in which the index circle is displayed is shown in FIG. 15.

By the way, this Rgcircle realizes the index circle displaying means 155 in FIG. 6.

As explained above, according to this embodiment, when the object point corresponding to the measuring object point is designated on the right picture, the position condition of the object point in the left picture will be operated and the line showing the position of the object point to be on the left picture, that is, the guide line will be displayed. Therefore, in the left picture, when the objecgt point is designated on this guide line, even in case the object wanted to be measured has no clear feature, the position designated and the distance and length will be able to be thereby accurately measured.

Also, in this embodiment, the mouse 145 which is a cursor operating means is at first operatively connected to the cursor displaying means 151R for the right picture and first at this time the cursor for designating the point is displayed in the right picture. When the point designation is secured in the right picture, the moving cursor and designating cursor for the point designation will be erased from the right picture, then the above mentioned mouse 145 will be released from the connection with the above mentioned cursor displaying means 151R and will be operatively conneacted to the cursor displaying means 151L for the left picture by the switching means 150 and first at this time the cursor for the point designation will be displayed in the left picture. When the point designation in the left picture is secured, the moving cursor and designating cursor for the point designation will be erased from the left picture. Therefore, by one cursor operating means (mouse 145), the movement of the cursor on both right and left pictures and the designation of the point can be easily made. Further, only when the cursor displaying means 151R and 151L are operatively connected to the mouse 145, the cursor for the point designation will be displayed in the picture. Therefore, on which picture the cursor is moved and whether the point can be designated can be known at a glance and the operatability is high.

Also, in this embodiment, an index circle which is a two-dimensional index of a size corresponding to the distance to the object can be displayed in the right picture by using the results of the measurement. Therefore, by comparing it with the above mentioned index circle, the size of the object can be known by sight. Also, by the comparison with this two-dimensional index, the relation between the vertical size and horizontal size of the object is found.

Six modifications of this embodiment shall be explained in the following.

Figure 26:
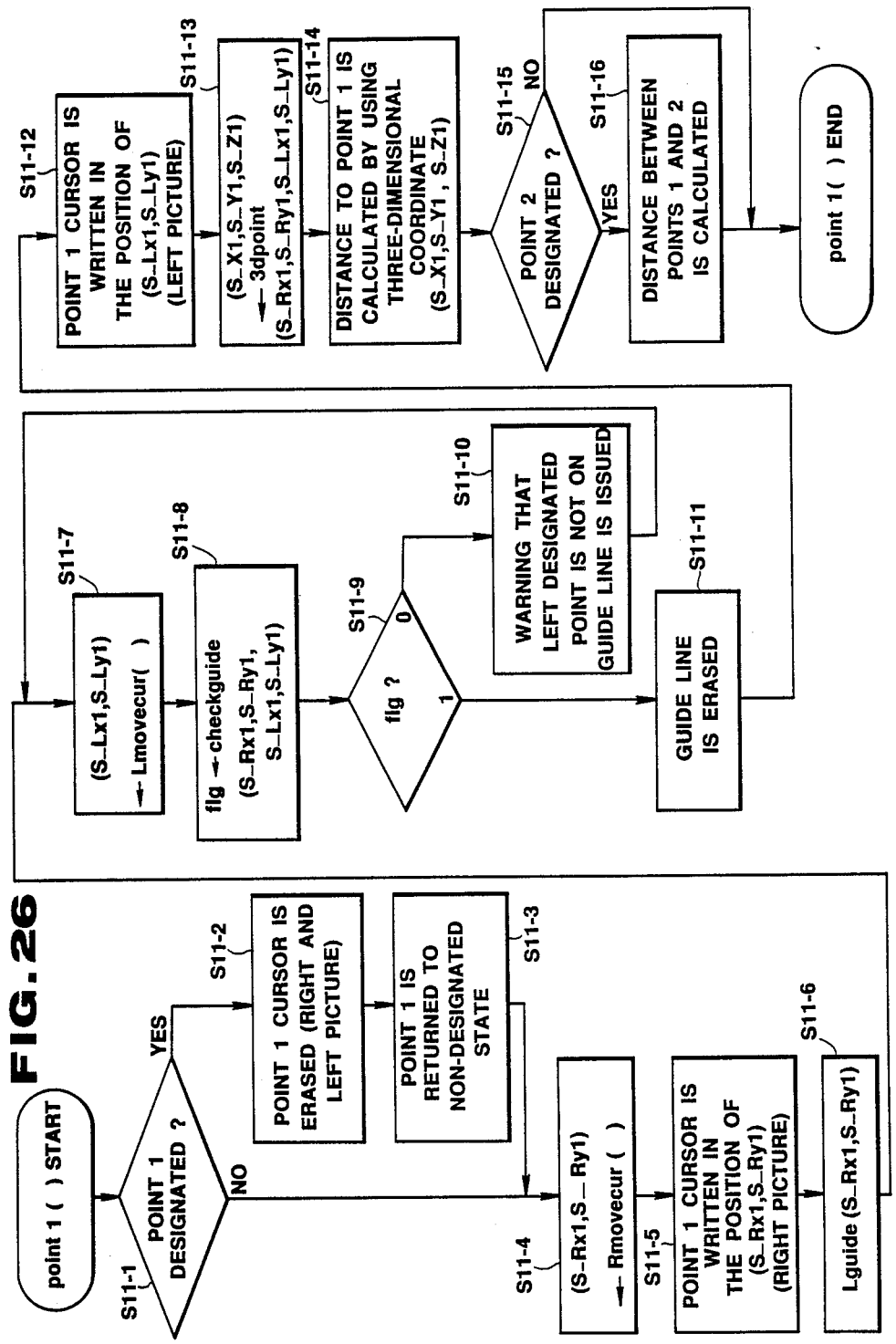
FIGS. 26 and 27 are flow charts for explaining the operation of the first modification of the second embodiment.
Figure 27:
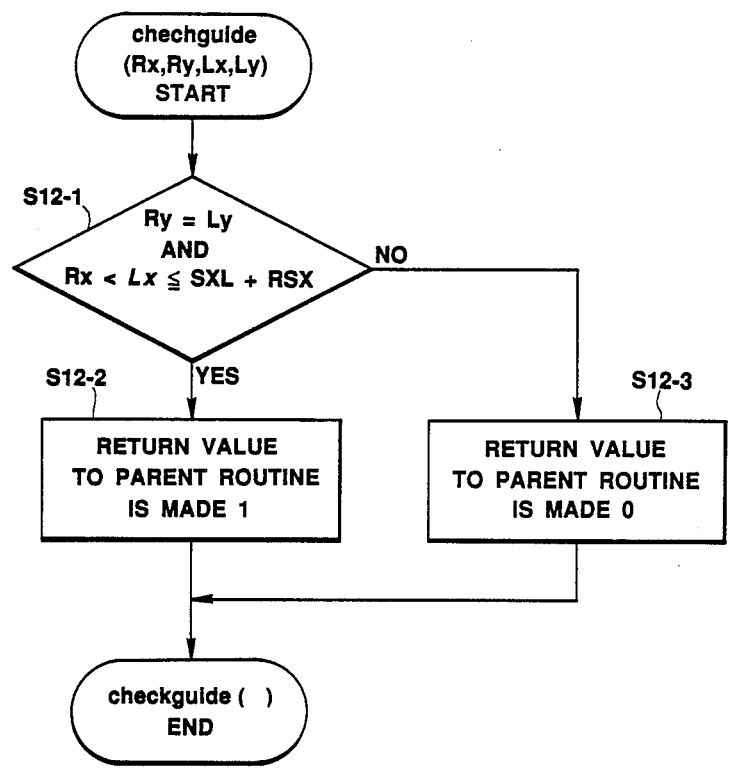

The first modification is shown in FIGS. 26 and 27.

In this modification, in the left picture, in case the other points than the guide line are designated, a warning will be issued without calculating the three-dimensional coordinate.

First, the point1 ( ) shall be explained by using FIG. 26.

In the point1 in this modification, when this routine starts, S11-1 to S11-7 are exactly the same as S5-1 to S5-7 of the point1 in the embodiment shown in FIG. 20. In this modification, after the Lmovecur of S11-7, a sub-routine called checkguide ( ) is made in S11-8. In his routine, the coordinates (S_Rx1, S_Ry1, S_Lx1, S_Ly1) of the points designated in the respective pictures are made arguments and it is checked whether the point designated in the left picture is on the guide line or not. In case it is on the guide line, 1 will be substituted for flg. In case it is not on the guide line, 0 will be substituted for flg. The above mentioned checkguide ( ) is shown in FIG. 27.

Next, in S11-9, flg is judged. In the case of 0, in S11-10, a warning that the left designated point is not on the guide line is issued and the process returns to S11-7. That is to say, the point is designated again in the light picture. On the other hand, in case flg is 1, the process proceeds to S11-11 and the guide line is erased.

Then, the above mentioned S11-12 to S11-16 are made and the process ends. By the way, the above mentioned S11-12 to S11-16 are exactly the same as S5-8 to S5-13 of the point1 in the embodiment shown in FIG. 20.

By the way, the point2 in this modification is not illustrated but is basically the same as the point1 shown in FIG. 26 and has the description (including the coordinates) relating to the points 1 and 2 replaced.

By the way, even in the case of designating the circle fitted point, the same as in the above mentioned point1, it may be considered to issue a warning in case the left designated point is not on the guide line but, in such case, in the pointm, the same steps as the above mentioned S11-8 to S11-10 may be added.

Now, the above mentioned checkguide ( ) shall be explained in the following by using FIG. 27.

In this routine, the x and y coordinates of the designated point of the right picture and the x and y coordinates of the designated point of the left picture (Rx, Ry, Lx, Ly) delivered from the parent routine (point1 or point2) are made arguments.

When this routine starts, first, in S12-1, Ry=Ly and Rx>Lx≦SXL+RSX are judged. That is to say, it is judged whether the left designated point (Lx, Ly) is mounted on the guide line having (Rx, Ry) as the extreme left point. In the case of YES, in S12-2, the return value to the parent routine is made 1. In the case of NO, in S12-3, the return value to the parent routine is made 0 and the process ends.

Thus, according to this modification, as the point can be designated only on the guide line, the object point can be positively specified and the distance and length can be accurately measured.

Figure 28:
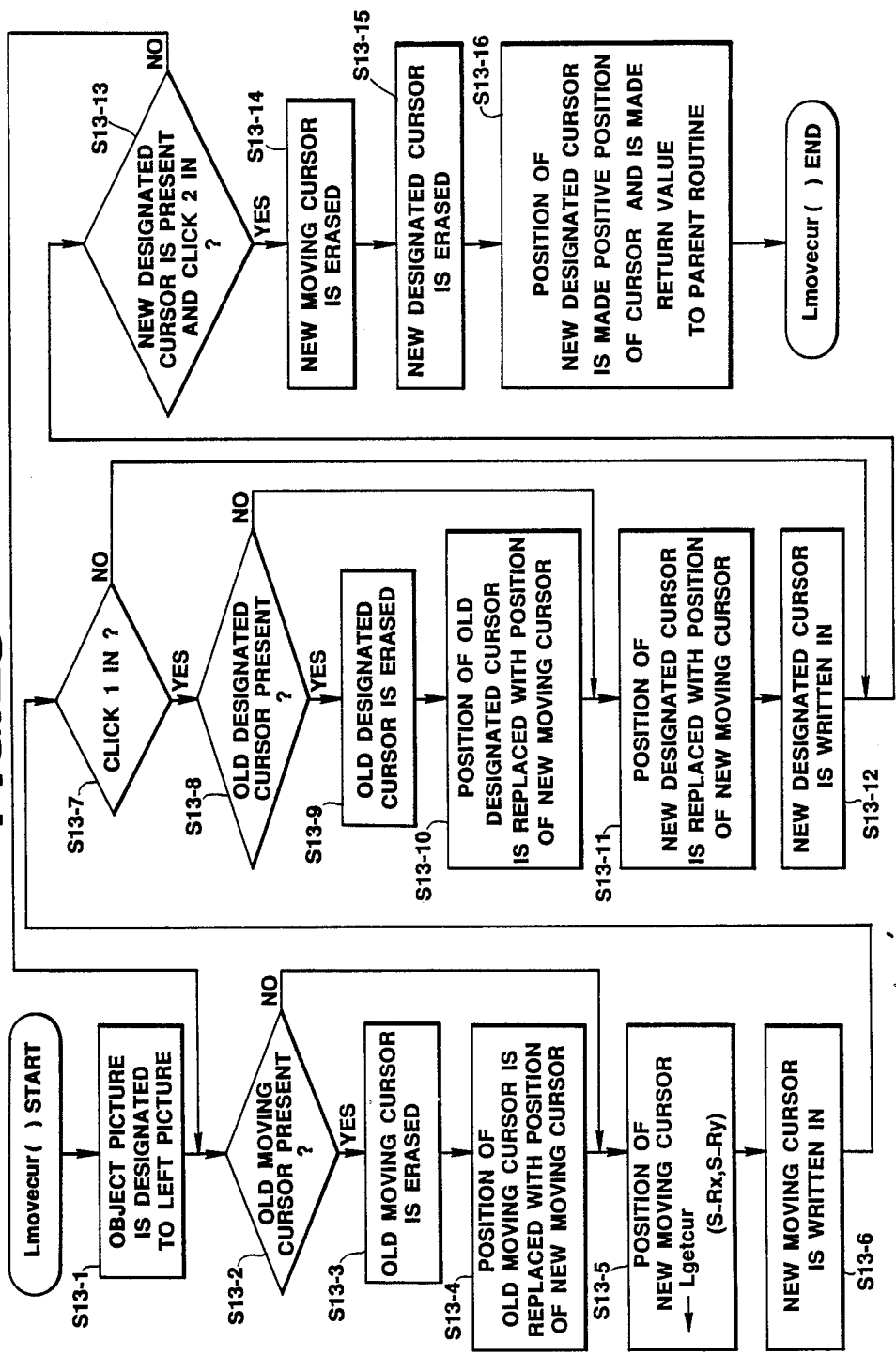
FIGS. 28 and 29 are flow charts for explaining the operation of the second modification of the second embodiment.
Figure 29:
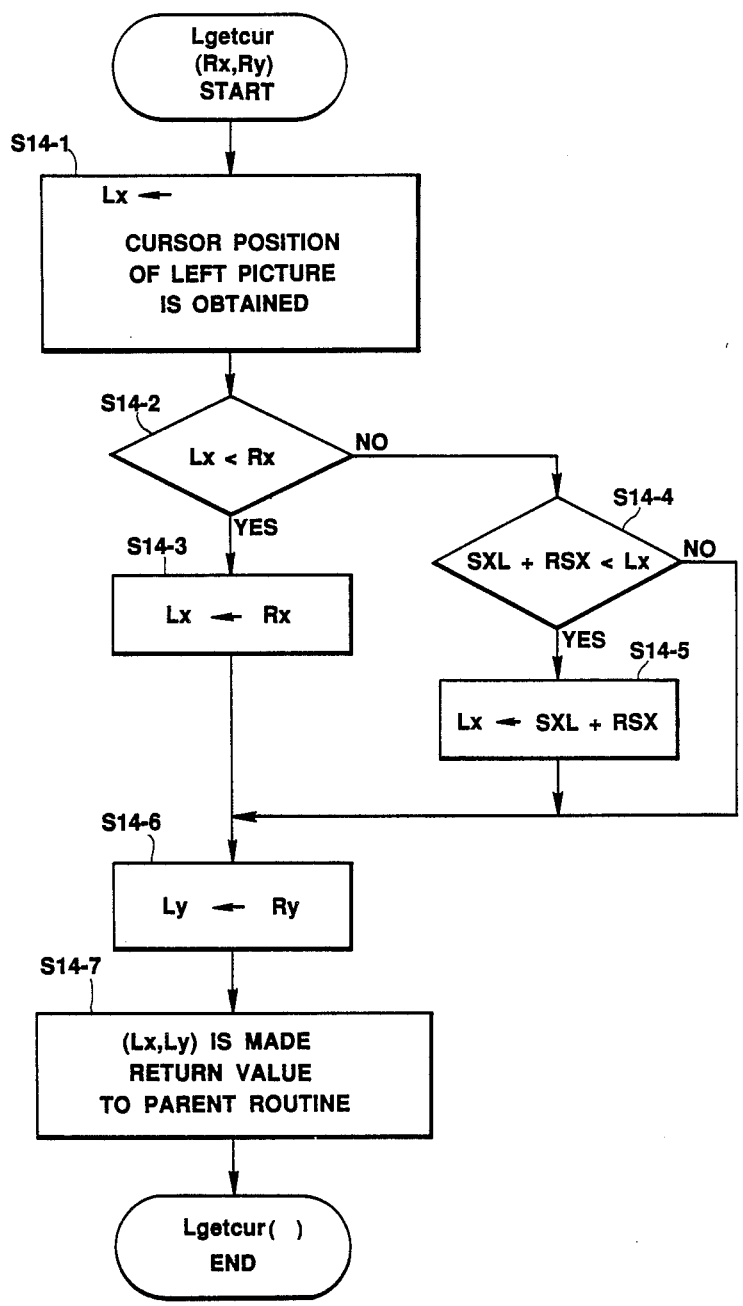

The second modification is shown in FIGS. 28 and 29.

In this modification, in the left picture, the cursor can not move except on the guide line.

First, the Lmovecur ( ) shall be explained by using FIG. 28.

In the Lmovecur in this modification, first, in S13-1, the object picture is set in the left picture. Then, S13-2 to S13-4 are made but are the same as S7-2 to S7-4 in the Rmovecur shown in FIG. 22.

Then, in S13-5, a sub-routine called "Lgetcur ( )" is made. In this routine, on the basis of the coordinate (S_Rx, S_Ry) of the designated point in the right picture, the position of the moving cursor in the left picture is corrected to be on the guide line and the resultant x and y coordinates are made the position of the new moving cursor.

Then, S13-6 to S13-16 are made to end the process and are the same as S7-6 to S7-16 in the Rmovecur shown in FIG. 22.

The above mentioned Lgetcur ( ) shall be explained in the following by using FIG. 29.

In this routine, the x and y coordinates (Rx, Ry) of the designated point on the right picture delivered from the parent routine (Lmovecur) are made arguments.

When this routine starts, first, in S14-1, the position of the cursor in the left picture is obtained by the mouse 145 and the x coordinate is substituted for Lx.

Then, in S14-2, Lx<Rx is judged. That is to say, it is judged whether Lx is on the left side rather than at the extreme left end of the guide line. In the case of YES, in S14-3, Rx is substituted for Lx. That is to say, Lx is made the x coordinate at the extreme left end of the guide line and the process proceeds to S14-6. On the other hand, in the case of NO in the above mentioned S14-2, in S14-4, SXL+RSX<Lx is judged. That is to say, it is judged whether Lx is on the right side rather than at the extreme right end of the left picture. In the case of YES, in S14-5, SXL+RSX is substituted for Lx. That is to say, Lx is made the x coordinate at the extreme right end of the left picture and the process proceeds to S14-6. On the other hand, in the case of NO in the above mentioned S14-4, the process proceeds as it is to S14-6.

In the above mentioned S14-6, Ry is shifted into Ly. That is to say, Ly is made the y coordinate of the guide line.

Next, in S14-7, (Lx, Ly) is made a return value to the parent routine. This (Lx, Ly) is a point on the guide line.

Thus, according to this modification, even if the mouse 145 is moved two-dimensionally in the left picture, only the x direction moving information will be made the cursor moving direction. In case the position of the cursor deviates from the guide line, the displayed cursor will be shifted onto the guide line. Therefore, the point can be designated without fail on the guide line.

The third modification is shown in FIGS. 30 to 37.

In the so far described modifications, the distortion aberration of the objective lens system of the endoscope is neglected but, in this modification, in displaying the guide line and index circle and determining the three-dimensional coordinate of the object point, the distortion aberration is corrected by considering its influence.

Figure 30A:
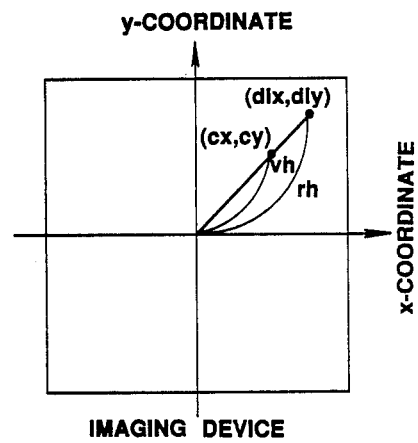
FIGS. 30 to 37 relate to the third modification of the second embodiment.
Figure 30B:
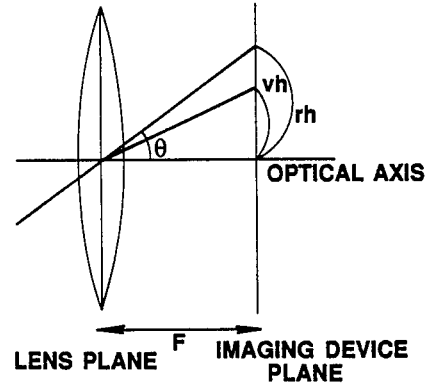

First, with reference to FIG. 30, the principle of the distortion aberration correction shall be explained.

As shown in FIG. 30($a$), the position of the point in case the influence (of the distortion aberration) is received before correcting the distortion aberration on the imaging device shall be represented by (cx, cy) and the position of the point in case the influence is not received after correcting the distortion aberration shall be represented by (dix, diy).

The distortion aberration is corrected on the basis of the following relative formulae:

$$vh = F\theta$$

$$rh = F \tan \theta$$

wherein vh represents a distance between the original and (cx, cy) and rh represents a distance between the original and (dix, diy) and, as shown in FIG. 30($b$), F represents a focal distance and $\theta$ represents an angle formed by the straight line passing through the center of the imaging means and (dix, diy) and the optical axis.

Therefore, the conversion formulae are as follows:
In the case of the distortion aberration correction:

$$vh = (cx^2 + cy^2)^{\frac{1}{2}}$$

$$\theta = vh/F$$

$$rh = F \times \tan\theta$$

$$s = rh/vh$$

$$dix = cx \times s$$

$$diy = cy \times s.$$

In the case of the inverse distortion aberration correction:

$$rh = (dix^2 + diy^2)^{\frac{1}{2}}$$

$$\theta = \tan^{-1}(rh/F)$$

$$vh = F \times \theta$$

$$s = vh/rh$$

$$cx = dix \times s$$

$$cy = diy \times s.$$

Figure 33:
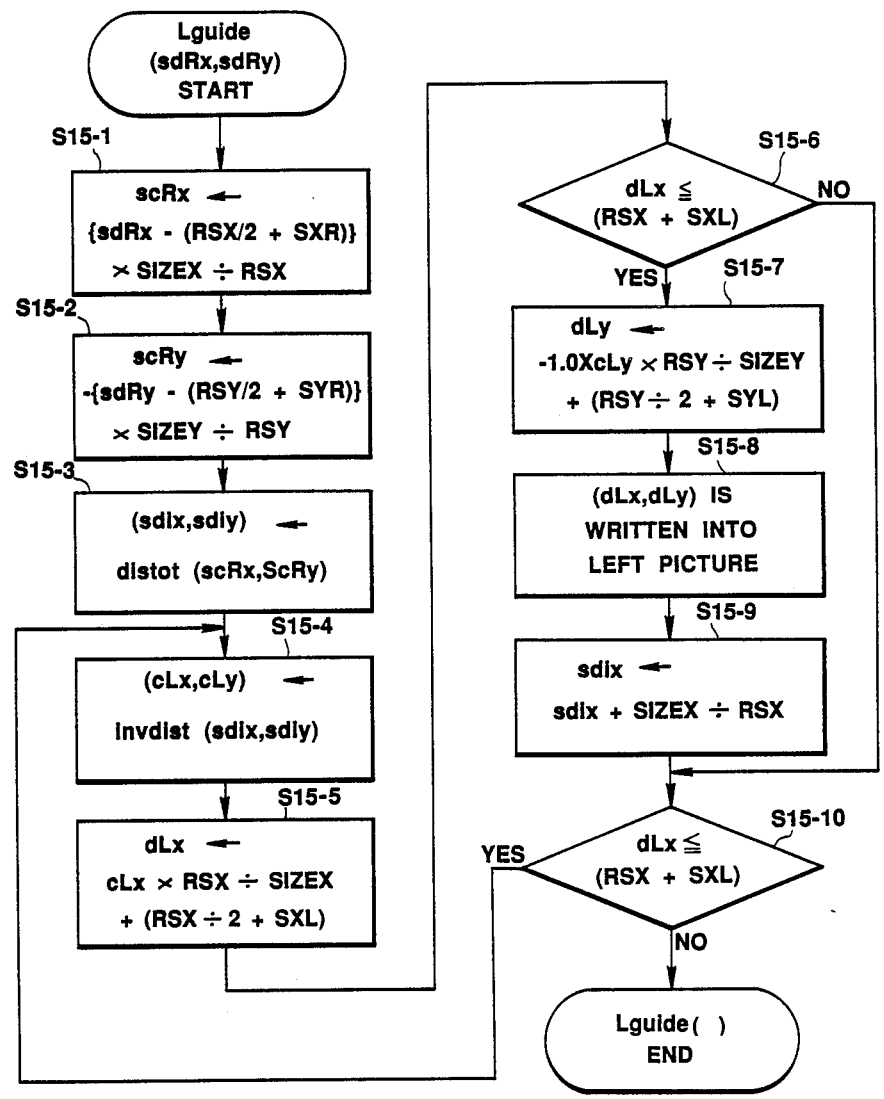

The Lguide ( ) shall be explained in the following by usig FIG. 33.

This Lguide is a routine displaying the guide line. Therein, in order to correct the distortion aberration, it is necessary to once convert the coordinates on the picture to coordinates on the imaging device, because the coordinates on the picture are usually expressed in integers, therefore can not be expressed below the decimal point and can not be accurately corrected. Therefore, the coordinates are converted to the coordinates on the imaging device expressed in real numbers and then the distortion aberration is corrected. By the way, the coordinate conversion is as explained by using FIG. 13.

In the above mentioned Lguide, the x and y coordinates (sdRx, sdRy) of the designated point of the right picture delivered from the parent routine are made arguments. When this routine starts, first, in S15-1, {sdRx−(RSX/2+SXR)}×SIZEX/RSX is operated and is made an x coordinate scR on the imaging device of the right designated point.

Then, in S15-2, −{sdRy−(RSY/2+SYR)}×SIZEY/RSY is operated and is made a y coordinate scRy on the imaging device of the right designated point.

Figure 36:
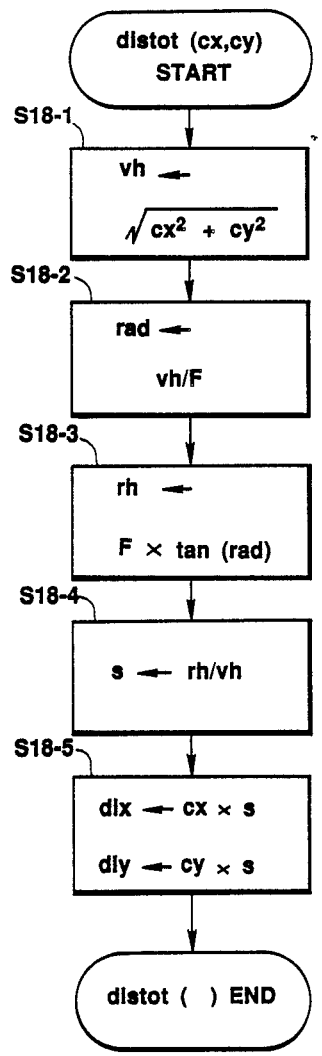

Next, in S15-3, the coordinates (scRx, scRy) on the imaging device are made arguments and a sub-routine called "distot ( )" is made. This routine is to correct the distortion aberration so as to obtain x and y coordinates (sdix, sdiy) in the case of receiving no influence of the distortion aberration on the right imaging device. The above mentioned distot is shown in FIG. 36.

Figure 37:
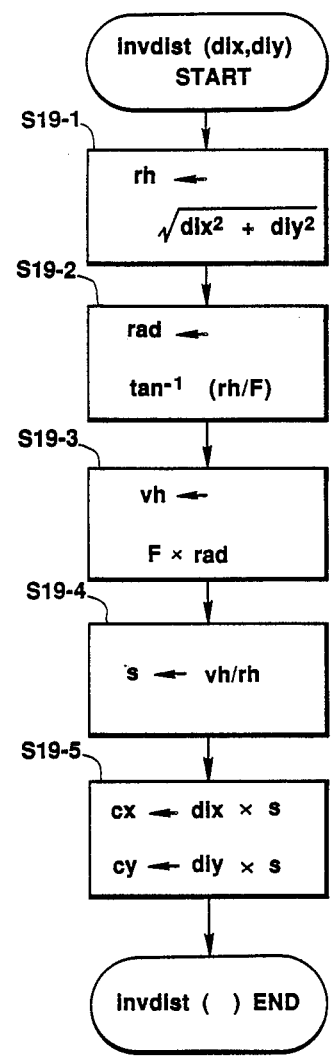

Then, in S15-4, the above mentioned (sdix, sdiy) are made arguments and a sub-routine called "invdist ( )" is made. This routine is to correct the inverse distortion aberration so as to obtain x and y coordinates (cLx, cLy) at the extreme left end of the guide line in the case of receiving the influence of the distortion aberration on the left imaging device. The above mentioned invdist is shown in FIG. 37. By the way, in the above mentioned S15-4, it is used that the right designated point taking the influence of the distortion aberration and the coordinate at the extreme left end of the guide line are equal to each other.

Then, in S15-5, cLx×RSX/SIZEX+(RSX/2+SXL) is made dL. That is to say, the x coordinate on the left imaging device is converted to the x coordinate on the left pictre.

Next, in S15-6, dLx≦(RSX+SXL) is judged. That is to say, whether dLx has reached the right end of the left picture or not is judged. In the case of YES, the next S15-7 to S15-9 are made and then the process proceeds to S15-10. In the case of NO, the process proceeds as it is to S15-10.

In the above mentioned S15-7, −1.0×cLy×RSY/SIZEY+(RSY/2+SYL) is made dLy.

Then, in S15-8, (dLx, dLy) is written into the left picture.

Next, in S15-9, sdix+SIZEX/RSX is made sdix. That is to say, the x coordinate of the point on the imaging device is moved to the right by the minimum unit.

Then, in the above mentioned S15-10, dLx≦(RSX+SXL) is judged. That is to say, whether dLx has reached the right end of the left picture or not is judged. In the case of YES, the process returns to the above mentioned S16-4 and the next point on the guide line is written into the left picture. In the case of NO, the process ends.

Figure 31:
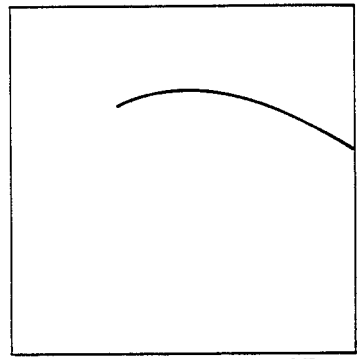

Thus, the guide line on which the distortion aberration has been corrected is displayed on the left picture. An example of the left picture on which this guide line is displayed is shown in FIG. 31.

Figure 34:
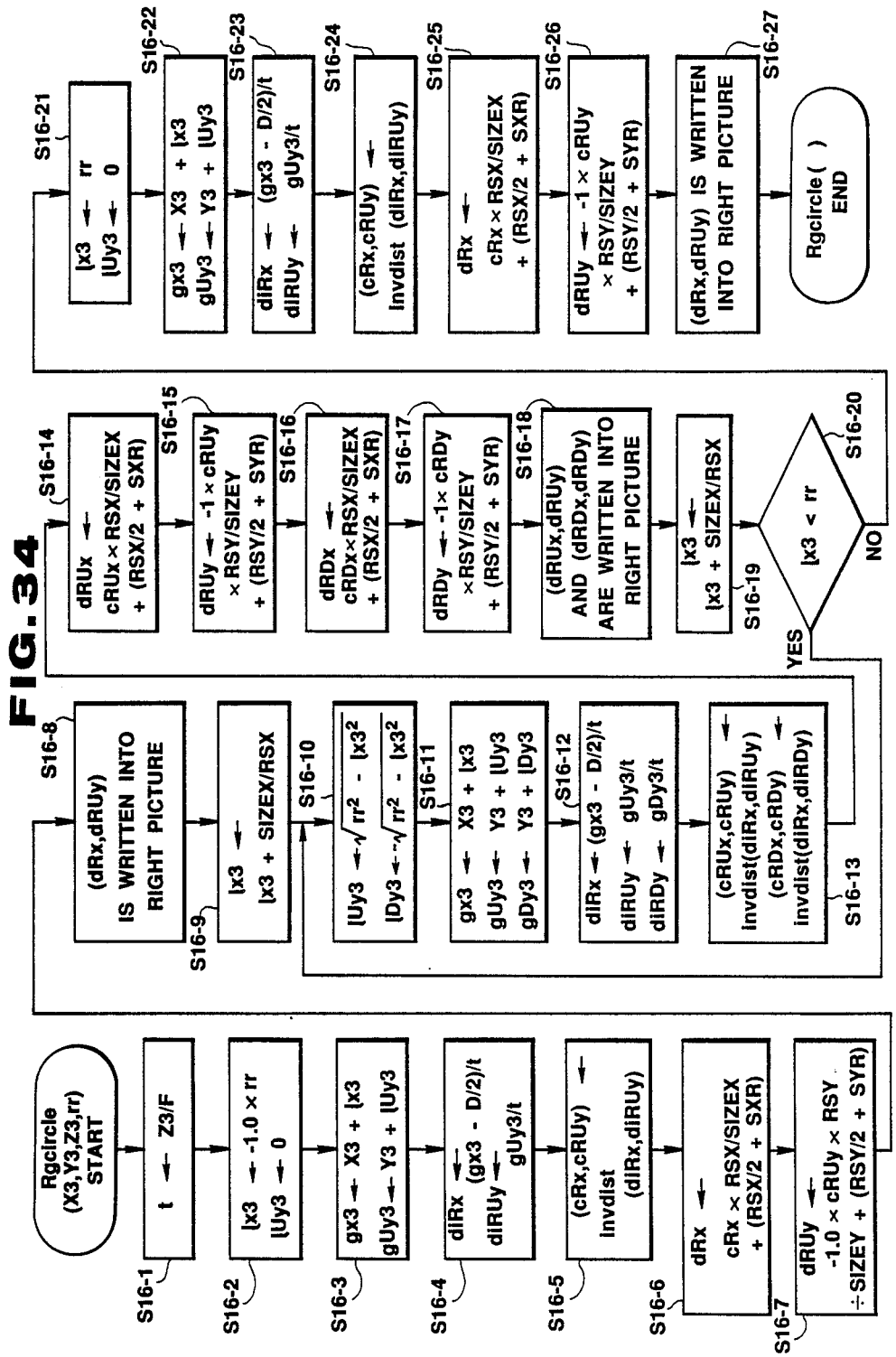
Figure 35:
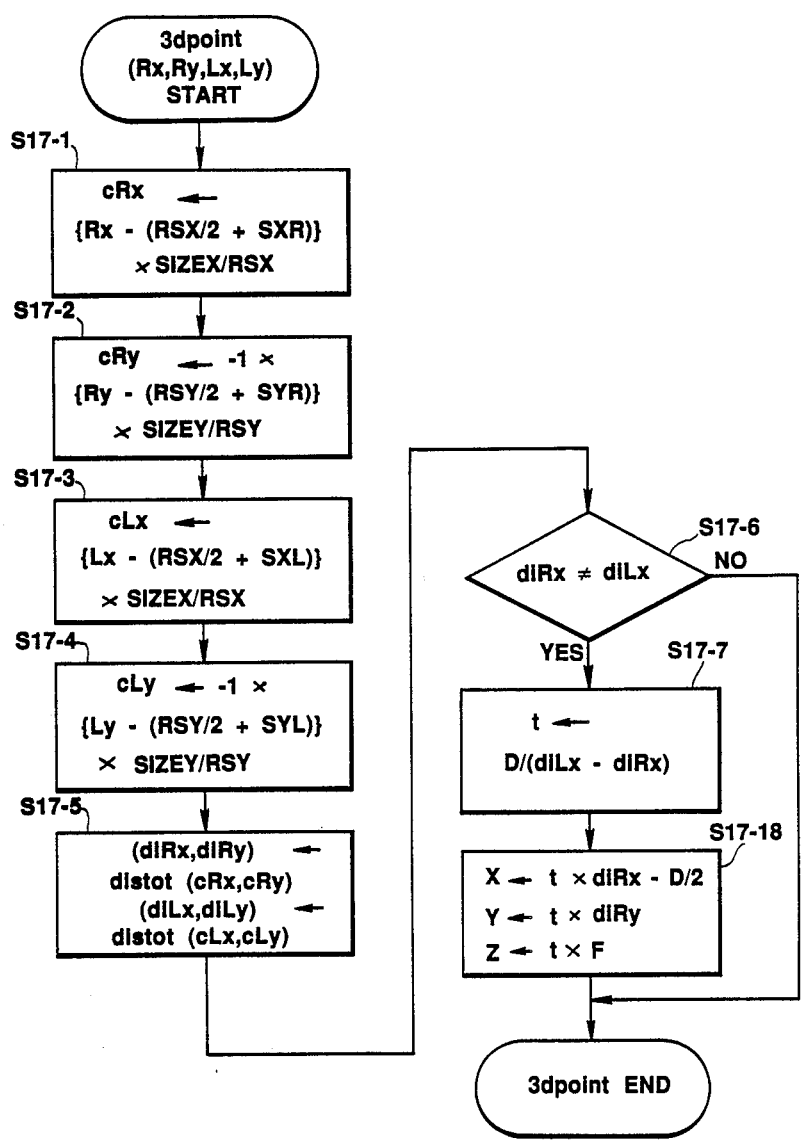

The Rgcircle ( ) shall be explained in the following by using FIG. 34.

In this routine, the three-dimensional coordinate (X3, Y3, Z3) and the radius rr of the circle delivered from the parent routine (pointm) are made arguments.

When this routine starts, first, in S16-1, Z3/F is made a parameter t.

Then, in S16-2, −1.0×rr is made lx3 and 0 is made lUy3. That is to say, x and y coordinates having the circle fitted point of the point at the left end of the index circle as a center are determined.

Then, in S16-3, X3+lx3 is made gx3 and Y3+lUy3 is made gUy3. That is to say, the coordinate of the point at the above mentioned left end is converted to the scope centner coordinate.

Then, in S16-4, (gx3−D/2)/t is made diRx and gUy3/t is made iRUy. That is to say, the point of the above mentioned left end is converted to x and y coordinates in the case of receiving no influence of the distortion aberration in the right imaging device.

Next, in S16-5, (diRx, diRUy) is made an argument and the invdist is made to obtain x and y coordinates (cRx, cRUy) in the case of receiving the influence of the distortion aberration on the right imaging device.

Then, in S16-6, cRx×RSX/SIZEX+(RSX/2+SXR) is operated and is made an x coordinate on the right picture.

Then, in S16-7, −1.0×cRUy×RSY/SIZEY+(-RSY/2+SYR) is operated and is made a y coordinate dRU on the right picture.

The above mentioned S16-6 and S16-7 are to convert the position on the imaging device to a position on the picture.

Next, in S16-8, the point (dRx, dRUy) is written into the right picture.

Thus, in S16-2 to S16-8, the point at the left end of the index circle in the case of receiving the influence of the distortion aberration is written in the right picture.

Then, in S16-9, lx3+SIZEX/RSX is made lx3 and the x coordinate of the point on the index circle is moved to the right.

Next, in S16-10, $(rr^2 - lx3^2)^{\frac{1}{2}}$ is made the y coordinate lUy3 of the point on the upper side on the index circle corresponding to the above mentioned lx3 and $-(rr^2 - lx3^2)^{\frac{1}{2}}$ is made the y coordinate lDy3 of the point on the lower side on the index circle corresponding to the above mentioned lx3.

Then, in S16-11, X3+lx3 is made gx3, Y3+lUy3 is made gUy3 and Y3+lDy3 is made gD. That is to say, the coordinates of the two points on the above mentioned index circle are convereted to scope center coordinates.

Then, in S16-12, (gx3−D/2)/t is made diRx, gUy3/t is made diRUy and gDy3/t is made diRDy. That is to say, the two points on the above mentioned index circle are converted to x and y coordinates in the case of receiving no influence of the distortion aberration on the right imaging device.

Next, in S16-13, (diRx, diRUy) and (diRx, diRDy) are made arguments and the invdist is made respectively with them to obtain the x and y coordinates (cRUx, cRUy) and (cRDx, cRDy) in the case of receiving the influence of the distortion aberration on the right imaging device.

Then, in S16-14, cRUx×RSX/SIZEX+(RSX/2+SXR) is made dRUx.

Next, in S16-15, −1×cRUy×RSY/SIZEY+(-RSY/2+SYR) is made dRUy.

Then, in S16-16, cRDx×RSX/SIZEX+(RSX/2+SXR) is made dRDx.

Then, in S16-17, −1×cRDy×RSY/SIZEY+(-RSY/2+SYR) is made dRDy.

In the above mentioned S16-14 to S16-17, the position on the imaging device is converted to a position on the picture.

Then, in S16-18, a point (dRUx, dRUy) and point (dRUx, dRDy) are written into the right picture.

Then, in S16-19, lx3+SIZEX/RSX is made lx3. That is to say, the x coordinate on the index circle is moved to the right.

Next, in S16-20, lx3<rr is judged. In the case of YES, that is, in case the point on the index circle has not reached the right end, the process returns to the above mentioned S16-10. On the other hand, in the case of NO, that is, in case the point on the index circle has reached the right end, the process proceeds to the next S16-21. Thus, until the point on the index circle reaches the right end, the two points on the index circle in the case of receiving the influence of the distortion aberration are written into the picture in the order from the left side.

Then, in the above mentioned S16-21, rr is made lx3 and 0 is made lUy3. That is to say, the x and y coordinates having the circle fitted point as a center of the point at the right end of the index circle are determined.

Next, S16-22 to S16-27 are made to end the process. The above mentioned S16-22 to S16-27 are the same as the above mentioned S16-3 to S16-8. That is to say, the coordinate of the point at the right end is converted to the scope center coordinate, is converted to the point on the right imaging device, is converted to the coordinate in the case of receiving the influence of the distortion aberration and is further converted to the position on the picture and the point (dRx, dRUy) is written into the right picture.

Thus, in S16-21 to S16-27, the point at the right end of the index circle is written in the right picture.

Figure 32:
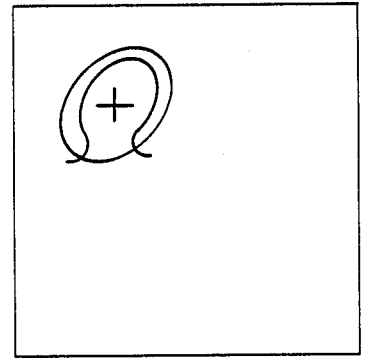

The index circle in which the distortion aberration is corrected is thus displayed. An example of the right picture in which this index circle is displayed is shown in FIG. 32.

The 3dpoint ( ) shall be explained in the following by using FIG. 335.

In this routine, the x and y coordinates (Rx, Ry) of the designated point of the right picture and the x and y coordinates (Lx, Ly) of the designated point of the left picture delivered from the parent routine (point1 or pointm) are made arguments.

The S17-1 to S17-4 of this routine are the same as the S9-1 to S9-4 in the 3dpoint ( ) shown in FIG. 24. That is to say, the positions on the respective right and left pictures are converted to the positions on the imaging devices. By the way, the coordinates on the imaging devices obtained here have been influenced by the distortion aberration.

Next, in S17-5, (cRx, cRy) and (cLx, cLy) are made arguments and the distot is made respectively with them to obtain the x and y coordinates (diRx, diRy) and (diLx, diLy) in the case that there is no influence of the distortion aberration on the imaging device.

Then, in S17-6, diRx≠diLx is judged. In the case of NO, the object point is infinitely far and the process ends. On the other hand, in the case of YES, in S17-7, D/(diLx−diRx) is operated and is made a parameter t.

Then, in S17-8, t×diRx+D/2 is made X, t×diRy is made y and t×F is made Z to determine a three-dimensional coordinate and this three-dimensional coordinate (X, Y, Z) is made a return value to the parent routine to end the process.

Thus, the three-dimensional coordinate of the object point in which the distortion aberration has been corrected is determined.

The above mentioend distot ( ) shall be explained in the following by using FIG. 36.

In this routine, the position (cx, cy) in the case of receiving the influence of the distortion aberration on the imaging device delivered from the parent routine (Lguide or 3dpoint) is made an argument.

First, in S18-1, $(cx^2+cy^2)^{\frac{1}{2}}$ is made vh. Then, in S18-2, vh/F is made rad. Then, in S18-3, F×tan (rad) is made rh. Then, in S18-4, rh/vh is made s. Then, in S18-5, cx×s is made dix and cy×s is made diy. The position (dix, diy) after the distortion aberration correction is made a return value to the parent routine to end the process. The above mentioned respective steps carry out the conversion system explained by using FIG. 30.

The above mentioned invdist ( ) shall be explained in the following by using FIG. 37.

In this routine, the position (dix, diy) in the case of receiving no influence of the distortion aberration on the imaging device delivered from the parent routine (Lguide or Rgcircle) is made an argument.

First, in S19-1, $(dix^2+diy^2)^{\frac{1}{2}}$ is made rh. Then, in S19-2, $\tan^{-1}$ (rh/F) is made rad. Then, in S19-3, F×rad is made rh. Then, in S19-4, vh/rh is made s. Then, in S19-5, dix×s is made cx and diy× is made cy. The position (cx, cy) after the inverse distortion aberration is corrected is made a return value to the parent routine to end the process. The above mentioned respective steps carry out the conversion system explained by using FIG. 30.

When the Lguide, Rgcircle and 3dpoint in this third modification are replaced respectively with the routines shown in FIGS. 23, 25 and 24, in the case of displaying the guide line, displaying the index circle and determining the three-dimensional coordinate of the object point, the distortion aberration will be able to be corrected. The other routines are the same as in the second embodiment.

Figure 38:
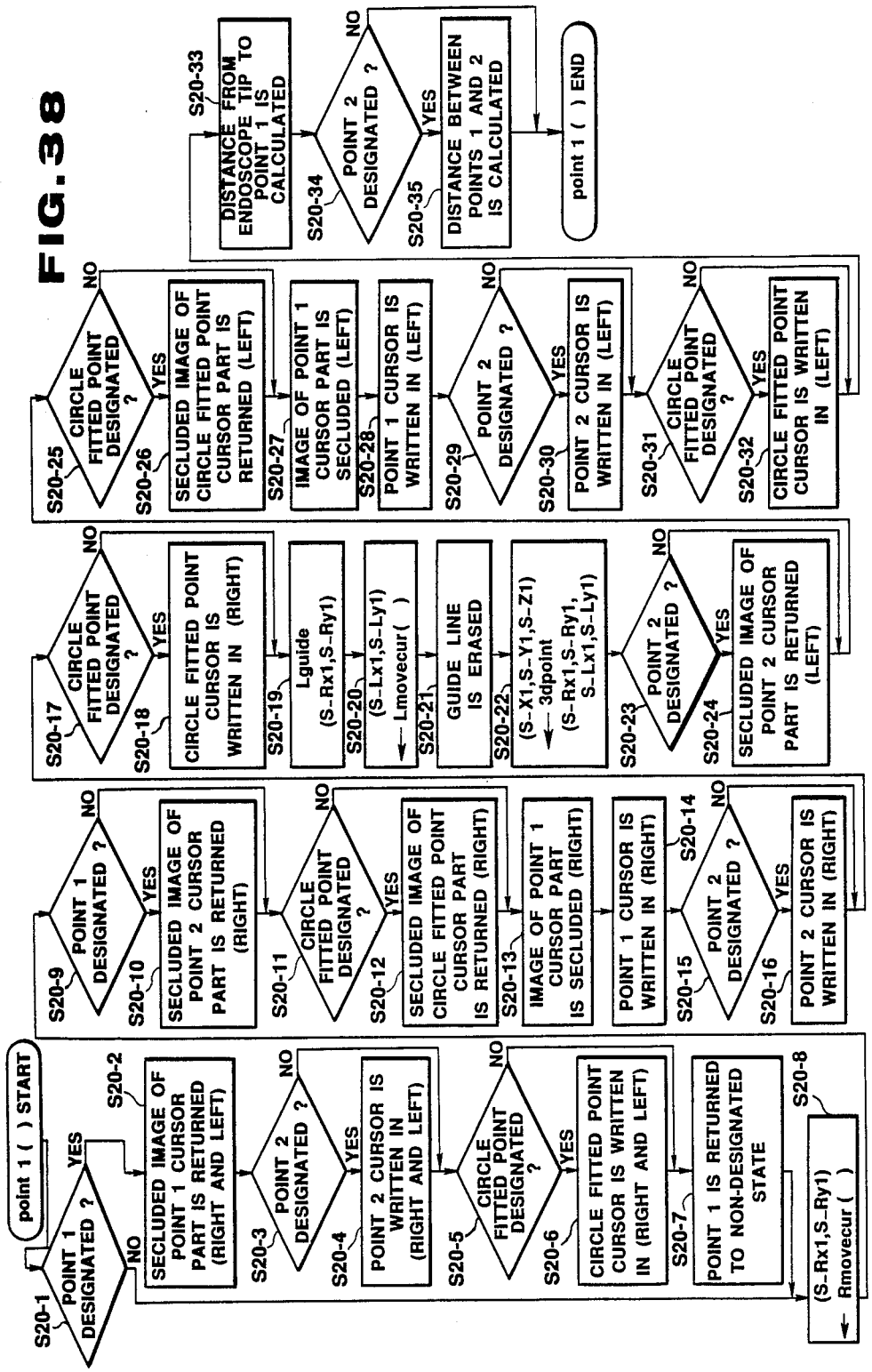
FIGS. 38 and 39 are flow charts for explaining the operation of the fourth modification of the second embodiment.
Figure 39:
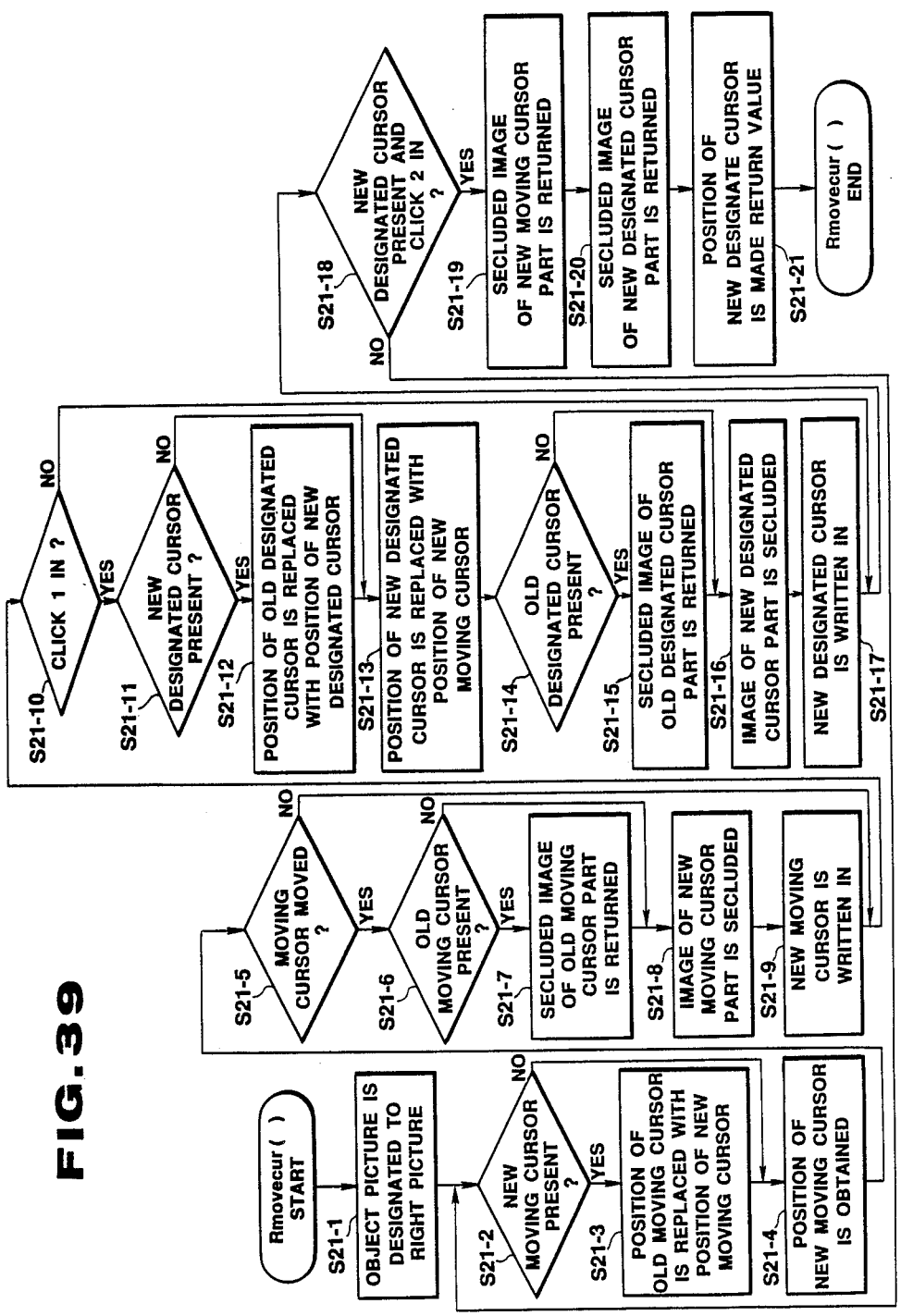

The fourth modification is shown in FIGS. 38 and 39.

In the case of the second embodiment and its first to third modifications, the case of a plurality of sets of the respective memories of R, G and B has been explained. In such case, the cursor is written into the memories of RGB different from the memories of RGB in which the image is written and is later added.

On the other hand, the fourth modification is an example of the case of only one set of the respective memories of RGB.

In this case, the cursor will be written with the image of the cursor part erased on the memory of RGB in which the image is written and, if the cursor is only written, the image of the cursor part will be lost.

Therefore, in this modification, before the cursor is written, the image of the cursor part is secluded so that, when the cursor is erased, the secluded image will be returned and the image of the cursor part will not be lost.

First, the point1 ( ) shall be explained by using FIG. 38.

When this routine starts, first, in S20-1, whether the point 1 is designated or not is judged. In the case of NO, the process proceeds as it is to S20-8. In the case of YES, S20-2 to S20-7 are made and then the process proceeds to S20-2.

In the case of YES in the above mentioned S20-1, first, in S20-2, the secluded image of the point 1 cursor part in the respective right and left pictures is returned. Then, in S20-3, whether the point 2 is designated or not is judged. In the case of YES, in S20-4, the point 2 cursor is written into the respective right and left pictures and then the process proceeds to S20-5. In the case of NO, the process proceeds as it is to S20-5. In S20-5, whether the circle fitted point is designated or not is judged. In the case of YES, in S20-6, the circle fitted point cursor is written into the respective right and left pictures and then the process proceeds to S20-7. In the case of NO, the process proceeds as it is to S20-7. In 20-7, the point 1 is returned to a non-designated state and the process proceeds to the above mentioned S20-8.

Thus, in case the point 1 is designaged, in S20-2, when the secluded image of the point 1 cursor part is returned, the point 1 cursor will be erased. However, in case the other point 2 cursor and circle fitted point cursor are adjacent to the point 1 cursor, when the point 1 cursor is erased, the other cursors will be likely to be painted out. Therefore, in case the other points are designated, in S20-4 and S20-6, the cursors of the other points are newly re-written.

Next, in the above mentioned S20-8, the Rmovecur is made to obtain the x and y coordinates (S_Rx1, S_Ry1) of the designated point in the right picture. The Rmomvecur ( ) in this modification is shown in FIG. 39.

Then, in S20-9, whether the point 2 is designated or not is judged. In the case of YES, in S20-10, the secluded image of the point 2 cursor part is returned in the right picture and then the process proceeds to S20-11. In the case of NO, the process proceeds as it is to S20-11. In S20-11, whether the circle fitted point is designated or not is judged. In the case of YES, in S20-12, the secluded image of the circle fitted point part is returned in the right picture and then the process proceeds to S20-13. In the case of NO, the process proceeds as it is to S20-13. In S20-13, the image of the point 1 cursor part is secluded in the right picture. In S20-14, the point 1 cursor is written into the right picture.

Thus, before the point 1 cursor is written in, in S5-13, the image of the point 1 cursor part is secluded. However, in case the other points (such as the point 2 and circle fitted point) are adjacent to the point 1 cursor, in case the image of the point 1 cursor part is secluded, the cursors of the other points will be likely to be included. Therefore, in case the other points are designated, in S20-10 and S20-12, the images of the cursor parts of the other points are returned.

Then, in S20-15, whether the point 2 is designated or not is judged. In the case of YES, in S20-16, the point 2 cursor is written into the right picture and then the process proceeds to S20-17. In the case of NO, the process proceeds as it is to S20-17. In S20-17, whether the circle fitted point is designated or not is judged. In the case of YES, in S20-18, the circle fitted point cursor is written into the right picture and then the process proceeds to S20-19. In the case of NO, the process proceeds as it is to S20-19.

As described above, in case the image of the point 1 cursor part is secluded, the cursors of the other points will be erased. Therefore, in the above mentioned S20-15 to S20-18, cursors are newly re-written in the right picture.

Then, in S20-19, the Lguide is made and the guide line is written on the basis of the coordinate (S_Rx1, S_Ry1) of the designated point in the right image.

Then, in S20-20, the Lmovecur is made to obtain the x and y coordinates (S_Lx1, S_Ly1) of the designated point in the left picture.

Then, in S20-21, the guide line is erased and then, in S20-22, the designated points (S_Rx1, S_Ry1, S_Lx1, S_Ly1) in the respective right and left images are made arguments and the 3dpoint is made to obtain the three-diemnsional coordinate (S_x1, S_y1, S_z1) of the point 1.

Next, in S-23, whether the point 2 is designated or not is judged. In the case of YES, in S20-24, the secluded image of the point 2 cursor part is returned in the left picture and then the process proceeds to S20-25. In the case of NO, the process proceeds as it is to S20-25. In S20-25, whether the circle fitted point is designated or not is judged. In the case of YES, in S20-26, the secluded image of the circle fitted point cursor part is returned in the left picture and then the process proceeds to S20-27. In the case of NO, the process proceeds as it is to S20-27. In S20-27, the image of the point 1 cursor part is secluded in the left picture. Then, in S20-28, the point 1 cursor is written into the left picture.

In the above mentioned S20-23 to S20-26, for the same reason as for the right picture in S20-9 to S20-12, before the point 1 cursor is written into the left picture, the images of the cursor parts of the other points than the point 1 are returned in the left picture and the cursors of the other points are erased.

Then, in S20-29, whether the point 2 is designated or not is judged. In the case of YES, in S20-30, the point 2 cursor is written into the left picture and then the process proceeds to S20-31. In the case of NO, the process proceeds as it is to S20-31. In S20-31, whether the circle fitted point is designated or not is judged. In the case of YES, in S20-32, the circle fitted point cursor is written into the left picture and then the process proceeds to S20-33. In the case of NO, the process proceeds as it is to S20-33.

In the above mentioned S20-29 to S20-32, for the same reason as for the right picture in S20-15 to S20-18, the cursors of the other points than the point 1 are newly re-written in the left picture.

Next, in S20-33, the distance from the endoscope tip to the point 1 is calculated.

Then, in S20-34, whether the point 2 is designated or not is judged. In the case of NO, the process ends. In the case of YES, in S20-35, the distance between the points 1 and 2 is calculated and the process ends.

By the way, the point2 in this modification is not illustrated but is basically the same as the point1 and has the description (including the coordinates) relating to the points 1 and 2 replaced.

Also, in the pointm, the same as in the point1, before the cursor is written, the image of the cursor part is secluded and, when the cursor is erased, the secluded image is returned.

The Rmovecur ( ) shall be explained in the following by using FIG. 39.

When this routine starts, first, in S21-1, the object picture is designated to the right picture.

Then, in S21-2, whether there is a new moving cursor or not is judged. In the case of NO, the process proceeds as it is to S21-4. In the case of YES, S21-3 is made and then the process proceeds to S21-4. In the above mentioned S21-3, the position of the new moving cursor is substituted for the position of the old moving cursor. Then, in the above mentioned S21-4, the position of the new moving cursor is obtained from the position information of the mouse 145.

Next, in S21-5, whether the moving cursor has moved or not is judged. In the case of NO, the process proceeds as it is to S21-10. In the case of YES, the process proceeds to S21-6 and whether there is the old moving cursor or not is judged. In the case of NO, the process proceeds as it is to S21-8. In the case of YES, S21-7 is made and then the process proceeds to S21-8. In the above mentioned S21-7, the secluded image of the old moving cursor part is returned.

Then, in the above mentioned S21-8, the image of the new moving cursor part is secluded and then, in S21-9, the new moving cursor is written in.

Thus, in S21-2 to S21-9, the moving cursor is erased and written in to be moved. Then, in the case of erasing the cursor, the secluded image is returned and, in the case of writing in the cursor, the image is secluded.

Then, in S21-10, whether the click 1 of the mouse 145 is engaged or not is judged. In the case of NO, the process proceeds as it is to S21-18. In the case of YES, the next S21-11 to S21-17 are made and then the process proceeds to S21-18. In the case of YES in the above mentioned S21-10, first, in S21-11, whether there is the new designated cursor or not is judged. In the case of NO, the process proceeds as it is to S21-13. In the case of YES, S21-12 is made and then the process proceeds to S21-13. In the above mentioned S21-12, the position of the new designated cursor is substituted for the position of the old designated cursor. Then, in the above mentioned S21-13, the position of the new moving cursor is substituted for the position of the new designated cursor.

Then, in S21-14, whether there is the old designated cursor or not is judged. In the case of NO, the process proceeds as it is to S21-16. In the case of YES, S21-15 is made and then the process proceeds to S21-16. In the above mentioned S21-15, the secluded image of the old designated cursor part is returned.

Next, in the above mentioned S21-16, the image of the new designated cursor part is secluded and then, in S21-17, the new designated cursor is written in.

Thus, in S21-10 to S21-17, in case the click 1 is engaged, the position of the moving cursor is made the designated cursor. The same as is described above, in the case of erasing the cursor, the secluded image is returned and, in the case of writing in the cursor, the image is secluded.

Then, in S21-18, it is judged whether there is the new designated cursor or not and the click 2 of the mouse 145 is engaged or not. In the case of NO, the process returns to the above mentioned S21-2. In the case of YES, the process proceeds to S21-19. In the above mentioned S21-18, in the case of NO, the process returns to S21-2 so that the point designation may be repeated. In the above mentioned S21-19, the secluded image of the new moving cursor part is returned and the new moving cursor is erased and then, in S21-20, the secluded image of the new designated cursor part is returned and the new designated cursor is erased. Then, in S21-21, the position of the new designated cursor is made the definite position of the cursor and is made a return value to the parent routine to end the process.

By the way, the Lmovecur in this modification is not illustrated but is basically the same as the above mentioned Rmovecur and processes the left picture instead the right picture.

Thus, according to this modification, even in case there is only one set of the respective memories of RGB, the image of the cursor part will not be lost and the cursor will be able to be displayed.

Figure 40:
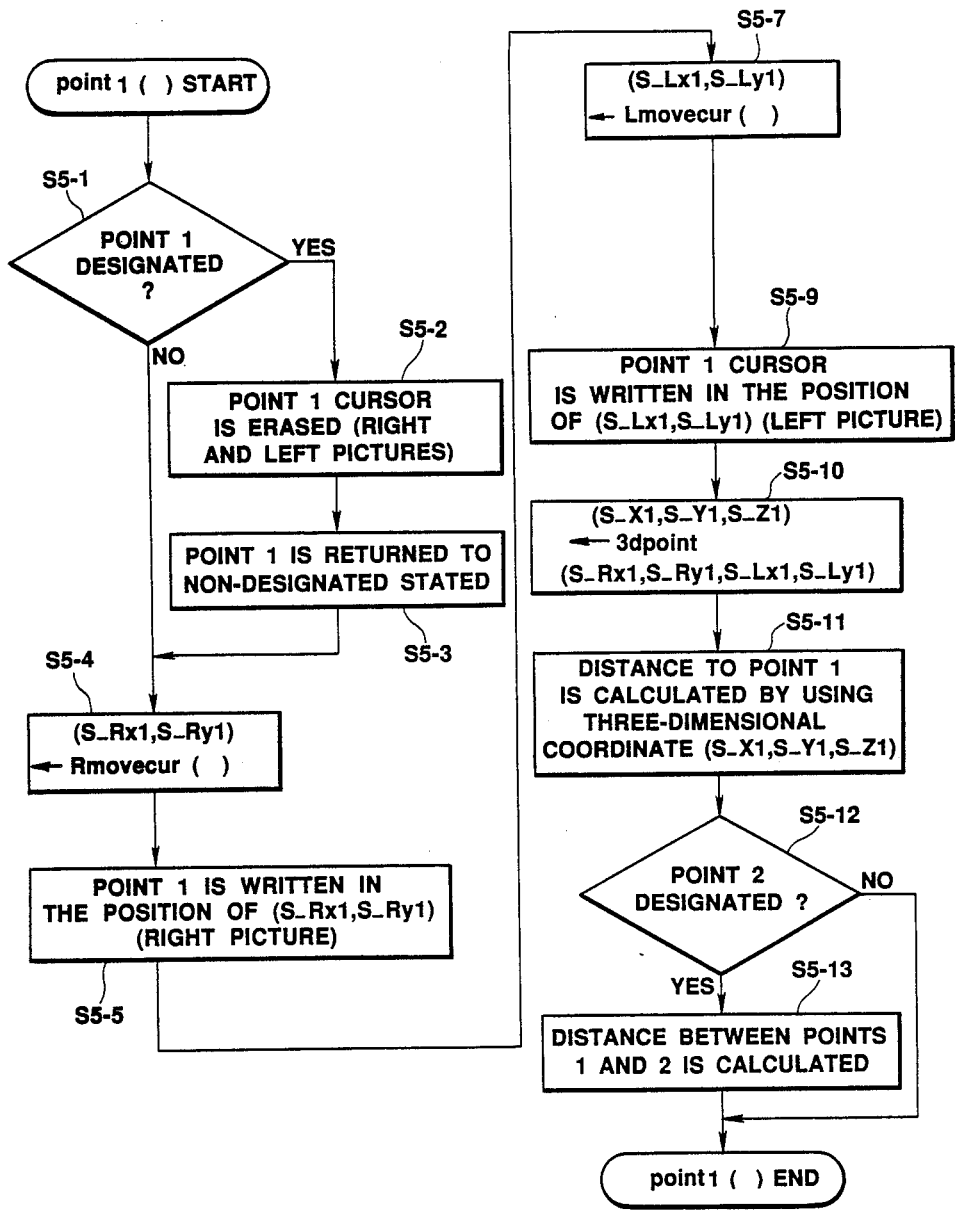
FIG. 40 is a flow chart for explaining the operation of the fifth modification of the second embodiment.

The fifth modification is shown in FIG. 40.

In this modification, in the left picture, the guide line is not displayed but the cursor is moved only in the position corresponding to the guide line.

The point1 ( ) in this modification shall be explained by using FIG. 40.

In the point1 in this modification, the S5-6 drawing the guide line and S5-6 erasing the guide line are removed from the point1 shown in FIG. 20. Therefore, in the left picture, the guide line is not displayed.

Also, the Lmovecur ( ) in this modification is as shown in FIG. 28 the same as in the second modification. The Lgetcur ( ) of S13-5 in this Lmovecur is as shown in FIG. 29 the same as in the second modification.

Therefore, according to this modification, the guide line is not displayed in the left picture but the moving cursor in the left picture moves only in the part corresponding to the guide line and therefore, the same as in the second modification, the point can be designated without fail.

By the way, the point2 ( ) and pointm ( ) are also the same as the point1 ( ).

Figure 41:
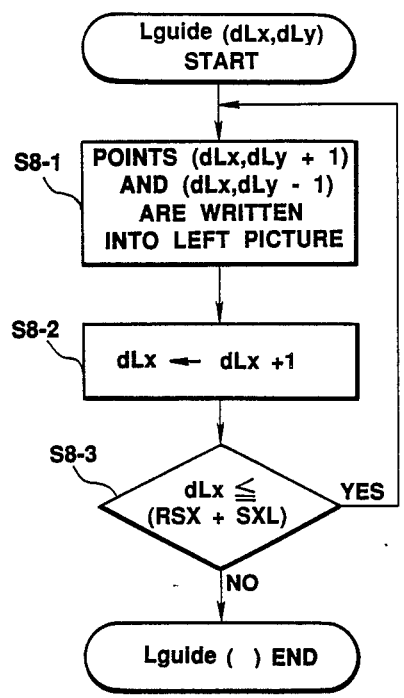
FIG. 41 is a flow chart for explaining the operation of the sixth modification of the second embodiment.

The sixth modification is shown in FIG. 41.

In this modification, the guide lines are drawn above and below the position in which the measuring object point should be located in the left picture.

In the second embodiment, as shown in FIG. 23, in S8-1 of the Lguide ( ), the point (dLx, dLy) is written into the left picture but, in this modification, as shown in FIG. 41, in S8-1 of the Lguide ( ), the points (dLx, dLy+1) and (dLx, dLy−1) are written into the left picture. The other formations are the same as in the second embodiment.

According to this modification, the guide line itself does not hide the important image.

The second embodiment of the present invention is shown in FIGS. 42 to 49.

In this embodiment, the monitor is one unit in which the right and left images are selectively displayed.

Figure 42:
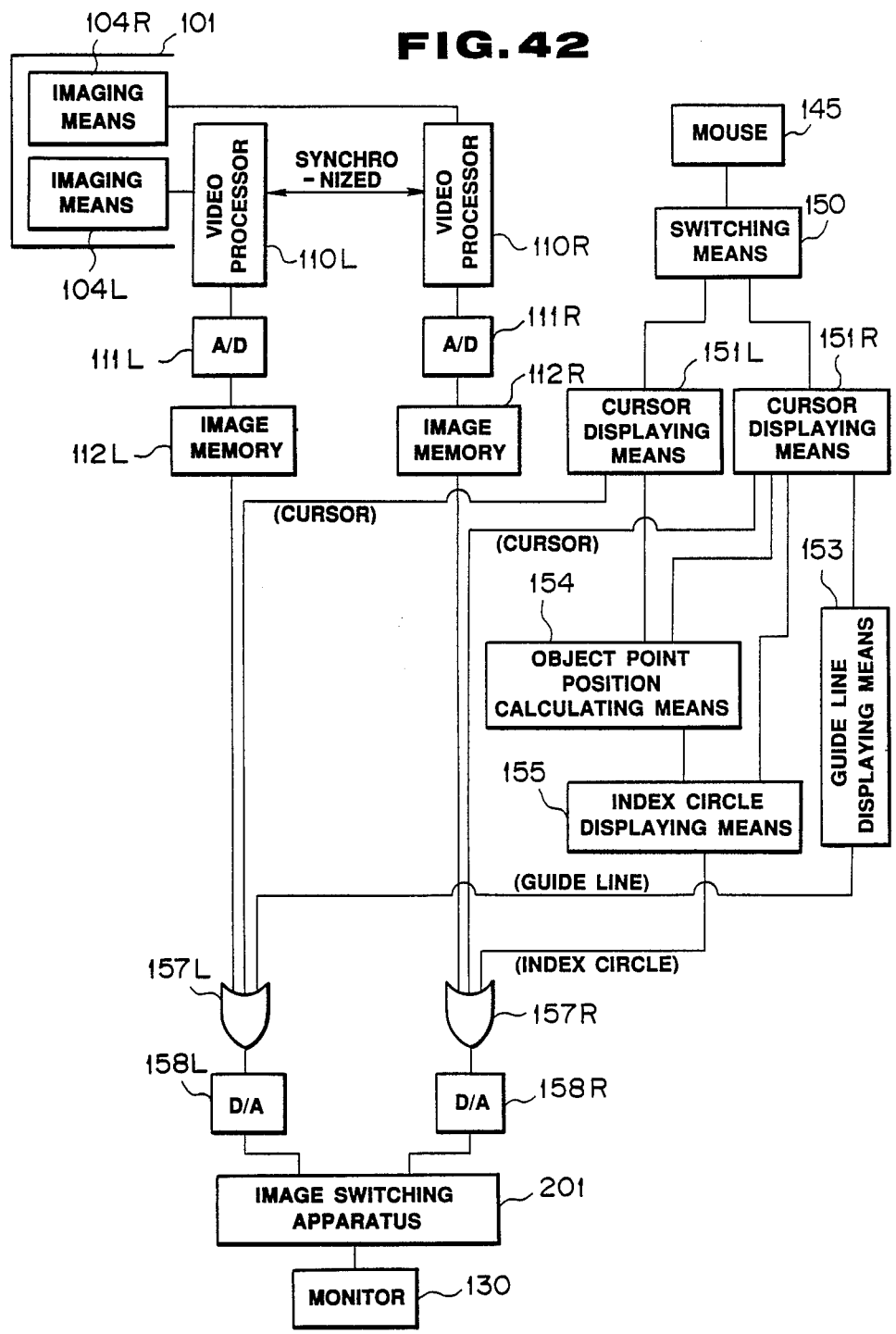
FIGS. 42 to 49 relate to the third embodiment of the present invention.
Figure 43:
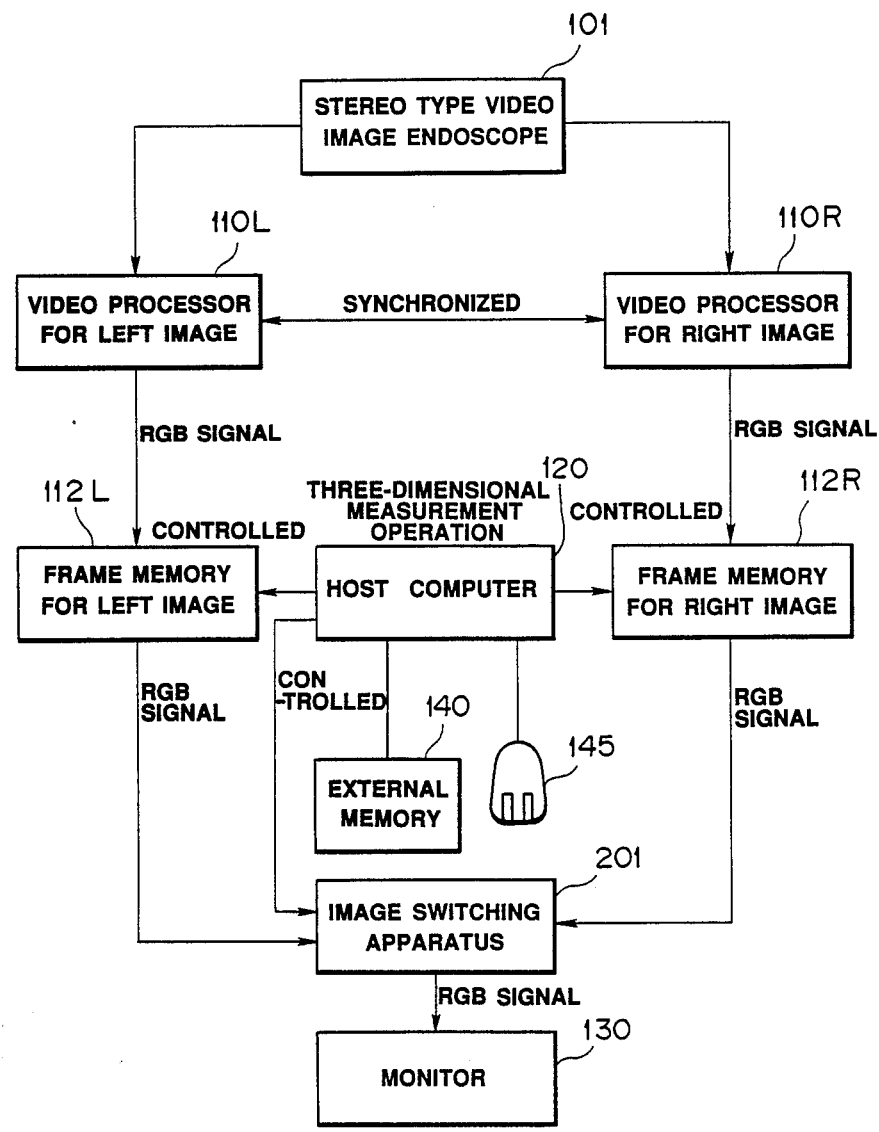

As shown in FIGS. 42 and 43, the measuring endoscope apparatus of this embodiment is provided with an image switching apparatus 201 which inputs image signals, for example, by RGB signals output from the right image frame memory 112R and left image frame memory 112L and selects either one of the right and left image signals so that the output of this image switching apparatus 201 may be input into one monitor 130. The above mentioned image switching apparatus 201 is controlled by a host computer 120.

Figure 44:
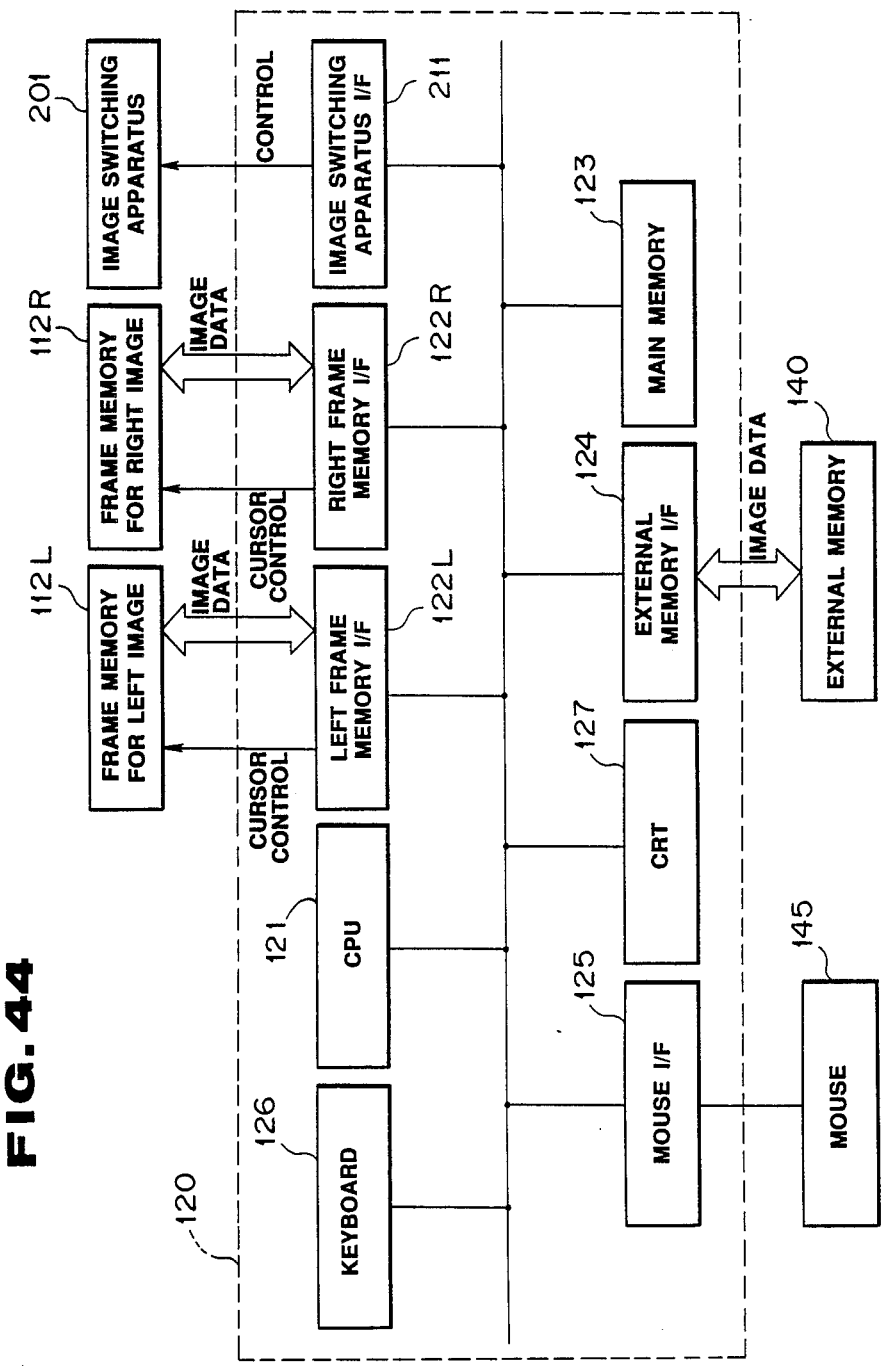

As shown in FIG. 44, the above mentioned host computer 120 is provided with an image switching apparatus interface 211 in addition to the formation in the second embodiment shown in FIG. 9. This image switching apparatus interface 211 is connected with a CPU by a bus and is connected to the above mentioned image switching apparatus 201. The above mentioned CPU 121 controls the image switching apparatus 201 through the image switching apparatus interface 211.

The operation in this embodiment shall be explained in the following.

In this embodiment, in the case of writing a cursor, drawing a guide line or writing an index circle, it is not written directly into the picture but is written into either right or left frame memory so that the image in either right or left frame memory may be displayed in the monitor as required.

Figure 45:
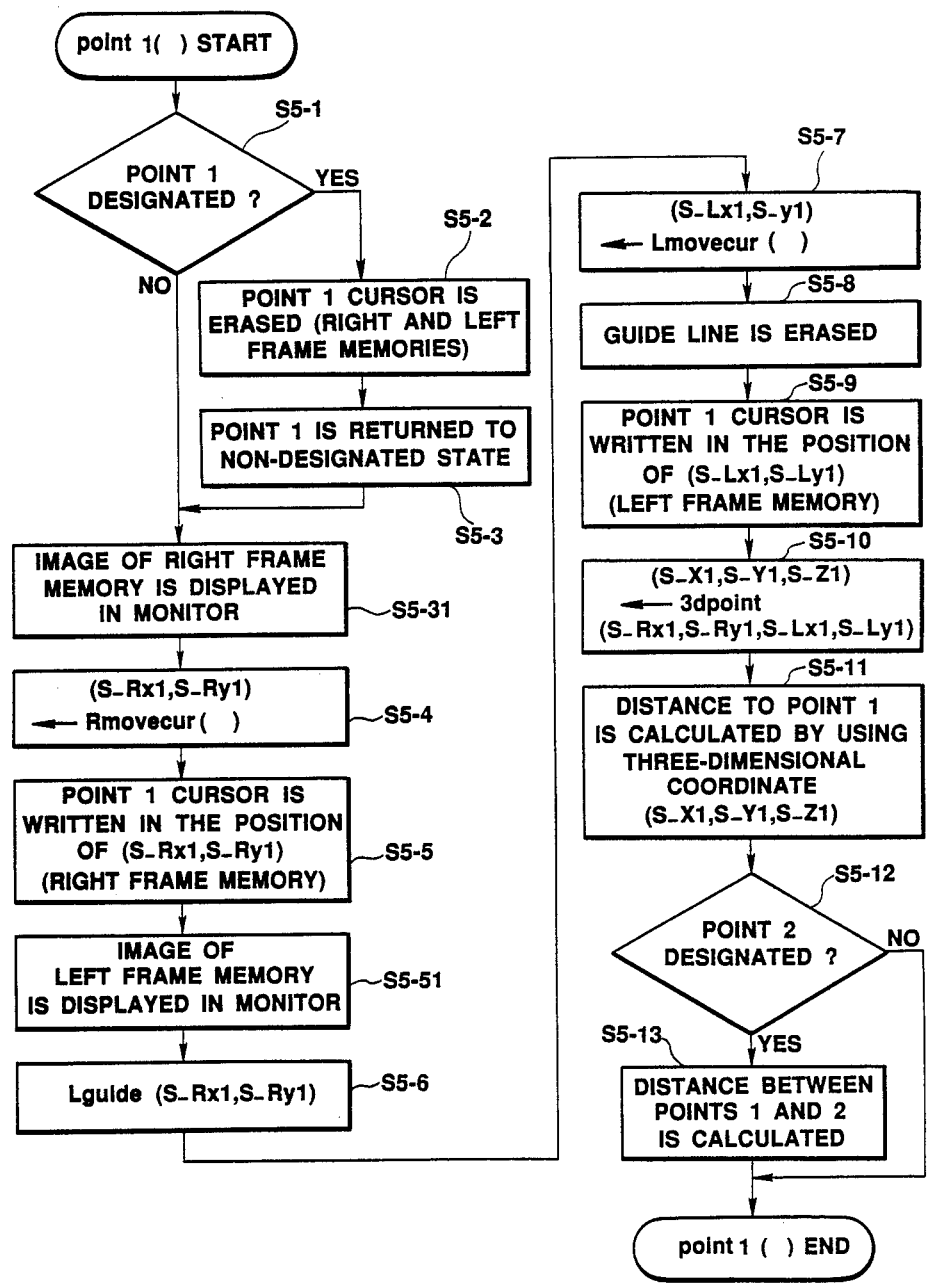

First of all, the point1 of this embodiment shall be explained by using FIG. 45 while comparing it with the point1 of the second embodiment shown in FIG. 20.

In S5-2, in the second embodiment, the point 1 cursor is erased in the respective right and left pictures, whereas, in this embodiment, the point 1 is erased in the right and left frame memories.

Also, S5-31 displaying the image of the right frame memory in the monitor is inserted between S5-3 and S5-4.

In S5-5, whereas, in the second embodiment, the point 1 cursor is written in the right picture, in this embodiment, the point 1 cursor is written in the right frame memory.

Also, S5-5 displaying the image of the left frame memory in the monitor is inserted between S5-5 and S5-6.

In S5-9, whereas, in the second embodiment, the point 1 cursor is written in the left picture, in this embodiment, the point 1 cursor is written in the left frame memor.

The others are the same as in the point1 of the second embodiment. Also, the same as the point1 shown in FIG. 45, the point2 writes the point 2 cursor in the right and left frame memories.

Figure 46:
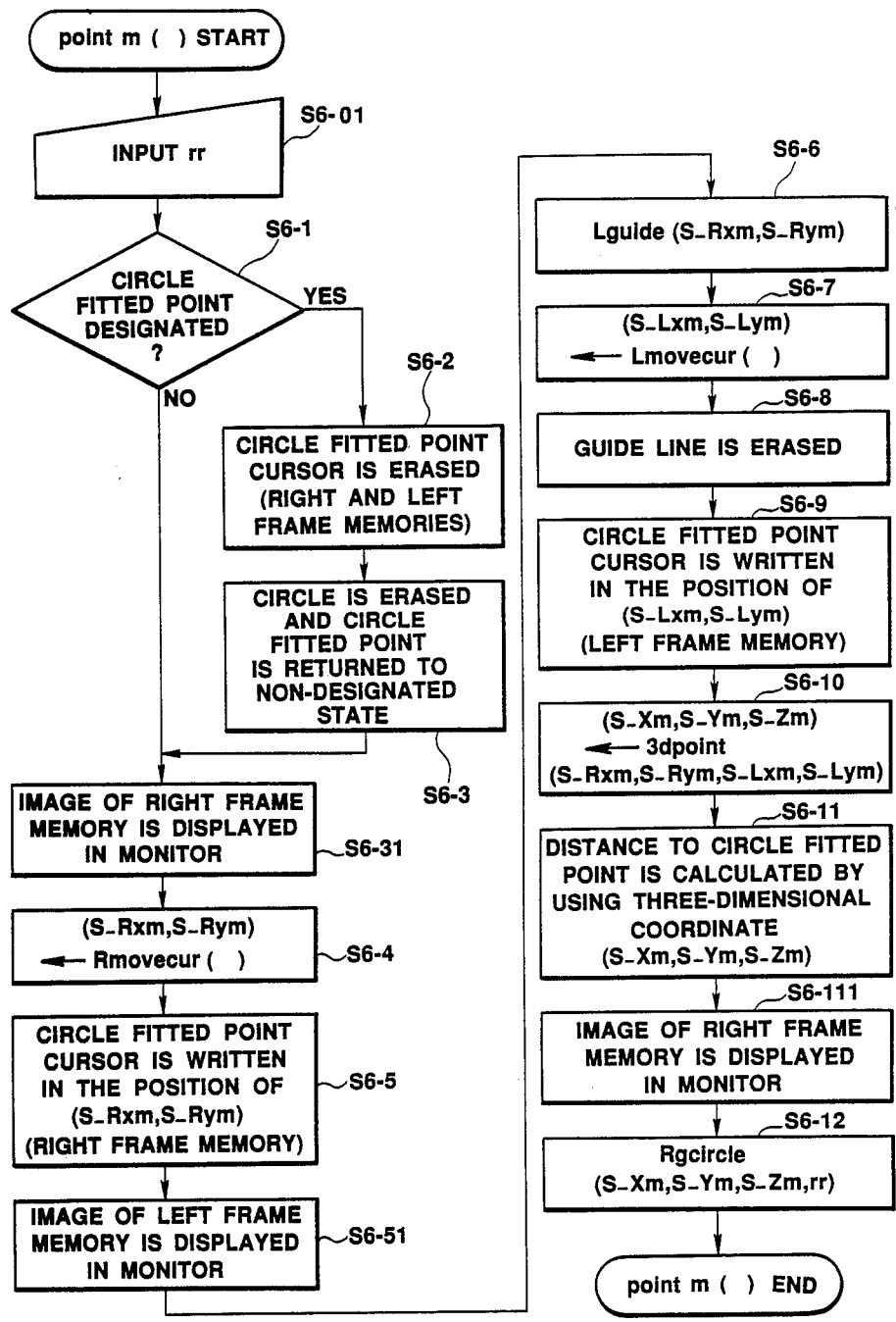

The pointm of this embodiment shall be explained in the following by using FIG. 46 while comparing it with the pointm of the second embodiment shown in FIG. 21.

In S6-2, whereas, in the second embodiment, the circle fitted point cursor is erased in the respective right and left pictures, in this embodiment, the circle fitted cursor is erased in the right and left frame memories.

S6-3 displaying the image of the right frame memory in the monitor is inserted between S6-3 and S6-4.

Also, in S6-5, whereas, in the second embodiment, the circle fitted point cursor is written in the right picture, in this embodiment, the circle fitted point cursor is written in the right frame memory.

S6-51 displaying the image of the left frame memory in the monitor is inserted between S6-5 and S6-6.

In S6-9, whereas, in the second embodiment, the circle fitted point cursor is written in the left picture, in this embodiment, the circle fitted point cursor is written in the left frame memory.

S6-111 displaying the image of the right frame memory in the monitor is inserted between S6-11 and S6-12.

The others are the same as in the pointm of the second embodiment.

Figure 47:
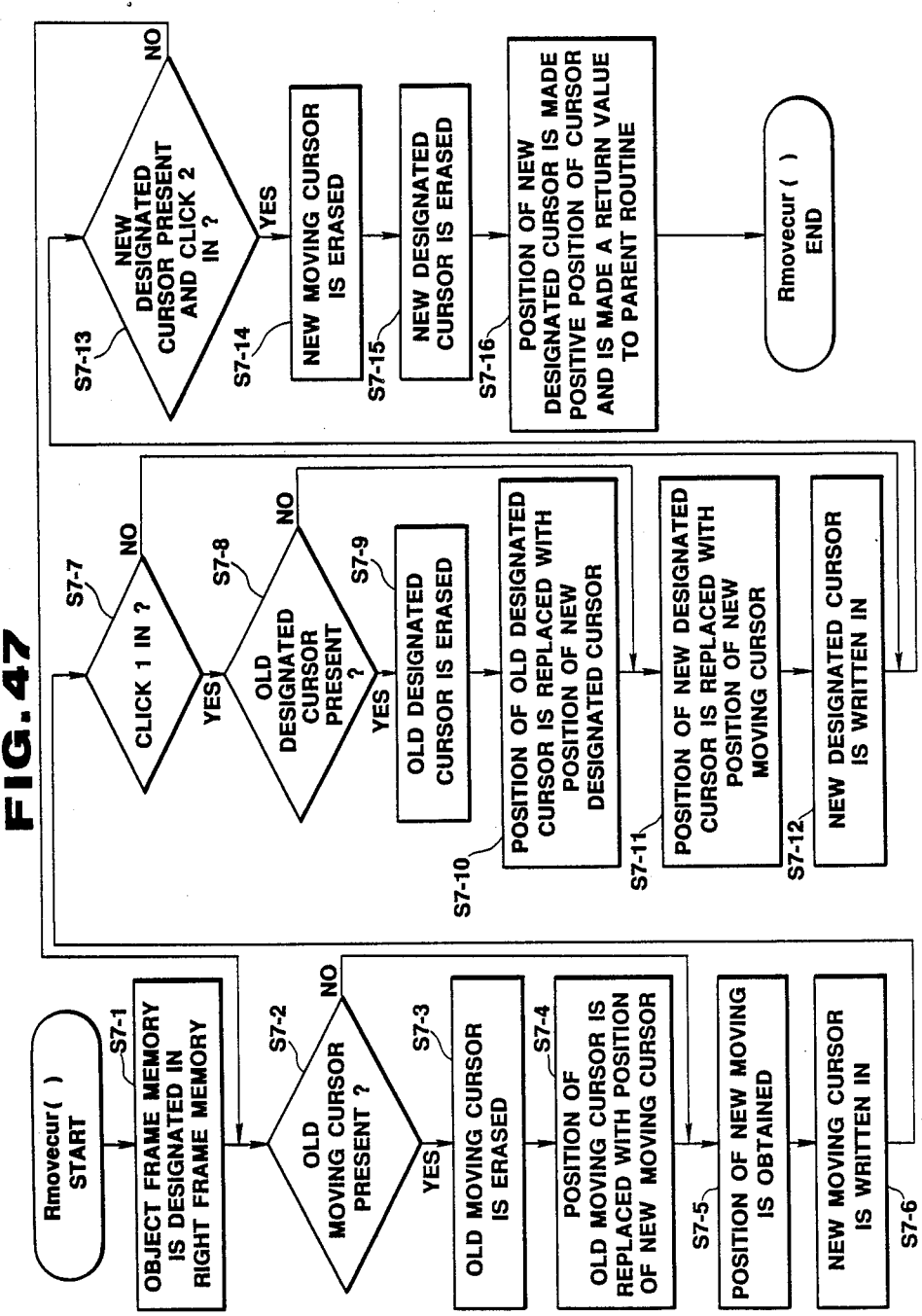

Now, the Rmovecur of this embodiment shall be explained in the following by using FIG. 47 while comparing it with the Rmovecur of the second embodiment shown in FIG. 22.

In S7-1, whereas, in the second embodiment, the object picture is designaged to be the right picture, in this embodiment, the object frame memory is designated to be the right frame memory.

The others are the same as in the Rmovecur of the second embodiment. By the way, the same as in the Rmovecur shown in FIG. 47, also, in the Lmovecur, the first step designates the object frame memory to be the left frame memory.

Figure 48:
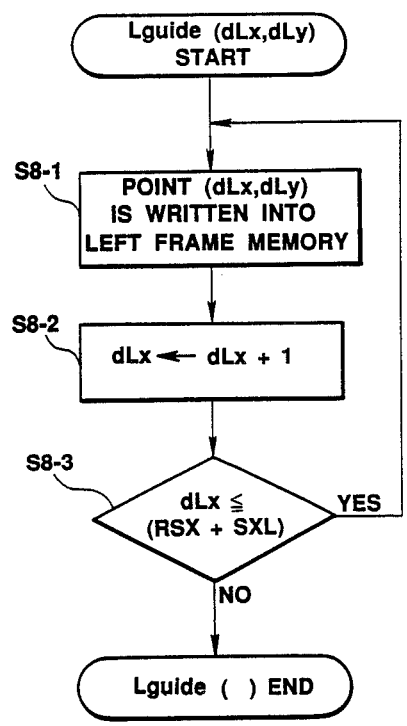

The Lguide of this embodiment shall be explained in the following by using FIG. 48 while comparing it with the Lguide of the second embodiment shown in FIG. 23.

In S8-1, whereas, in the second embodiment, the point (dLx, dLy) is written into the left picture, in this embodiment, the point (dLx, dLy) is written into the left frame memory.

The others are the same as in the Lguide of the second embodiment.

Figure 49:
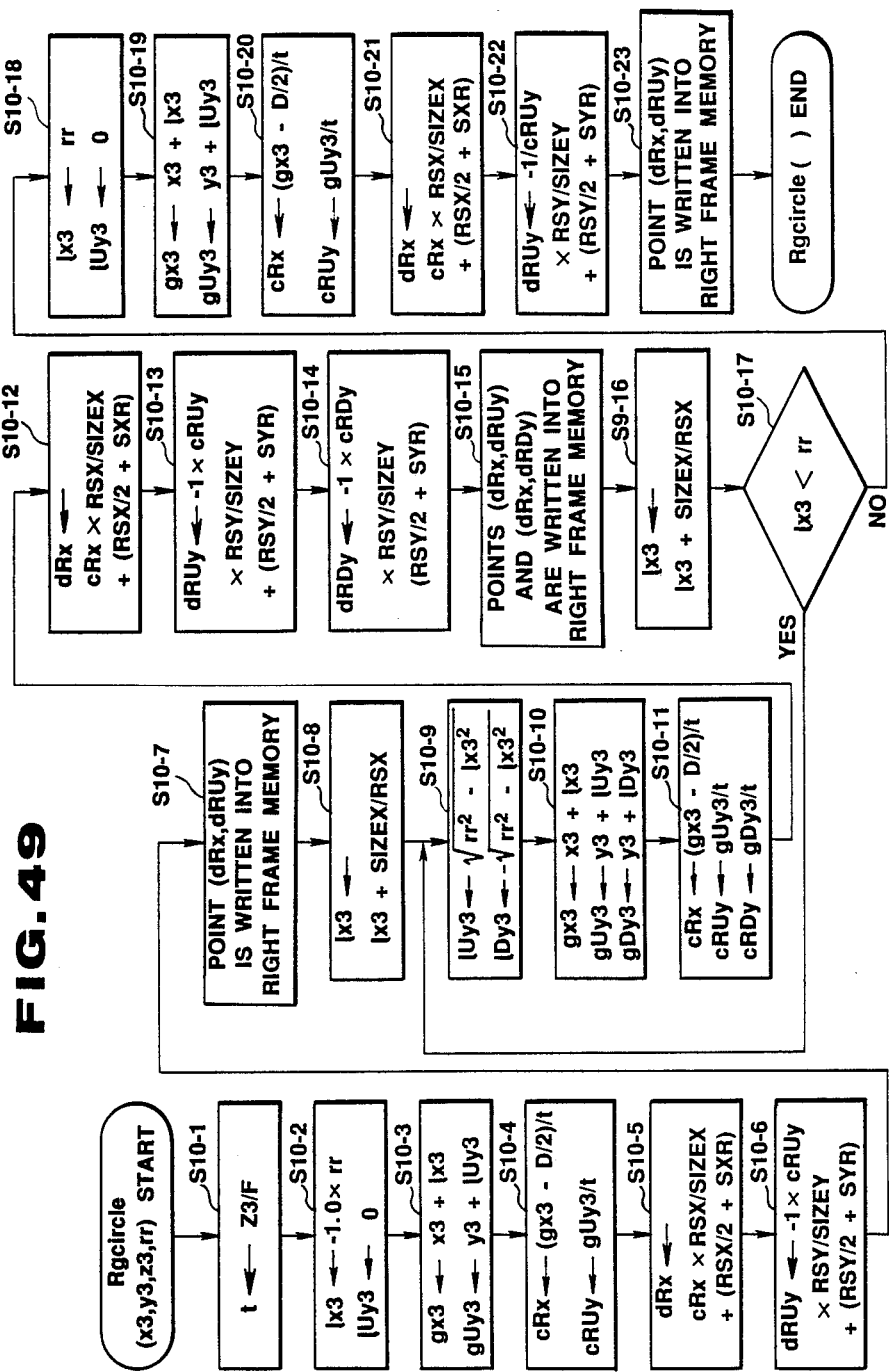

Now, the Rgcircle of this embodiment shall be explained in the following by using FIG. 49 while comparing it with the Rgcircle of the second embodiment shown in FIG. 25.

In S10-7, whereas, in the second embodiment, the point (dRx, dRUy) is written into the right picture, in this embodiment, the point (dRx, DRUy) is written into the right frame memory.

Also, in S10-15, whereas, in the second embodiment, the points (dRx, dRUy) and (dRx, dRDy) are written into the right picture, in this embodiment, the points (dRx, dRUy) and (dRx, dRDy) are written into the right frame memory.

Also, in S10-23, whereas, in the second embodiment, the point (dRx, dRUy) is written into the right picture, in this embodiment, the point (dRx, dRUy) is written into the right frame memory.

The others are the same as in the Rgcircle of the second embodiment.

Thus, according to this embodiment, with one monitor, the respective right and left pictures can be displayed and the object point can be designated.

The other formations, operations and effects are the same as in the second embodiment.

Figure 50:
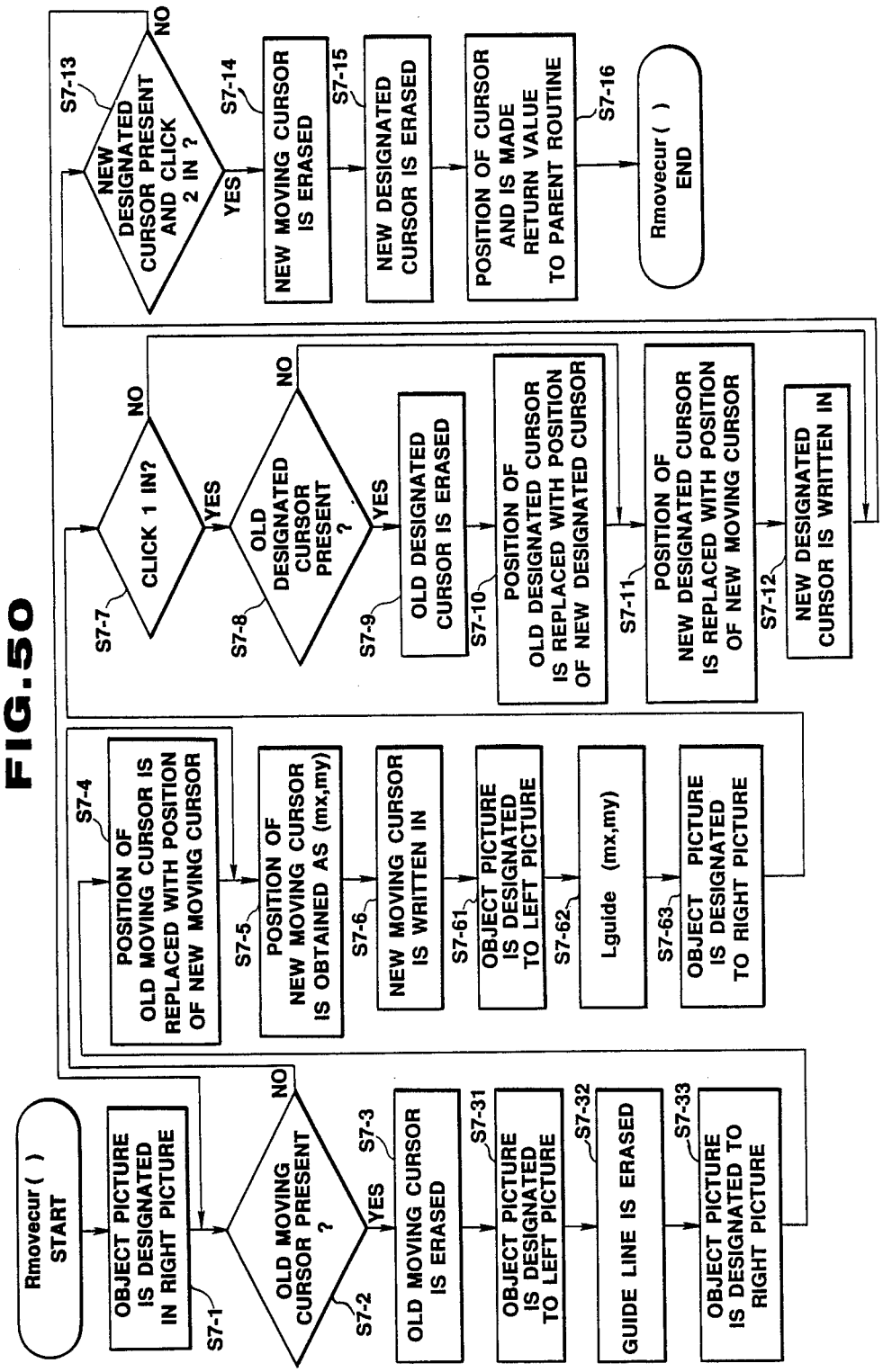
FIG. 50 is a flow chart for explaining the operation of the fourth embodiment.
Figure 51A:
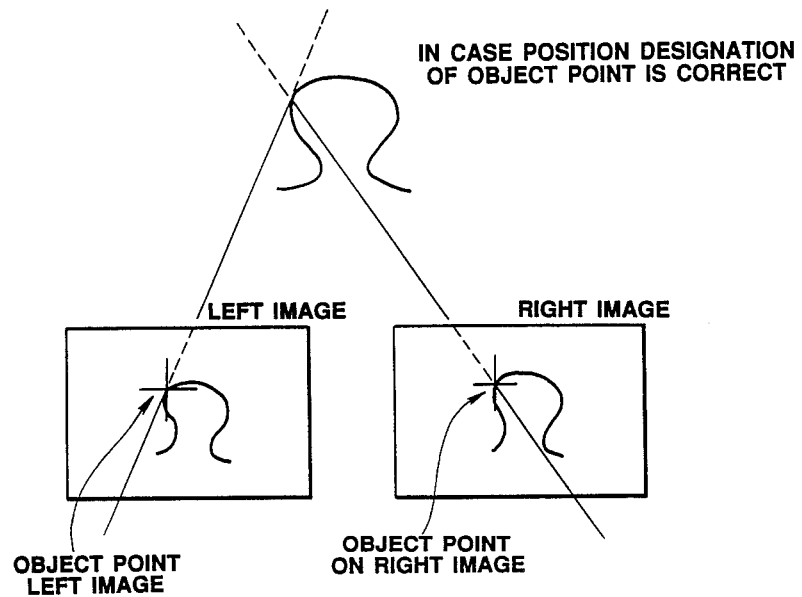
FIG. 51 is an explanatory view showing the position designation of a measuring object point in a measuring endoscope apparatus of a related art example.
Figure 51B:
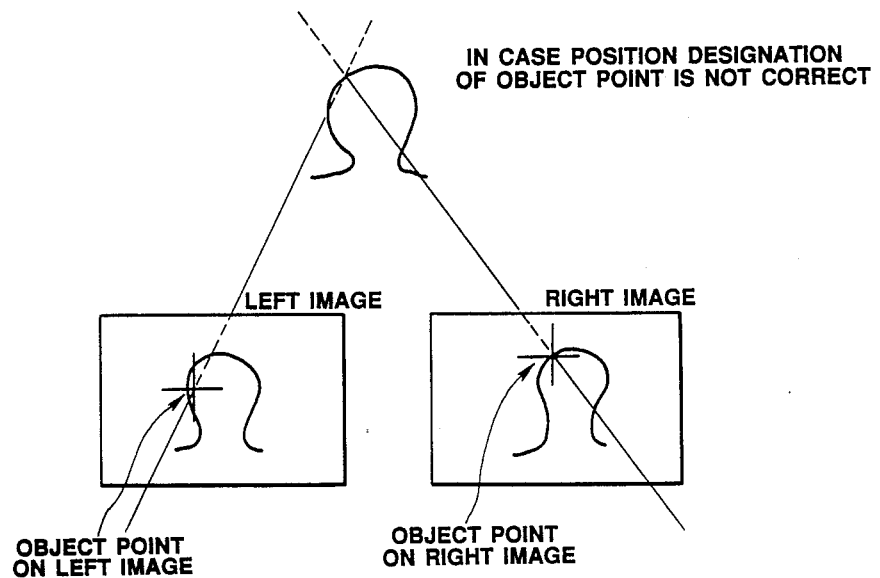

The fourth embodiment of the present invention is shown in FIG. 50.

In this embodiment, when the moving cursor is displayed on one picture, the guide line corresponding to the moving cursor will be displayed on the other picture and, when the above mentioned moving cursor is moved, the above mentioned guide line will also move.

The Rmovecur in this embodiment shall be explained by using FIG. 50 while comparing it with the Rmovecur of the second embodiment shown in FIG. 22.

In this embodiment, the following three steps are inserted between S7-3 and S7-4.

That is to say, in S7-3, the old moving cursor is erased and then, in S7-31, the object picture is designated to be the left picture. Then, in S7-32. the guide line written in this left picture is erased. Then, in S7-33, the object picture is designated to be the right picture and the process proceeds to S7-4.

Also, in S7-5, the position of the new moving cursor is obtained as (mx, my).

The following three steps are inserted between S7-6 and S7-7.

That is to say, in S7-6, the new moving cursor is written in and then, in S7-61, the object picture is designated to be the left picture. Then, in S7-62, the above mentioned (mx, my) is made an argument and the subroutine Lguide ( ) is made. That is to say, the guide line showing the position in which the point in the space specified by the above mentioned moving cursor should be located on the basis of the position of the moving cursor in the right picture is displayed in the left picture. Then, in S7-63, the object picture is designated to be the right picture and the process proceeds to S7-7.

The process in and after S7-7 is the same as in the second embodiment.

Thus, in the Rmovecur of this embodiment, the routine S7-62 writing in the left picture the guide line corresponding to the moving cursor of the right picture and the routine S7-32 erasing the guide line corresponding to the old moving cursor in case the moving cursor moves are added. Before writing or erasing the above mentioned guide line, the object picture is designated to be the left picture and, after writing or erasing the guide line, the object picture is designated to be the right picture.

By the way, the same as the Rmovecur shown in FIG. 50, also the Lmovecur displays in the right picture the guide line corresponding to the moving cursor on the left picture.

Therefore, in the case of designating the object point in the right picture, the corresponding position can be referred to by the guide line on the left picture and, in the case of designating the object point in the left picture, the position can be accurately designated by superimposing the guide line on the right picture on the designated point on the left picture.

Thus, according to this embodiment, in the case of designating the object point, the guide line will not be displayed on the picture on the designating side, the important image will not be hidden and, the same as in the second embodiment, the position of the object point will be able to be accurately designated.

The other formations, operations and effects are the same as in the second embodiment.

By the way, the pesent invention is not limited to the above mentioned respective embodiments. For example, the object points are not limited to be two but may be three or more and the cursors showing the respective object points may be distinguished by colors or shapes.

Also, instead of displaying the guide line, the picture of only the range near the part corresponding to the guide line may be displayed or the color of the part corresponding to the guide line may be made thin so as to display the range of the possibility of the object point to exist.

As an object point designating means, a cursor is not limited to be used but, for example, a light pen may be used.

The object point may be designated first in either of the right and left pictures.

A plurality of imaging means are not limited to be provided in the tip part of the insertable part of the endoscope but a plurality of image transmitting means consisting, for example, of fiber bundles may be provided within the insertable part and a plurality of imaging means may be provided at the rear ends of these image transmitting means. Also, one imaging means may be provided in the tip part of the insertable part so that a plurality of images having parallaxes may be imaged by moving the imaging means.

The respective right and left images may be displayed on the right and left in one monitor.

The index to be a criterion of the size is not limited to be a circle but may be a square or a line segment of a length corresponding to the distance.

It is apparent that, in this invention, working modes different in a wide range can be formed on the basis of this invention without deviating from the spirit and scope of the invention. This invention is not restricted by its specific working modes except being limited by the appended claims.

What is claimed is:

1. A three-dimensional measuring apparatus comprising:
    an imaging means for imaging a plurality of images having parallaxes;
    a displaying means for displaying said plurality of images obtained by said imaging means on a plurality of pictures;
    a first object point designating means for designating the first object point corresponding to a measuring object point in the space on the first image among said plurality of images displayed by said displaying means;
    a second object point designating means for designating the second object point corresponding to said measuring object point in the space on the second image among said plurality of images displayed by said displaying means;
    an object point designating auxiliary means for making an auxiliary process relating to the second object point designation by said second object point designating means after the first object point designation by said first object point designating means; and
    an operating means for making a measuring operation relating to the three-dimensional position of said measuring object point specified by said first object point designated by said first object point designating means and said second object point designated by said second object point designating means.

2. A three-dimensional measuring apparatus according to claim 1 wherein said operating means operates the three-dimensional coordinate of said measuring object point.

3. A three-dimensional measuring apparatus according to claim 1 wherein said operating means operates the distance between said measuring object point and said imaging means.

4. A three-dimensional measuring apparatus according to claim 1 wherein said first object point designating means and said second object point designating means can repectively designate a plurality of object points and said operating means operates the distance between two of a plurality of measuring object points specified by a set of a plurality of object points.

5. A three-dimensional measuring apparatus according to claim 1 wherein a memorizing means for memorizing the image obtained by said imaging means is further provided, said displaying means displays as a still image the image memorized by said memorizing means and said first object point designating means and said second object point designating means respectively designate object points on said still image displayed by said displaying means.

6. A three-dimensional measuring apparatus according to claim 1 wherein said displaying means has one monitor and a switching means for making said monitor selectively display any of said plurality of images.

7. A three-dimensional measuring apparatus according to claim 1 wherein said object point designating auxiliary means has an operating means for operating the position condition of the possibility of said second object point to exist on said second image from the position on said first image of the first object point designated by said first object point designating means; and an inhibiting means for making impossible the designation of said second object point by said second object point designating means outside the range of meeting the position condition operated by said operating means.

8. A three-dimensional measuring apparatus according to claim 7 wherein:
said first object point designating means has a first cursor displaying means for displaying the first cursor for designating said first object point on the first picture on which said first image is displayed;
said second object point designating means has a second cursor displaying means for displaying the second cursor for designating the second object point on the second picture on which said second image is displayed; and
said inhibiting means has a means for making said second cursor movable only within the range meeting said position condition.

9. A three-dimensional measuring apparatus according to claim 1 wherein:
said operating means has an object point position operating means for operating the three-dimensional position of said measuring object point specified by said first object point and said second object point; and
said three-dimensional measuring apparatus further comprises an index displaying means for displaying an index of a size corresponding to the position of said measuring object point operated by said object point position operating means near at least one of said first object point and said second object point.

10. A three-dimensional measuring apparatus according to claim 9 wherein said index is a two-dimensional index.

11. A three-dimensional measuring apparatus according to claim 9 wherein said index is a circle.

12. A three-dimensional measuring apparatus according to claim 9 wherein, in the case of operating the three-dimensional position of said measuring object point, said object point position operating means corrects the distortion aberration of the optical system forming the image in said imaging means and, in the case of displaying said index, said index displaying means corrects the distortion aberration of the optical system forming the image in said imaging means.

13. A three-dimensional measuring apparatus according to claim 1 wherein:
said first object point designating means has a first cursor displaying means for displaying a first cursor for designating said first object point on the first picture on which said first image is displayed; and
said second object point designating means has a second cursor displaying means for displaying a second cursor for designating said second object point on the second picture on which said second image is displayed.

14. A three-dimensional measuring apparatus according to claim 13 wherein:
said first object point designating means and said second object point designating means have a common cursor operating means for moving said first cursor and said second cursor on the respective pictures and designating the respective object points by using said respective cursors; and
said object point designating auxiliary means has a switching means for operatively connecting said cursor operating means and said first cursor displaying means with each other before said first object point is designated, releasing said cursor operating means and said first cursor displaying means from the connection after said first object point is designated and operatively connecting said cursor operating means and said second cursor displaying means with each other.

15. A three-dimensional measuring apparatus according to claim 13 wherein said object point designating auxiliary means has a guide line displaying means for displaying a guide line meeting the position condition on said first picture of the point in the space corresponding to said second cursor on said first picture on the basis of the position information on said second picture of said second cursor.

16. A three-dimensional measuring apparatus according to claim 5 wherein said second cursor displaying means displays said second cursor on said second picture only when operatively connected to said cursor operating means by said switching means.

17. A three-dimensional measuring apparatus according to claim 1 whererin said object point designating auxiliary means has a guide means for operating the position condition of the possibility of said second object point to exist on said second image from the position on said first image of the first object point designated by said first object point designating means and displaying the range of the possibility of said second object point to exist on said second picture on the basis of said position condition.

18. A three-dimensional measuring apparatus according to claim 17 wherein said guide means has a guide line displaying means for displaying a guide line showing the range of the possibility of said second object point to exist on said second picture.

19. A three-dimensional measuring apparatus according to claim 18 wherein said object point designating auxiliary means further has a warning means for checking whether the second object point designated by said second object point designating means is located on said guide line or not and issuing a warning in case said second object point is not located on said guide line.

20. A three-dimensional measuring apparatus according to claim 18 wherein said guide line displaying means corrects the distortion aberratiion of the optical system forming an image in said imaging means in the case of operating the position condition of the possibility of said second object point to exist.

21. A three-dimensional measuring apparatus according to claim 18 wherein said guide line consists of one line meeting said position condition.

22. A three-dimensional measuring apparatus according to claim 18 wherein said guide line consists of two lines holding the range meeting said position condition.

23. A three-dimensional measuring apparatus according to claim 18 wherein said object point designating auxiliary means further has an inhibiting means for making impossible the designation of said second object point by said second object point designating means is made impossibe except on said guide line.

24. A three-dimensional measuring apparatus according to claim 23 wherein:
said first object point designating means has a first cursor displaying means for displaying a first cursor for said first object point designation on the first picture on which said first image is displayed;
said second object point designating means has a second cursor displaying means for displaying a second cursor for said second object point designation is displayed on the second picture on which said second image; and
said inhibiting means has a means for making said second cursor movable only on said guide line.

25. A three-dimensional measuring apparatus comprising:
an imaging means for imaging a plurality of images having parallaxes;
a displaying means for displaying said plurality of images obtained by said imaging means on a plurality of pictures;
a first object point designating means for designating the first object point corresponding to a measuring object point in the space on the first image among said plurality of images displayed by said displaying means;
a second object point designating means for designating the second object point corresponding to said measuring object poinnt in the space on the second image among said plurality of images displayed by said displaying means;
an object point position operating means for operating the three-dimensional position of said measuring object point specified by said first object point designated by said first object point designating means and said second object point designated by said second object point designating means; and
an index displaying means for displaying an index of a size corresponding to the position of said measuring object point operated by said object point position operating means near at least one of said first object point and said second object point on the picture displayed by said displaying means.

26. A three-dimensional measuring endoscope apparatus comprising:
an endoscope body which comprises an elongate insertable part having a tip part and an image forming means provided in said tip part of said insertable part for forming a plurality of object images having parallaxes;
an imaging means for imaging the plurality of images having parallaxes and formed by said image forming means;
a displaying means for displaying on a plurality of pictures said plurality of images obtained by said imaging means;
a first object point designating means for designating the first object point corresponding to a measuring object point in the space on the first image among said plurality of images displayed by said displaying means;
a second object point designating means for designating the second object point corresponding to said measuring object point in the space on the second image among saide plurality of images displayed by said displaying means;
an object point designating auxiliary means for making an auxiliary process relating to the second object point designation by said second object point designating means after the first object point designation by said first object point designating means; and
an operating means for making a measuring operation relating to the three-dimensional position of said measuring object point specified by said first object point designated by said first object point designating means and said second object point designated by said second object point designating means.

27. A three-dimensional measuring endoscope apparatus according to claim 26 wherein said image forming means has a plurality of image forming optical systems arranged in a plurality of positions having parallaxes in said tip part of said insertable part.

28. A three-dimensional measuring endoscope apparatus according to claim 27 wherein said imaging means has a plurality of solid state imaging devices arranged in the respective image forming positions of said plurality of image forming optical systems within said tip part of said insertable part.

29. A three-dimensional measuring endoscope apparatus comprising:
an endoscope body which comprises an elongate insertable part having a tip part and an image forming means provided in said tip part of said insertable part for forming a plurality of object images having parallaxes;
an imaging means for imaging the first and second images having parallaxes and formed by said image forming means;
a displaying means for displaying said first and second images obtained by said imaging means;
a first object point designating means for designating the first object point corresponding to the measuring object point in the space on said first image displayed by said displaying means; and
an operating means for operating the position condition on said second image of said measuring object point designated by said first object point on the basis of the position information on said first image of said first object point.

30. A three-dimensional measuring endoscope apparatus according to claim 29 further comprising a guide line displaying means for displaying a guide line determined on the basis of the position condition operated by said operating means together with said second image.

31. A three-dimensional measuring endoscope apparatus according to claim 29 or 30 further comprising a second object point designating means for designating the second object point corresponding to said measuring object point in the space on said second image displayed by said displaying means and a judging means for judging whether the position information of said second object point designated by said second object point designating means meets said position condition obtained by said operating means or not.

32. A three-dimensional measuring endoscope apparatus according to claim 31 wherein said judging means has a means for issuing a warning when said position information does not meet said position condition.

33. A three-dimensional measuring endoscope apparatus according to claim 30 wherein said guide line consists of one line meeting said position condition.

34. A three-dimensional measuring endoscope apparatus according to claim 30 wherein said guide line consists of two lines holding the range meeting said position condition.

35. A three-dimensional measuring apparatus comprising:
an imaging means for imaging a plurality of images having parallaxes;
a displaying means for displaying said plurality of images obtained by said imaging means on a plurality of pictures;
a first object point designating means for designating the first object point corresponding to the measuring object point in the space on the first image among said plurality of images displayed by said displaying means;
a moving point displaying means for displaying any movable moving point on the second image among said plurality of images displayed by said displaying means; and
a guide line displaying means for displaying the guide line meeting the position condition on said first image of the point in the space corresponding to said moving point on said first image on the basis of the position information on said second image of said moving point displayed by said moving point displaying means.

36. A point designating method in an endoscope image displaying apparatus in which images from positions having parallaxes with each other for the inspecting part are displayed respectively on the first and second pictures and the parts corresponding to each other on the respective pictures are designated by a point designating means, comprising the respective steps of:
displaying the first poinnt moved by the operation of said point designated means only on said first picture;
designating said first point, in said first point dislpalying step, by making said first point the first immovable point in response to the designating operation of said point designating means and continuing to display this first immovable point;
displaying a second point moved by the operation of said designating means on said second picture in response to the designation of said first point by said first point designating step; and
designating said second point, in said second point displaying step, by making said second point the second immovable point in response to the designating operation of said point designating means and continuing to display this second immovable point.

* * * * *